United States Patent
Yankeelov et al.

(10) Patent No.: US 12,423,806 B2
(45) Date of Patent: Sep. 23, 2025

(54) CHARACTERIZATION OF LESIONS VIA DETERMINATION OF VASCULAR METRICS USING MRI DATA

(71) Applicants: Board of Regents, The University of Texas System, Austin, TX (US); The University of Chicago, Chicago, IL (US)

(72) Inventors: Thomas Yankeelov, Austin, TX (US); Gregory Karczmar, Chicago, IL (US); Chengyue Wu, Austin, TX (US); David Hormuth, Austin, TX (US); Todd A. Oliver, Austin, TX (US); Robert D. Moser, Austin, TX (US); Federico Pineda, Chicago, IL (US); Ty Easley, Chicago, IL (US); Rina F. Barber, Chicago, IL (US); Byol Kim, Chicago, IL (US); Deepa Sheth, Chicago, IL (US); Aytekin Oto, Chicago, IL (US); Hiroyuki Abe, Chicago, IL (US); Milica Medved, Chicago, IL (US); Xiaobing Fan, Chicago, IL (US); Aritrick Chatterjee, Chicago, IL (US); Shiyang Wang, Columbia, MO (US)

(73) Assignees: Board of Regents, The University of Texas System, Austin, TX (US); The University of Chicago, Chicago, IL (US)

(*) Notice: Subject to any disclaimer, the term of this patent is extended or adjusted under 35 U.S.C. 154(b) by 0 days.

(21) Appl. No.: 17/766,197

(22) PCT Filed: Oct. 2, 2020

(86) PCT No.: PCT/US2020/054127
§ 371 (c)(1),
(2) Date: Apr. 1, 2022

(87) PCT Pub. No.: WO2021/067853
PCT Pub. Date: Apr. 8, 2021

(65) Prior Publication Data
US 2025/0272828 A1    Aug. 28, 2025

Related U.S. Application Data

(60) Provisional application No. 62/910,286, filed on Oct. 3, 2019.

(51) Int. Cl.
*G06T 7/00*    (2017.01)
*A61B 5/00*    (2006.01)
(Continued)

(52) U.S. Cl.
CPC ............ *G06T 7/0012* (2013.01); *A61B 5/004* (2013.01); *A61B 5/055* (2013.01); *G06T 3/40* (2013.01);
(Continued)

(58) Field of Classification Search
None
See application file for complete search history.

(56) References Cited

U.S. PATENT DOCUMENTS

| | | |
|---|---|---|
| 2010/0142786 A1 | 6/2010 | Degani et al. |
| 2014/0107469 A1 | 4/2014 | Gjesdal et al. |

(Continued)

OTHER PUBLICATIONS

Padhani, A.R., Khan, A.A. Diffusion-weighted (DW) and dynamic contrast-enhanced (DCE) magnetic resonance imaging (MRI) for monitoring anticancer therapy. Targ Oncol 5, 39-52 (2010). (Year: 2010).*

(Continued)

*Primary Examiner* — SJ Park
*Assistant Examiner* — Caroline E. Depalma
(74) *Attorney, Agent, or Firm* — Foley & Lardner LLP

(57) ABSTRACT

Disclosed are approaches to non-invasively characterize a tumor or other lesion in a region of interest (ROI) based on various analyses of magnetic resonance imaging (MRI) data. The MRI data may correspond to ultrafast dynamic contrast enhanced MRI (DCE-MRI) and high spatial resolution (Continued)

DCE-MRI scans, and diffusion-weighted MRI (DW-MRI) scans of the ROI. Vasculature metrics may be determined, and tumor-associated blood flow velocity and/or tumor interstitial pressure may be obtained using the vasculature metrics as inputs to a computational fluid dynamics model. A combination of morphological vascular metrics and functional vascular metrics may be used to characterize the tumor. Malignancy, aggressiveness, treatment response, and other features of tumors or other lesions, in the breast or other regions of a patient, may be characterized through disclosed analyses of MRI data.

20 Claims, 29 Drawing Sheets

(51) Int. Cl.
| | |
|---|---|
| *A61B 5/055* | (2006.01) |
| *G06T 3/40* | (2024.01) |
| *G06T 7/11* | (2017.01) |
| *G06T 7/136* | (2017.01) |
| *G06T 7/155* | (2017.01) |
| *G06T 7/20* | (2017.01) |

(52) U.S. Cl.
CPC ............... *G06T 7/11* (2017.01); *G06T 7/136* (2017.01); *G06T 7/155* (2017.01); *G06T 7/20* (2013.01); *G06T 2207/10088* (2013.01); *G06T 2207/20044* (2013.01); *G06T 2207/20076* (2013.01); *G06T 2207/30096* (2013.01); *G06T 2207/30104* (2013.01)

(56) References Cited

U.S. PATENT DOCUMENTS

| | | | |
|---|---|---|---|
| 2015/0050218 | A1 | 2/2015 | Giavazzi et al. |
| 2016/0022169 | A1 | 1/2016 | Breeuwer et al. |
| 2016/0058304 | A1* | 3/2016 | Emblem ............... A61B 5/4842 600/420 |
| 2019/0198177 | A1 | 6/2019 | Thomas, Jr. et al. |
| 2019/0246938 | A1 | 8/2019 | Gharagouzloo et al. |

OTHER PUBLICATIONS

Wu C, Pineda F, Hormuth Da II, Karczmar GS, Yankeelov TE. Quantitative analysis of vascular properties derived from ultrafast DCE-MRI to discriminate malignant and benign breast tumors. Magn Reson Med. 2019; 81: 2147-2160. (Year: 2019).*

Assili et al. "Dynamic Contrast Magnetic Resonance Imaging (DCE-MRI) and Diffusion Weighted MR Imaging (DWI) for Differentiation between Benign and Malignant Salivary Gland Tumors", J Biomed Phys Eng 2015. Retrieved on Jan. 12, 2021. Retrieved from URL: https://www.ncbi.nlm.nih.gov/pmc/articles/PMC4681460/pdf/jbpe-5-157.pdf.

Hompland et al. "Connective tissue of cervical carcinoma xenografts: Associations with tumor hypoxia and interstitial fluid pressure and its assessment by DCE-MRI and DW-MRI", Acta Oncologica, 2014. Retrieved on Jan. 12, 2021. Retrieved from URL: https://www.tandfonline.com/doi/pdf/10.3109/0284186X.2013.773073.

International Search Report and Written Opinion issued in connection with PCT/US2020/054127 dated Feb. 19, 2021.

Langer et al. "Prostate Cancer Detection With Multi-parametric MRI: Logistic Regression Analysis of Quantitative T2, Diffusion-Weighted Imaging, and Dynamic Contrast-Enhanced MRI", Journal of Magnetic Resonance Imaging, 2009. Retrieved on Jan. 10, 2021. Retrieved from URL: https://onlinelibrary.wiley.com/doi/pdf/10.1002/jmri.21824.

Wu et al. "Quantitative analysis of vascular properties derived from ultrafast DCE-MRI to discriminate malignant and benign breast tumors", Magn Reson Med. Mar. 2019. Retrieved on Jan. 13, 2021. Retrieved from URL: https://www.ncbi.nlm.nih.gov/pmc/articles/PMC6347496/pdf/nihms-987020.pdf.

* cited by examiner

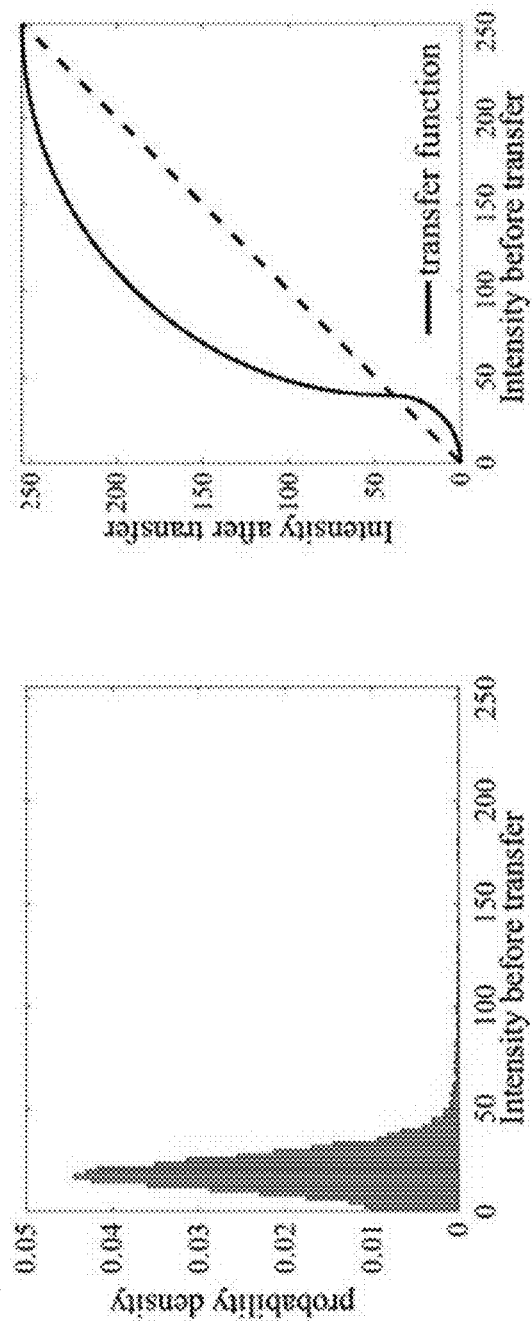
FIG. 4A
FIG. 4B
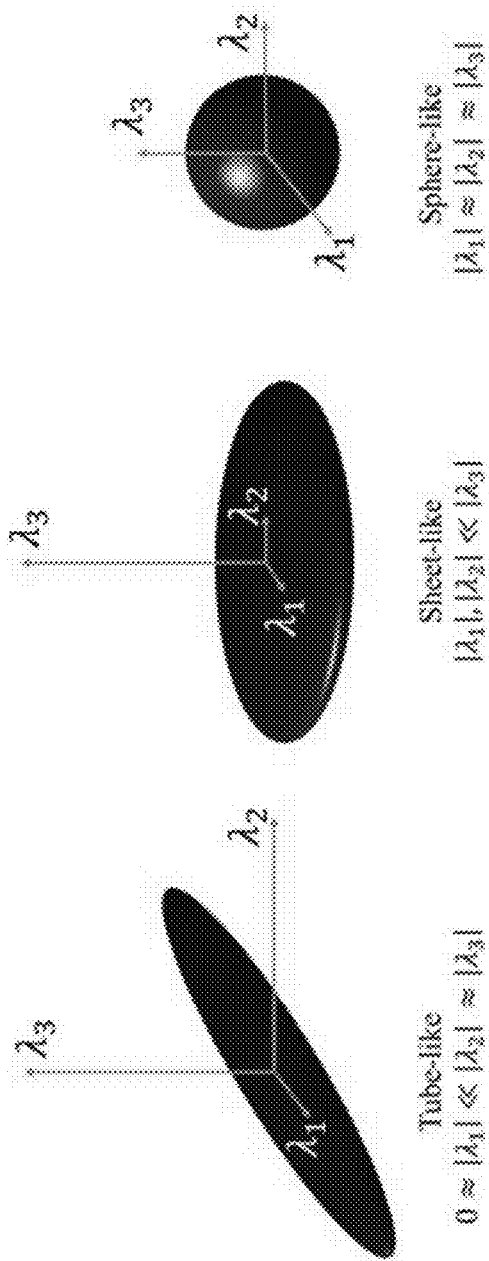
FIG. 4C

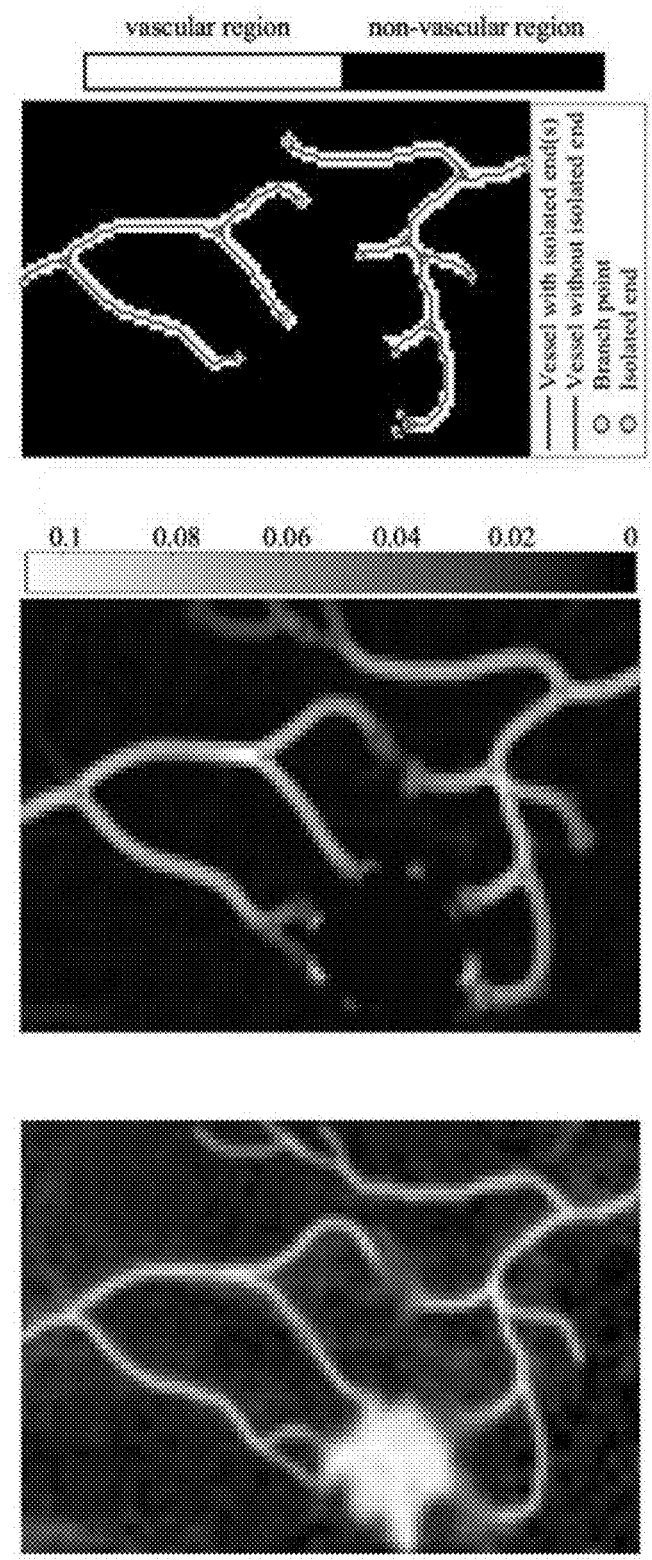

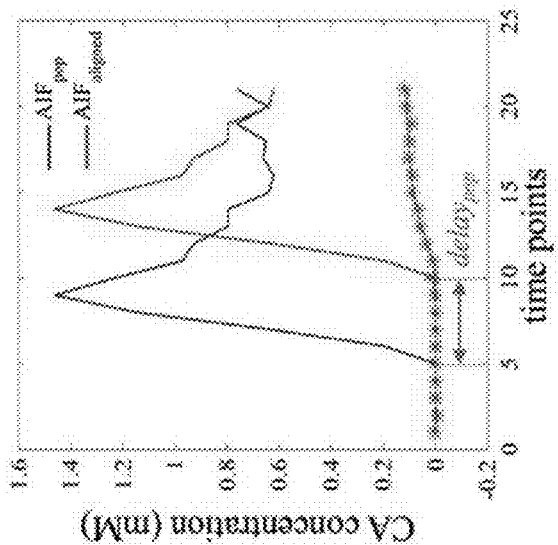
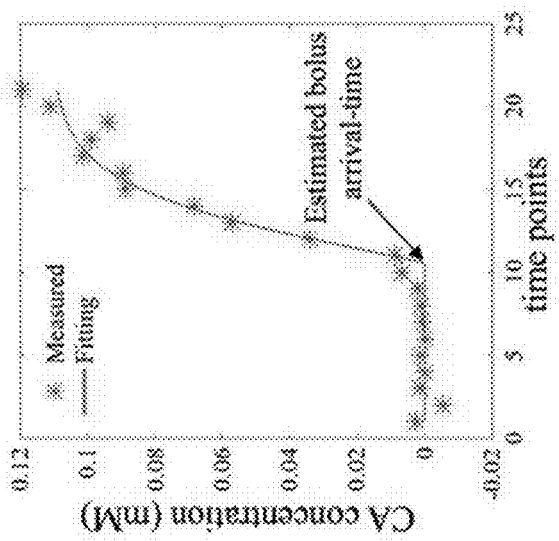
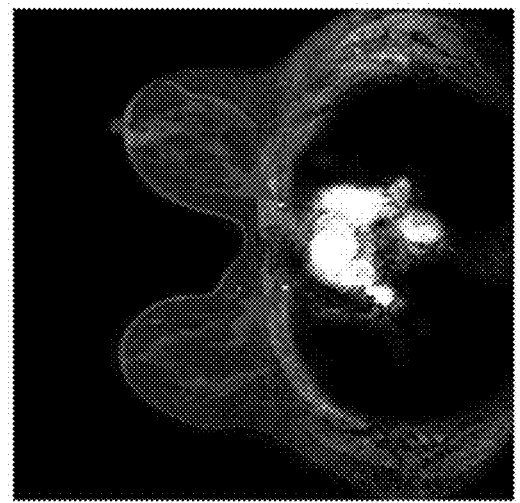
FIG. 5A
FIG. 5B
FIG. 5C

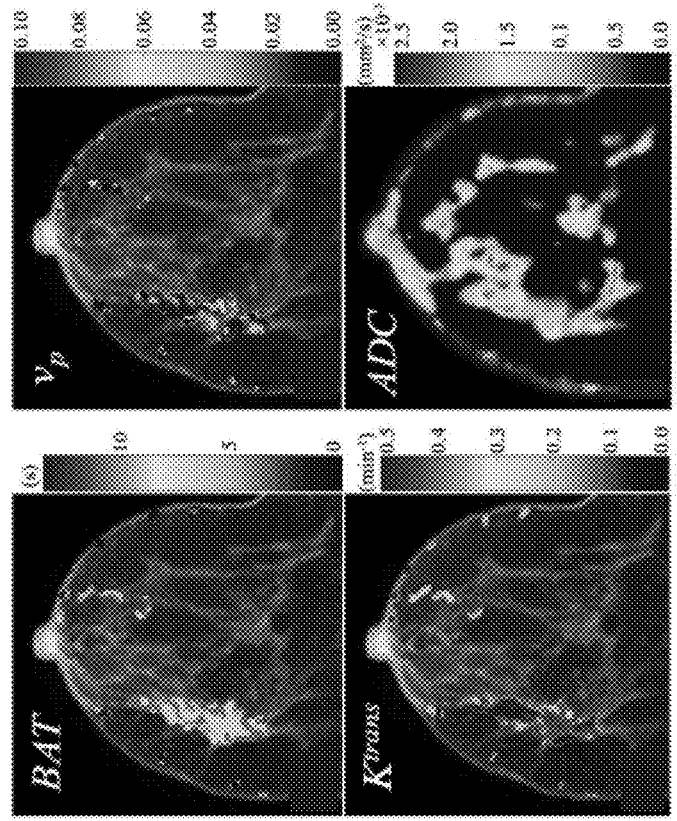
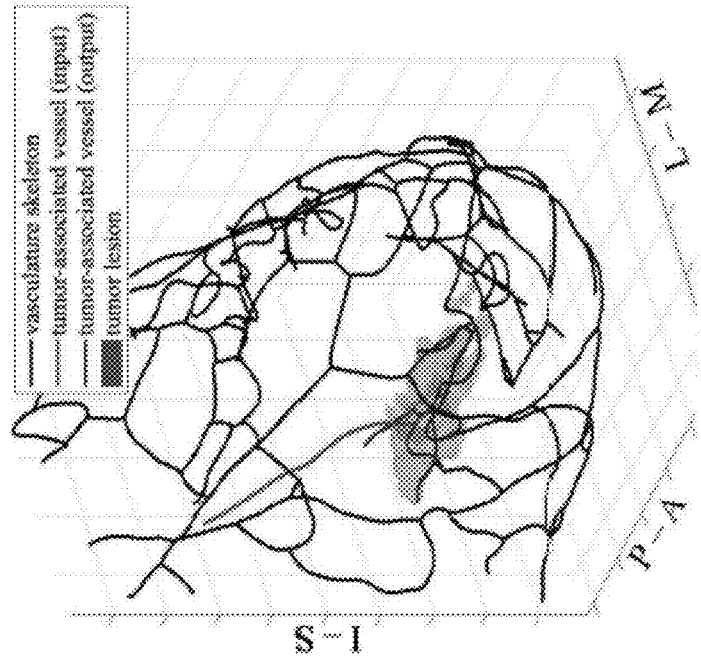
FIG. 11A  FIG. 11B  FIG. 11C  FIG. 11D  FIG. 11E

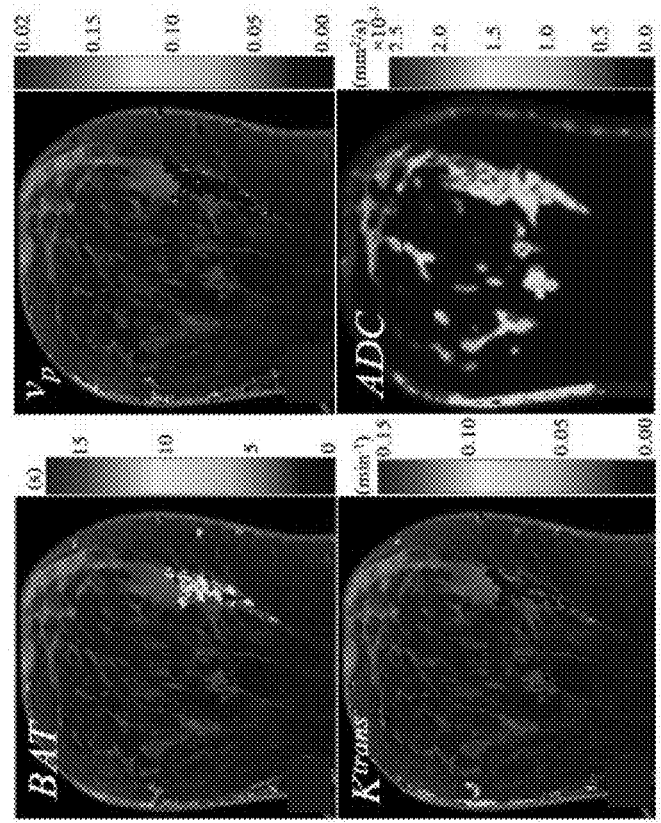
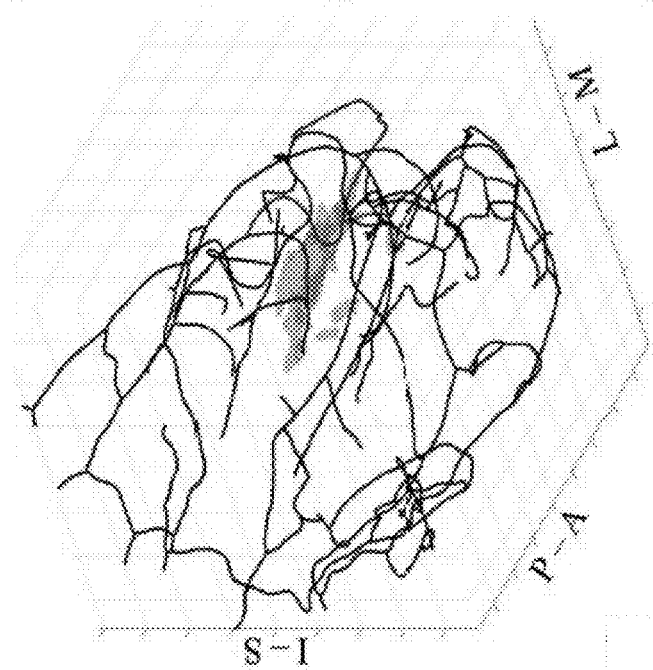
FIG. 11H  FIG. 11J  FIG. 11G  FIG. 11I  FIG. 11F

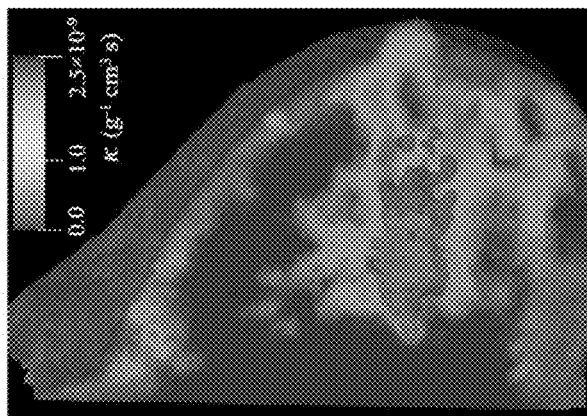 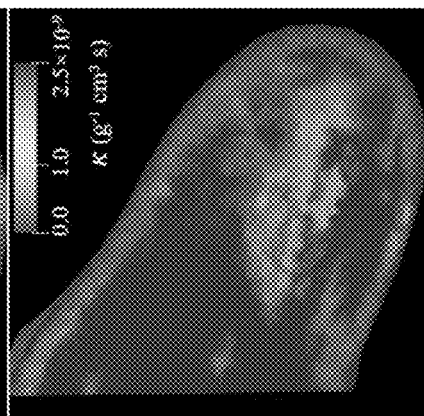
FIG. 12D FIG. 12H
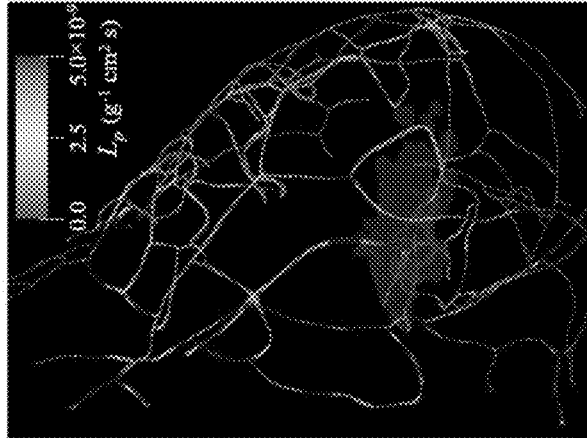 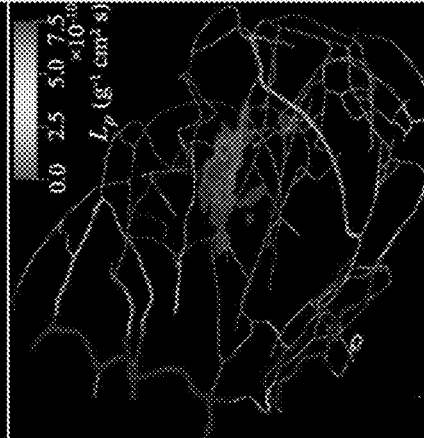
FIG. 12C FIG. 12G
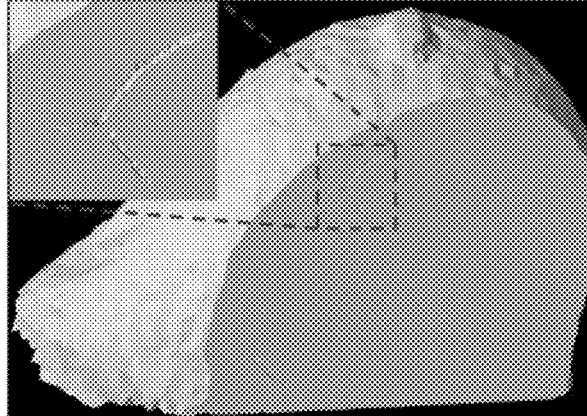 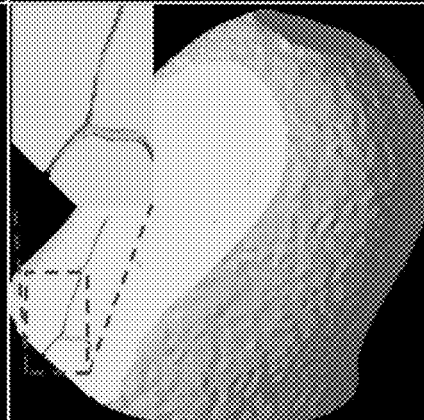
FIG. 12B FIG. 12F
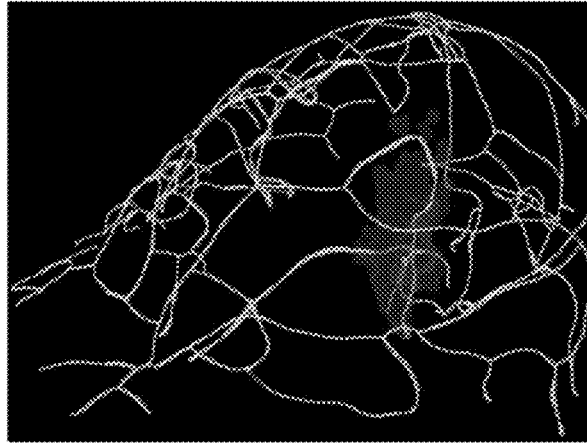 
FIG. 12A FIG. 12E

CHARACTERIZATION OF LESIONS VIA DETERMINATION OF VASCULAR METRICS USING MRI DATA

CROSS-REFERENCE TO RELATED APPLICATION

This application is a U.S. National Phase Application under 35 U.S.C. § 371 of International Application No. PCT/US2020/054127, filed Oct. 2, 2020, which claims priority to U.S. Provisional Application Ser. No. 62/910,286, filed Oct. 3, 2019, each of which is incorporated herein by reference in its entirety.

STATEMENT REGARDING FEDERALLY SPONSORED RESEARCH

This invention was made with government support under Grant numbers U01 CA174706, R01 CA218700, U01 CA142565, and R01 CA172801 awarded by the National Institutes of Health, and Grant number DMS1654076 awarded by the National Science Foundation. The government has certain rights in the invention.

FIELD OF THE DISCLOSURE

This disclosure relates generally to characterization of potentially cancerous lesions using vascular metrics, to use of morphological and functional information on tumor-associated blood vessels gained through analysis of magnetic resonance imaging (MRI) data in characterization and treatment of suspicious lesions, and to use of MRI data to constrain a patient-specific, computational fluid dynamics (CFD) model of blood flow and interstitial transport in characterization of cancers.

BACKGROUND

Understanding the vascular features of tissues can be useful in the clinical setting, but conventional approaches are invasive, lack the desired sensitivity, and are limited to surface vessels.

SUMMARY

Various embodiments relate to a method of non-invasively characterizing a tumor in a ROI based on tumor hemodynamics determined using MRI data. The method may comprise acquiring MRI data of a ROI. The MRI data may comprise a first MRI dataset corresponding to high spatial resolution dynamic contrast enhanced MRI (DCE-MRI) scans of the ROI. The MRI data may comprise a second MRI dataset corresponding to high temporal resolution DCE-MRI scans of the ROI. The MRI data may comprise a third MRI dataset corresponding to diffusion-weighted MRI (DW-MRI) scans of the ROI. The method may comprise determining vasculature metrics using the first MRI dataset, the second MRI dataset, and the third MRI dataset. The method may comprise determining at least one of tumor-associated blood flow velocity or tumor interstitial pressure by using the vasculature metrics as inputs to a computational fluid dynamics model. The method may comprise generating at least one tumor characteristic based on determining the at least one of tumor-associated blood flow velocity and tumor interstitial pressure. Tumor characteristics may be generated using blood flow velocity and/or tumor interstitial pressure.

Various embodiments relate to a method of non-invasively characterizing a tumor by mapping pressure and flow fields in a ROI using quantitative MRI data. The method may comprise acquiring MRI data comprising DCE-MRI scans of the ROI and DW-MRI scans of the ROI. The method may comprise dividing the ROI into a vascular space and an interstitial space by segmenting the MRI data. The vascular space may comprise a blood vessel network. The interstitial space may comprise interstitial tissue. The method may comprise assigning corresponding material properties to the vascular space and the interstitial space via analysis of MRI data corresponding to both the DCE-MRI and DW-MRI scans. The method may comprise applying a computational fluid dynamics model to determine hemodynamics related metrics of a tumor in the ROI. The method may comprise generating an indication of malignancy of the tumor based on the hemodynamics related metrics of the tumor.

Various embodiments of the disclosure relate to a method of non-invasively characterizing a tumor in a region of interest (ROI). The method may comprise acquiring a first magnetic resonance imaging (MRI) dataset corresponding to high spatial resolution scans of the ROI, and a second MRI dataset corresponding to high temporal resolution scans of the ROI. The scans of the first and second MRI datasets at least partially overlap in time. The method may comprise determining at least one morphological vascular metric using the first MRI dataset. The method may comprise determining at least one functional vascular metric using the second MRI dataset. The method may comprise generating at least one tumor characteristic based on both of the at least one morphological metric and the at least one functional metric.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

FIGS. 4A-4I illustrate vessel segmentation and tumor-associated vessel detection. FIG. 4A depicts intensity histogram for 1 slice of 1 patient's subtraction image. FIG. 4B depicts intensity transfer function (Equation 1) for this slice, where the inflection point is given by the value obtained by the 95th percentile from FIG. 4A. FIG. 4C depicts the 3 types of local structure and the corresponding features of the Hessian matrix eigenvalues. The conceptual 2D illustration of vessel segmentation is displayed in FIG. 4D input image, FIG. 4E vesselness map, and FIG. 4F segmented vessels and graph analysis. FIGS. 4G, 4H, and 4I illustrate an example tumor-associated vessel detection process through the tensor-voting FIG. 4G and cost-map FIG. 4H, which yield the identified tumor-associated vessels.

FIGS. 5A-5D depict bolus arrival-time estimate and pharmacokinetic modeling, according to potential embodiments.

FIG. 5A depicts internal thoracic arteries on a transverse, post-contrast slice (about 15 seconds after contrast agent injection) in one patient. A half-logistic function (Equation 6) is fit to the time course to estimate the bolus arrival time FIG. 5B. The population arterial input function (AIF) is then aligned using the delay of the estimated arrival time for each voxel compared to the enhancement time of the population AIF at FIG. 5C. FIG. 5D depicts results of pharmacokinetic modeling, with each row presenting one representative patient. From left to right in FIG. 5D, columns show model fitting in an example voxel and the corresponding parametric maps, $K^{trans}$, $v_p$, arrival-time.

FIGS. 6A and 6B depict maximum intensity projection (MIP) of the whole breast subtraction images. After enhancing by the S-shaped intensity transformation and applying the Hessian-based filter, the images are then segmented and each voxel is assigned "vesselness" value as in FIGS. 6C and 6D that can then be rendered in 3D in the same image space as the segmented lesions of FIGS. 6E and 6F. FIGS. 6G and 6H depict the 3D reconstruction of the vessel tree and the identified tumor-associated vessels. Red arrows represent vessels that could be mistakenly identified as tumor-associated vessels if only using the MIP.

FIG. 10A illustrates the vessel skeleton after smoothing (red curve), the original segmented vessel mask (blue blocks), and $v_p$ values in corresponding voxels (yellow numbers) on a region containing a vessel (pink tube). The structures are up-sampled (green) in FIG. 10B. FIG. 10C indicates the neighborhood (deep blue blocks) identified with the local orientation of a vessel (v) and a predetermined step width (dl). FIG. 10D indicates the vessel radius (R) calculated using Equation (24) and the re-scaled vessel region mask (red blocks). FIG. 10E shows the process going through the whole vessel. FIG. 10F shows the result of vessel mask scaling (red blocks), which is compared with the original mask (baby blue blocks).

FIGS. 11A-11J depict image analysis for malignant (FIGS. 11A-11E) and benign (FIGS. 11F-11J) tumors, in potential embodiments. FIGS. 11A and 11F show the whole breast vasculature centerlines after smoothing and gap filling (black curves), on the segmented tumor lesions (gray volumes), and detected tumor-associated vessels (red curves for inlets and blue curves for outlets). FIGS. 11B and 11G depict the measured BAT map in the tumor and vessel regions on the central slice of tumor, overlaid on the post-contrast anatomical image. FIGS. 11C and 11H present the fitted $v_p$ map. FIGS. 11D and 11I show the $K^{trans}$ map. FIGS. 11E and 11J show ADC map after modification using an example method discussed herein in the context of segmentation and vessel detection in processing of quantitative MRI data. FIGS. 11A-11J depict a malignant lesion with more tumor-associated vessels, larger $v_p$, larger $K^{trans}$, and an earlier BAT compared to the benign lesion.

FIGS. 12A-12H depict generation of meshes representing vasculature-interstitium geometry and assignment of spatial-resolved material properties for the malignant (FIGS. 12A-12D) and benign (FIGS. 12E-12H) tumors, according to various embodiments. FIGS. 12A and 12E present reconstructed vascular meshes (white volume) within the tumor region presented as purple, semi-translucent volumes. FIGS. 12B and 12F show the meshes of the interstitial tissue, where enlarged views show bifurcations of the excluded vessel region. FIGS. 12C and 12G map the vascular permeability ($L_p$) to the vessel meshes which is calibrated from $K^{trans}$. FIGS. 12D and 12H assign the tissue hydraulic conductivity ($\kappa$) to the tissue meshes as calibrated from the ADC.

FIG. 13A depicts an optimization object (M) plot over the simulated annealing process. FIG. 13B compares the distribution of estimated (orange bars) and measured (blue bars) BAT values over the whole breast. FIG. 13C displays the measured (left) and estimated (right) BAT onto whole breast vasculature for visualization.

FIGS. 14A and 14E present the blood pressure along the whole vascular network, with the tumor region presented as semi-translucent volumes. FIGS. 14B and 14F depict the interstitial pressure in whole breast tissue, with the tumor region presented as well. FIGS. 14C and 14G show the interstitial pressure on the tumor surface. FIGS. 14D and 14H visualize the vector fields of interstitial flow velocity in the tumors, with the tumor volume presented as semi-translucent. Both the size and color of the arrows represent the magnitude of local velocity. The visualization demonstrates that the malignant lesion has higher and more heterogeneous interstitial pressure and interstitial flow velocity than the benign lesion.

Figure 1:
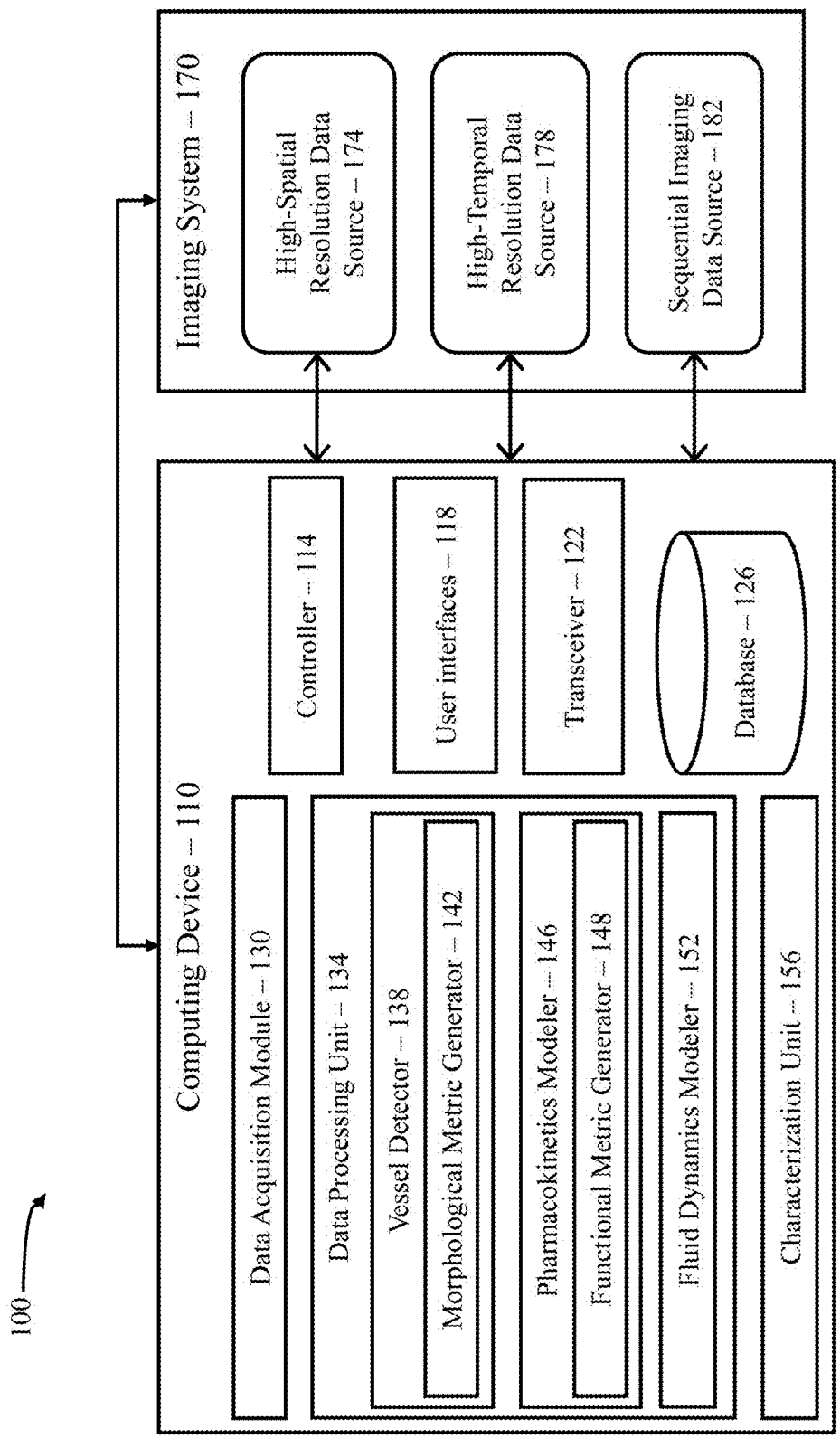
FIG. 1 depicts an example system for implementing disclosed approaches for characterizing physiological structures, according to potential embodiments.

The foregoing and other features of the present disclosure will become apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, may be arranged, substituted, combined, and designed in a wide variety of different configurations, all of which are explicitly contemplated and make part of this disclosure.

Dynamic contrast enhanced magnetic resonance imaging (DCE-MRI) involves the serial acquisition of heavily $T_1$-weighted images acquired before, during, and after the injection of a paramagnetic contrast agent. Both semi-quantitative and quantitative analysis of DCE-MRI have been shown to provide important insights in both the diagnostic and prognostic settings for breast cancer. Within the diagnostic setting, the sensitivity of DCE-MRI has been reported as 88% to 100% but with a variable specificity of 63% to 96%. Therefore, it is of great importance to develop new MRI acquisition and analysis methods that can yield improved biomarkers with higher specificity for the diagnosis of suspicious lesions. Intimately related to this problem is the issue of balancing the competing acquisition demands of obtaining data acquired at both high spatial and high-temporal resolution.

In the standard-of-care setting, great emphasis is placed on collecting DCE-MRI data at very high spatial resolution, thereby necessitating low temporal resolution (e.g., 60-120 seconds). Use of high spatial resolution data for characterization of vascular features has been focused on manual evaluation of ipsilateral breast vascularity, bilateral symmetry, and vessels adjacent to the suspicious lesion. Importantly, the majority of the current literature on the topic uses analysis of maximum intensity projections. This naturally eliminates information describing the vascular structure in 3D and may even be misleading by suggesting certain vessels are in contact with the lesion itself. Although high spatial resolution can aid in the characterization of morphology, it precludes accurate quantification of pharmacokinetic parameters that are important indicators of malignancy and does not allow tracking of the contrast media bolus as it propagates through arteries and veins.

Moreover, tumor initiation, growth, and invasion is tightly coupled to the characteristics of the available blood supply. Additionally, interstitial flow within the tumor microenvironment determines access to nutrition, oxygen, and therapies for cells not immediately adjacent to vessels. Both mechanisms contribute to heterogeneous delivery of therapeutics, leading to substantial variations of treatment response between patients. Increased interstitial flow also stimulates increased tumor cell migration and motility by activating cell surface receptors interacting with chemokines and the extracellular matrix. Interstitial flow can exert a shear stress on tumor cells, resulting in G2/M arrest and inhibition of differentiation. Interstitial fluid pressure also serves to activate tumor stroma and fibroblasts, and even increases angiogenesis. Thus, being able to rigorously characterize, in vivo, tumor-associated hemodynamics and interstitial transport is of great importance for quantifying several fundamental aspects of the underlying biology of cancer.

Prior approaches to determining a tumor's blood supply are invasive nature and/or unable to interrogate deep tissues. Measurement of the interstitial environment is even more challenging. For example, using needle-based assessments, interstitial fluid pressure in malignant breast tumors has been found to be much higher than in benign or healthy conditions. However, this measurement is invasive, has limiting sampling, and therefore cannot characterize any spatial heterogeneity that may exist. Other efforts at characterizing tumor related blood flow rely on segmenting vascular structures from ex vivo imaging data. This limits its utility for diagnosis or prognosis, because it 1) requires an invasive procedure that damages the system under investigation, and 2) provides limited information on the remaining lesion or host tissue. Further, using predetermined constant values (population values) for material properties (e.g., vascular permeability and tissue hydraulic conductivity) cannot capture inter- or intra-patient heterogeneity. Prior approaches are not patient-specific and clinically feasible.

Disclosed are various embodiments of an approach that may combine vessel detection with analysis of ultrafast dynamic contrast enhanced magnetic resonance imaging (DCE-MRI) data to integrate both morphological and functional information of tumor-associated vessels to assist in the characterization and treatment of suspicious breast lesions. In various embodiments, high spatial resolution data is used to automatically (1) segment the breast vasculature in 3D, (2) identify and count individual tumor feeding and draining vessels, and (3) compute vessel number and tortuosity. Such methods can, in various embodiments, be integrated with kinetic parameters available from ultra-fast DCE-MRI data analysis and a logistic ridge regression model to provide a more complete characterization of lesions in the diagnostic and treatment setting.

Also disclosed are various embodiments of a computational fluid dynamics (CFD) analysis of quantitative MRI data to characterize the hemodynamics of cancer on a patient-specific basis, an approach that improves diagnostic accuracy and enhances therapeutic planning, thereby improving cancer treatment. A more rigorous understanding of flow through tumor-associated vessels and its interaction with the surrounding interstitium provides critical insights into diagnosis, delivery of therapy, and assessment and prediction of the response of tumors to treatment. Pressure and flow fields within a ROI (e.g., the breast) can be mapped using noninvasive methods and patient specific data.

In various embodiments, high temporal resolution (e.g., ultrafast) and high spatial resolution DCE-MRI data may be acquired on patients with suspicious lesions. Segmentation of the vasculature from the surrounding tissue may be performed by, for example, applying a Hessian filter to the enhanced image to generate a map of the probability for each voxel to belong to a vessel. Summary measures may be generated for vascular morphology, as well as the inputs and outputs of vessels physically connected to the tumor. The ultrafast DCE-MRI data may be analyzed by, for example, a modified Tofts model to estimate, for example, the bolus arrival time, $K^{trans}$ (volume transfer coefficient), and $v_p$ (plasma volume fraction). Vessel count, $K^{trans}$, and/or $v_p$, which are significantly different in malignant versus benign lesions, may be metrics used to characterize lesions in ROIs.

In some embodiments, differentiation between malignant and benign lesions may use vessel count and bolus arrival time. Combining quantitative characterization of morphological and functional features of vasculature may be used in better characterizing and treating cancer in patients.

In various embodiments, MRI data may be used to constrain a patient-specific, computational fluid dynamics (CFD) model of blood flow and interstitial transport in cancer. Disclosed are example embodiments of an image processing approach to generating tumor-related vasculature-interstitium geometry and realistic material properties using DCE-MRI and diffusion weighted MRI (DW-MRI) data. These data may be used to constrain CFD simulations for determining tumor-associated blood supply and interstitial transport characteristics unique to each patient. Interstitial pressure and magnitude of interstitial flow velocity vary significantly between malignant and benign lesions, and one or both can be used, for example, in characterizing whether a tumor is malignant or benign. Vascular characteristics of extraction rate of and blood flow rate also vary significantly and one or both can alternatively or additionally be used, for example, to determine whether a lesion is malignant or benign. In various embodiments, an image-based model system allows for the mapping of flow and pressure fields related to tumors using only non-invasive, clinically available imaging data and fluid mechanics, and may be used for quantitative characterization of cancer.

Referring to FIG. 1, in various embodiments, a system 100 may include a computing device 110 (or multiple computing devices, co-located or remote to each other) capable of communicating with an imaging system 170, which may include, for example, an MRI scanner and/or other imaging devices and sensors. The computing device 110 may include a controller 114 that is configured to exchange control signals with imaging system 170 (or components thereof), allowing the computing device 110 to be used to control the capture of images and/or signals via sensors of the imaging system 170, retrieve imaging data or signals, direct analysis of the data and signals, and output analysis results. The controller 114 may include one or more processors and one or more volatile and non-volatile memories for storing computing code and data that are captured, acquired, recorded, and/or generated.

One or more user interfaces 118 allow the computing device 110 to receive user inputs (e.g., via a keyboard, touchscreen, microphone, camera, etc.) and provide outputs (e.g., via a display screen, audio speakers, etc.). A transceiver 122 allows the computing device 110 to exchange readings, control commands, and/or other data with imaging system 170 or components thereof, or with other systems and devices. The computing device 110 may additionally include one or more databases 126 for storing, for example, data or signals acquired via one or more imagers or other sensors. In some implementations, database 126 (or portions thereof) may alternatively or additionally be part of another computing device (that is co-located or remote and in communication with computing device 110) and/or of imaging system 170.

Computing device 110 may include a data acquisition module 130 that acquires images or signals (collectively, imaging data) via imaging system 170. In certain embodiments, data acquisition module 130 may access imaging data, acquired through past scans, from database 126 or another system or device. The data acquisition module 130 may, in some embodiments, request and receive particular imaging data from the imaging system 170, or may receive all imaging data from imaging system 170 and identify particular subsets thereof that are to be used for various analyses. In some embodiments, data acquisition module 130 may control or direct imagers and/or sensors of imaging system 170 to capture various images or signals, or may direct components of imaging system 170 to provide certain raw or processed data.

A data processing unit 134 may receive imaging data from data acquisition module 130 and analyze the imaging data. The data received from data acquisition module 130 may be raw or processed. Data processing unit 134 may analyze imaging data to, for example identify physiological characteristics or metrics (e.g., vasculature metrics) in a region of interest (ROI), such as a breast or other region of a patient, that is imaged using imaging system 170. The data processing unit 134 may include a vessel detector configured to, for example, identify blood vessels in MRI data, whether blood vessels are associated with a tumor (e.g., connecting to or exchanging blood with the tumor), etc. The vessel detector 138 may include a morphological metric generator 142 which identifies structural characteristics of vessels in the ROI.

The computing device 110 may include a pharmacokinetics modeler 146 for characterizing blood flood in the ROI. The pharmacokinetics modeler 146 may, for example, obtain data related to contrast media bolus as it propagates through arteries and veins. The pharmacokinetics modeler 146 may include a functional metric generator 148 which determines metrics related to circulation such as $K^{trans}$ (volume transfer coefficient) and $v_p$ (plasma volume fraction). Fluid dynamics modeler 152 may apply computational fluid dynamics models to metrics determined from MRI data. For example, fluid dynamics modeler 152 may apply fluid dynamics to obtain metrics, such as blood flow velocity and/or tumor interstitial pressure, useful in characterizing a lesion. Characterization unit 156 may determine characteristics of a lesion based on analysis of MRI data. For example, characterization unit 156 may receive morphological and functional metrics from vessel detector 138 and pharmacokinetics modeler 146, and/or metrics from fluid dynamics modeler 152, to evaluate whether a lesion is malignant, available treatment protocols, etc.

The imaging system 170 may include a high-spatial resolution data source 174 that acquires or otherwise provides high-spatial resolution imaging data (such as high-spatial resolution dynamic contrast enhanced magnetic resonance imaging (DCE-MRI) data), a high-temporal resolution data source 178 that acquires or otherwise provides high-temporal resolution data (such as fast or ultrafast DCE-MRI data), and a sequential imaging data source 182 that acquires or otherwise provides data based on sequential images (such as diffusion-weighted MRI (DW-MRI) data) which may be used to track, for example, Brownian or other motion in a region of interest. In various implementations, the high-spatial resolution data source 174, high-temporal resolution data source 178, and sequential imaging data source 182 may be part of one MRI system, may be split into separate components (connected to one or more MRI scanners, or part of one or more MRI systems), or may otherwise have different configurations than those depicted in FIG. 1.

In various embodiments, high temporal resolution scans (used interchangeably with "ultrafast" scans) have a temporal resolution that is less than 30 seconds. In certain embodiments, high temporal resolution scans have a temporal resolution that is less than 10 seconds. In certain embodiments, ultrafast scans have a temporal resolution that is less than 5 seconds. In certain embodiments, ultrafast scans have a temporal resolution that is less than 4 seconds. In some embodiments, ultrafast scans have a temporal resolution that is less than 3 seconds. In some embodiments, ultrafast scans have a temporal resolution that is less than 2 seconds. In some embodiments, ultrafast scans have a temporal resolution that is less than 1 second. In some embodiments, ultrafast scans have a temporal resolution that is between 0.5 seconds to 1 second.

In various embodiments, high spatial resolution scans have a spatial resolution spatial resolutions less than 5 cubic millimeters. In certain embodiments, high spatial resolution scans have spatial resolutions less than 4 cubic millimeters. In certain embodiments, high spatial resolution scans have spatial resolutions less than three cubic millimeters. In certain embodiments, high spatial resolution scans have spatial resolutions less than two cubic millimeters. In some embodiments, high spatial resolution scans have spatial resolutions less than one cubic millimeter.

Figure 2A:
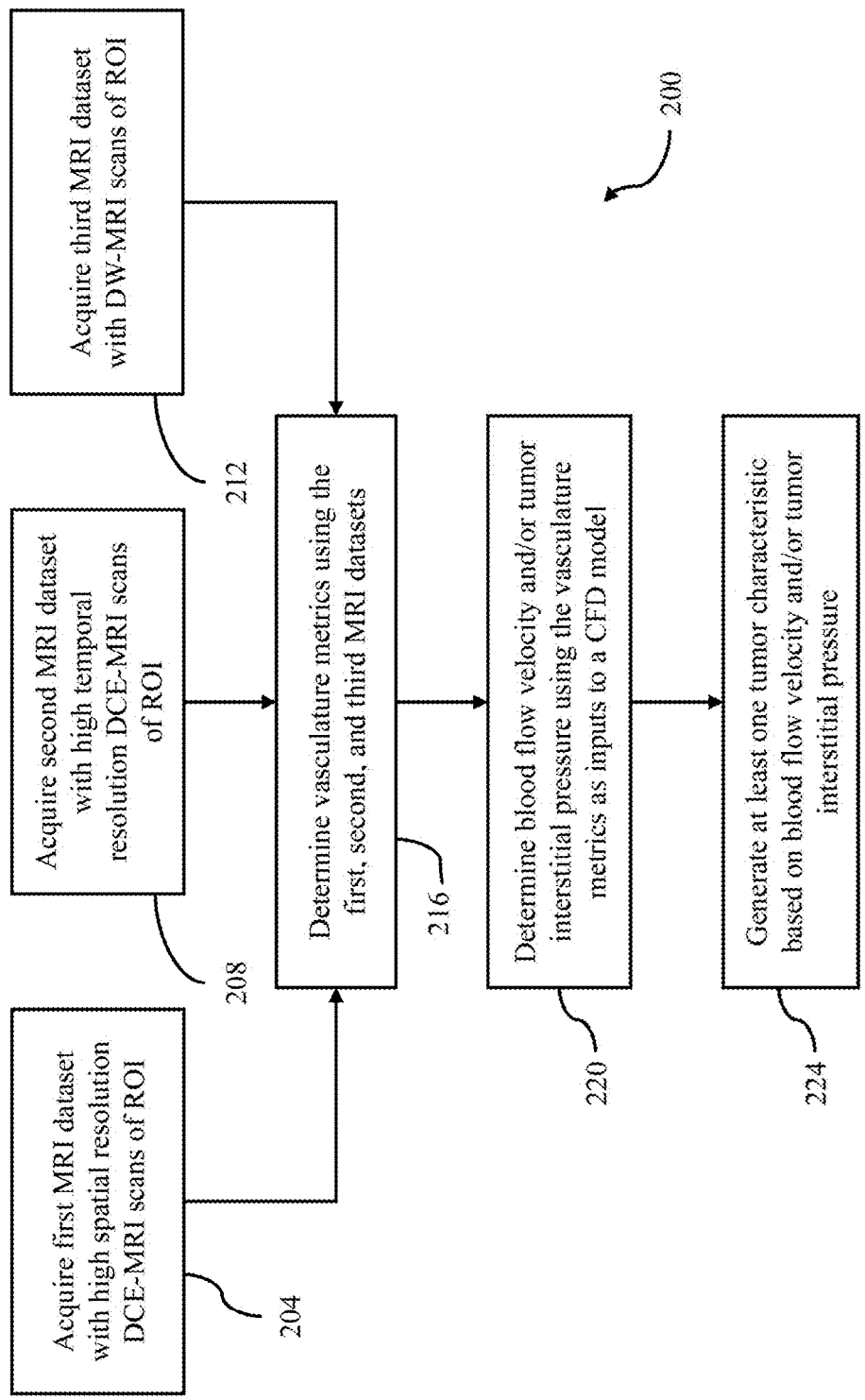
FIGS. 2A-2C depict example flowcharts describing operations applied to the data, according to potential embodiments.

Referring to FIG. 2A, an example process 200 for non-invasively characterizing a tumor in a region of interest (ROI) is provided, according to various potential embodiments. The tumor may be characterized based on tumor hemodynamics determined using magnetic resonance imaging (MRI) data. At 204, a first MRI dataset with high spatial resolution DCE-MRI data of the ROI is acquired. In potential implementations, the first MRI dataset may be acquired from imaging system 170, or high-spatial resolution data source 174, by data acquisition module 130. At 208, a second MRI dataset with high temporal resolution DCE-MRI data of the ROI is acquired. In potential implementations, the second MRI dataset may be acquired from imaging system 170, or high-temporal resolution data source 178, by data acquisition module 130. At 212, a third MRI dataset with DW-MRI data of the ROI is acquired. In potential implementations, the third MRI dataset may be acquired from imaging system 170, or sequential imaging data source 182, by data acquisition module 130.

At 216, the first, second, and third MRI datasets may be used to determine vasculature metrics. The vasculature metrics may be determined via data processing unit 134 using data from data acquisition module 130, in potential implementations. Vessels may be identified and their structure determined by vessel detector 138, and flow of blood may be characterized using pharmacokinetics modeler 146, in various implementations. For example, the morphological metric generator 142 may use the MRI datasets to determine morphological metrics, and the functional metric generator 148 may determine functional metrics. At 220, blood flow velocity and/or tumor interstitial pressure may be determined using the vasculature metrics. The blood flow velocity and/or tumor interstitial pressure may be determined by applying a computational fluid dynamics (CFD) model to the vasculature metrics. In various implementations, the fluid dynamics modeler 152 may receive vasculature metrics from vessel detector 138 and pharmacokinetics modeler 146 and apply the CFD model to obtain blood flow velocity and/or interstitial pressure. At 224, at least one characteristic of the tumor may be determined based on, for example, blood velocity and/or on tumor interstitial pressure. In potential implementations, the characterization unit 156 may determine the characteristic(s) of the tumor using data from the fluid dynamics modeler 152.

Figure 2B:
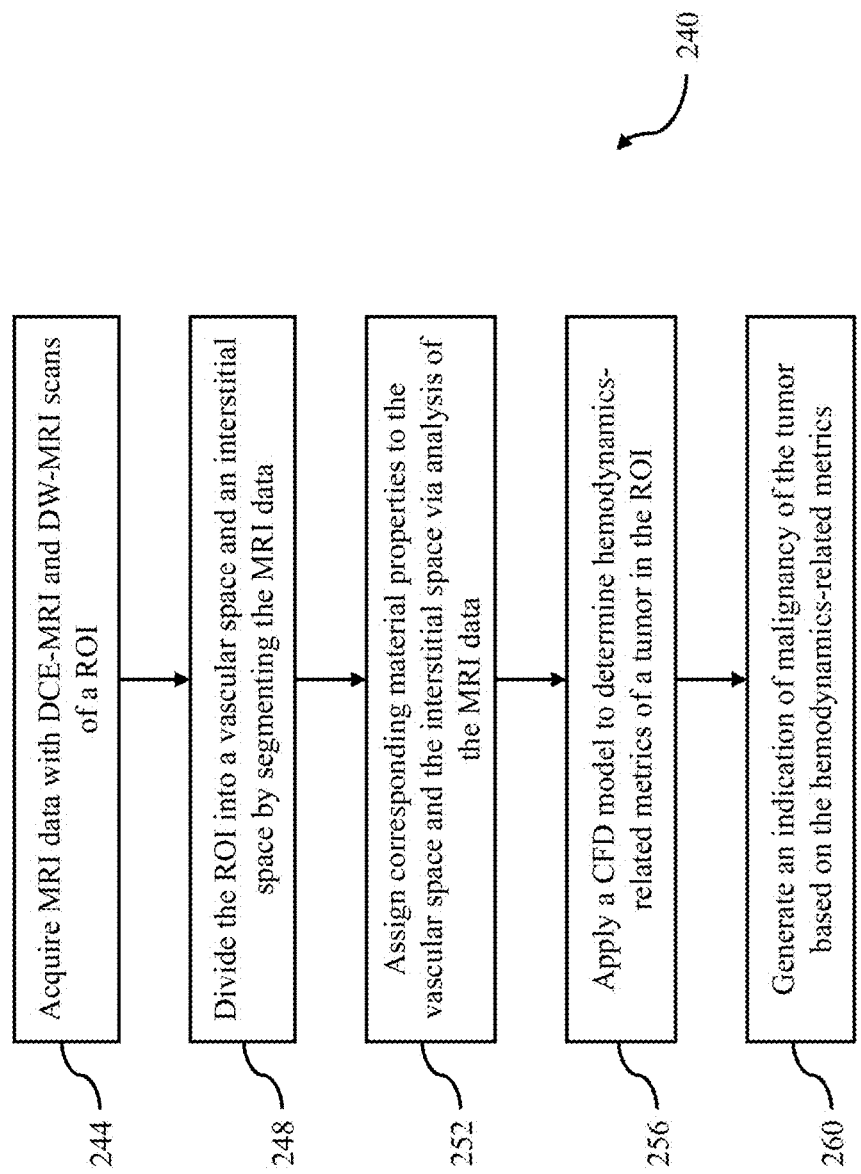

Referring to FIG. 2B, an example process 240 for non-invasively characterizing a tumor by mapping pressure and flow fields in a ROI using MRI data is provided, according to various potential embodiments. At 244, MRI data with both DCE-MRI and DW-MRI scans of a ROI may be acquired. The MRI data may be acquired by data acquisition module 130 from imaging system 170, in potential implementations. At 248, the ROI may be divided into a vascular space and an interstitial space by segmenting the MRI data. In various implementations, the MRI data may be segmented by data processing unit 134 to obtain the vascular and interstitial spaces. Segmenting of the MRI data may involve data on vessel morphology from vessel detector 138 and pharmacokinetics modeler 146. At 252, corresponding material properties may be assigned to the vascular and interstitial spaces via analysis of the MRI data. The material properties may be assigned via, for example, vessel detector 138 and pharmacokinetics modeler 146, in potential implementations. At 256, a CFD model may be applied to determine hemodynamics-related metrics of a tumor or other lesion in the ROI. In potential implementations, the fluid dynamics modeler 152 may apply the CFD model to determine one or more hemodynamics-related metrics. At 260, an indication of malignancy of the tumor may be generated based on the hemodynamics-related metrics. In potential embodiments, the characterization unit 156 may generate the indication of malignancy of the tumor using hemodynamics-related metrics obtained via vessel detector 138 and/or pharmacokinetics modeler 146.

Figure 2C:
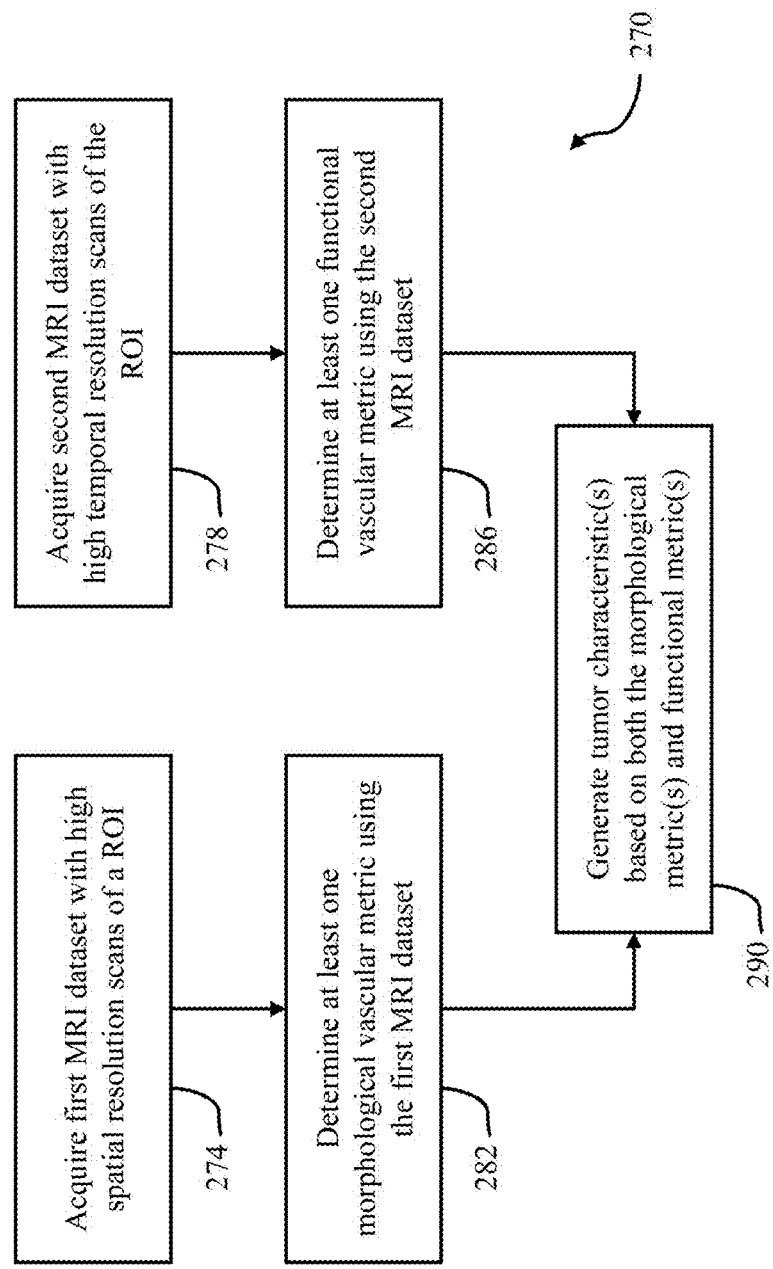

Referring to FIG. 2C, an example process 270 for non-invasively characterizing a tumor in a ROI is provided, according to various potential embodiments. At 274 and 278, first and second MRI datasets with high spatial resolution scans of the ROI and high temporal resolution scans of the ROI, respectively, may be acquired. In various embodiments, data acquisition module 130 may acquire the first MRI dataset at 274, and data acquisition module 130 may acquire the second MRI dataset at 278. In potential implementations, the data acquisition module 130 may acquire the first MRI dataset from high-spatial resolution data source 174 and the second MRI dataset from the high-temporal resolution data source 178. At 282, at least one morphological vascular metric is determined using the first MRI dataset. The morphological vascular metric may be determined via the morphological metric generator 142 in potential embodiments. At 286, at least one functional vascular metric is determined using the second MRI dataset. The functional vascular metric may be determined via the functional metric generator 148 in potential embodiments. At 290, the morphological and functional vascular metric(s) may be used to generate a tumor characteristic. The characterization unit 156 may, in potential implementations, determine one or more tumor characteristics using morphological and functional vascular metrics obtained via, for example, the morphological metric generator 142 and the functional metric generator 148, respectively.

Figure 3:
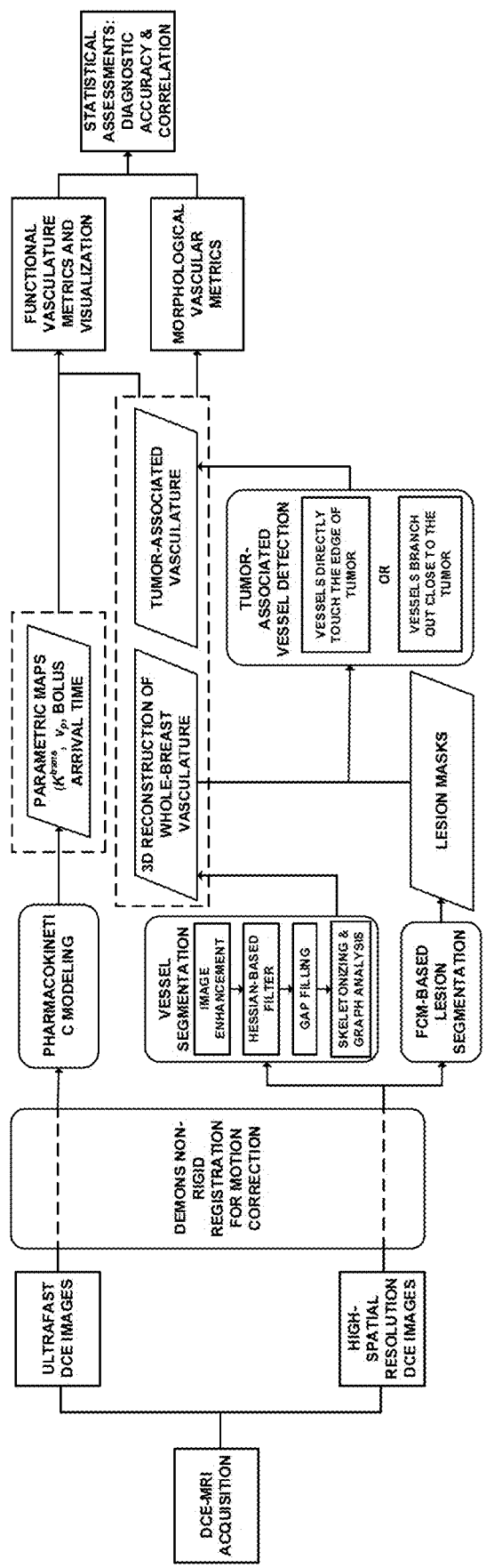
FIG. 3 depicts an example flow chart describing operations applied to the data, according to potential embodiments.

FIG. 3 provides an example flowchart for operations applied to MRI data from a breast to non-invasively characterize a lesion in the breast using morphological and functional vascular metrics, according to potential embodiments. As overview, both high temporal resolution ("ultrafast") and high spatial resolution DCE images may be registered for motion correction and used as inputs of downstream processing. Lesions may be segmented using high spatial resolution DCE series with, for example, a fuzzy c-means-based (FCM-based) algorithm. Whole-breast vasculature segmentation may be performed on a subtraction of pre-contrast high spatial images from first frame of post-contrast images. Tumor-associated vessels may be identified via spatial overlapping or tracking. The ultrafast DCE series may be used for pharmacokinetic modeling to generate parametric maps of $K^{trans}$ and $v_p$, as well as bolus arrival time. The identified vessels and estimated parameters may be integrated to generate metrics representing morphological or functional features of tumor microcirculation. Statistical analyses were performed to assess the diagnostic performance for these metrics to discriminate malignant or benign lesions.

In a demonstrative implementation, 15 women with Breast Imaging Reporting and Data System (BI-RADS) 4 or 5 lesions identified on screening mammography, and with category C or D breast density, received a research MRI before biopsy. The 15 women (median age=57, range=27-75) were divided into 2 groups, group A (N=9) and group B (N=6), because of different image acquisition protocols (discussed below). All patients underwent image-guided biopsies after research MRIs, biopsy results were used as the ground truth, except for 2 lesions that were determined to be benign with follow-up imaging. In total, 13 distinct malignant and 11 benign lesions were identified. The malignant lesions included 1 invasive lobular carcinoma (ILC), 6 invasive ductal carcinoma (IDC), and 3 ductal carcinoma in situ (DCIS). The benign imaging findings included radial scar, phyllodes tumor, cystic papillary apocrine metaplasia, fibroadenomas, palliloma, and atypical ductal hyperplasia. The patients included in the study were evaluated as high probability for malignancy by clinical assessment (i.e., BI-RADS 4-suspicious or 5-highly suggestive of malignancy; see Table 1), indicating inherent difficulty in discriminating malignant from benign lesions on clinical assessment.

TABLE 1

Patients and lesions characteristics (15 patients, 24 lesions)

| Characteristic | N (%) | Median (range) |
|---|---|---|
| Patient age (y) | | 57 (27-75) |
| Lesion size (mm) | | 24 (5-111) |
| Histopathology | | |
| Benign | 11 (46) | |
| Malignant | 13 (54) | |
| (DCIS, invasive) | | |
| Lesion type | | |
| Mass | 13 (54) | |
| Nonmass | 11 (46) | |
| Detectable by Palpation | 1 (4) | |
| Ultrasound | 18 (90) | |
| | (4 did not undergo US) | |
| Mammography | 18 (75) | |
| Clinical assessment | | |
| 4-Suspicious | 10 (67) | |
| 5-Highly suggestive of malignancy | 5 (33) | |

Abbreviations: DCIS, ductal carcinoma in situ; US, ultrasound

Images were acquired on a Philips Achieva 3T-TX (Best, Netherlands) with a 16-channel bilateral breast coil and a 3D spoiled gradient recalled echo protocol. For group A, 2 types of dynamic data were acquired: fat-suppressed ultrafast DCE-MRI with temporal resolutions between 3.4-4.1 seconds (s), spatial resolution of 1.5×1.5×4 cubic millimeters ($mm^3$) with a SENSE factor of 4 in the right-left direction and 2 in the foot-head direction, and partial Fourier factor of 0.7 (in both $k_y$ and $k_z$), and fat-suppressed high spatial resolution scans, with a temporal resolution of 55-63 s and a spatial resolution of 0.8×0.8×1.6 $mm^3$, SENSE of 2.5 in right-left direction, and partial Fourier of 0.85 in $k_y$. The order of acquisition before the injection of 0.1 mM/kg MultiHance (Bracco, Milan, Italy) at 2 mL/s may be, for example, 1 pre-contrast high spatial resolution scan and then 5 pre-contrast ultrafast scans. The post-contrast acquisition consisted of 19 ultrafast scans and then 4 post-contrast high spatial resolution scans (see Table 2 for details on MRI scan parameters). It is noted that the descriptor "fast" was first associated with post-contrast subtracted images in abbreviated MR protocols acquired at temporal resolutions ranging from 60-120 s. To avoid confusion with these protocols, the term "ultrafast" has been used for any protocols that have temporal resolutions higher than those used in routine clinical protocols.

TABLE 2

MRI scan parameters

| MRI parameters | $T_1$-mapping | Ultrafast DCE-MRI | Fast DCE-MRI | High spatial resolution DCE-MRI |
|---|---|---|---|---|
| Scan sequence | spoiled GRE | spoiled GRE | spoiled GRE | spoiled GRE |
| Time (s) | 80/160 | group A: 90 group B: 42 | 80 | 340 |
| TR (ms) | 10 | 3.2 | 3.2 | 5.0 |
| TE (ms) | 2.4 | 1.6 | 1.6 | 2.5 |
| Flip angle(s) (°) | 5, 10, 15, 20 | 10 | 10 | 10 |
| Acquisition matrix | 340 340 | 228 154 | 228 228 | 425 425 |
| Slice thickness (mm) | 1.6 | 4 | 3 | 1.6 |
| Slice spacing (mm) | 0.8 | 2 | 1.5 | 0.8 |
| Temporal resolution (s) | 40 | Group A: 3.4-4.1 Group B: 1.7-3.5 | 6.2-7.1 | 65 |

Abbreviation: GRE, gradient recalled echo sequence

The lesions were segmented from the surrounding breast tissue on the registered high spatial resolution DCE-MIRI data using a fuzzy c-means-based (FCM) method.

Figure 4I:
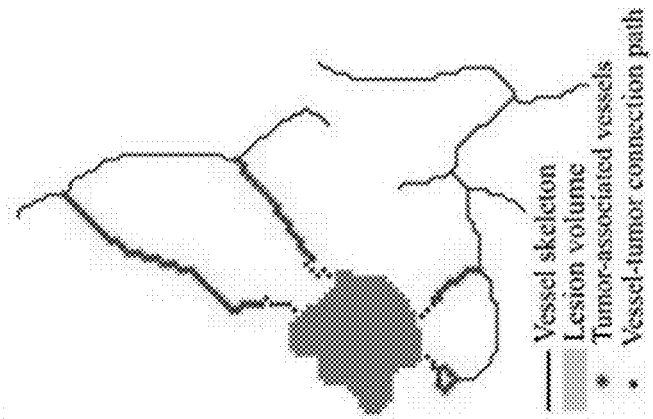
Figure 4H:
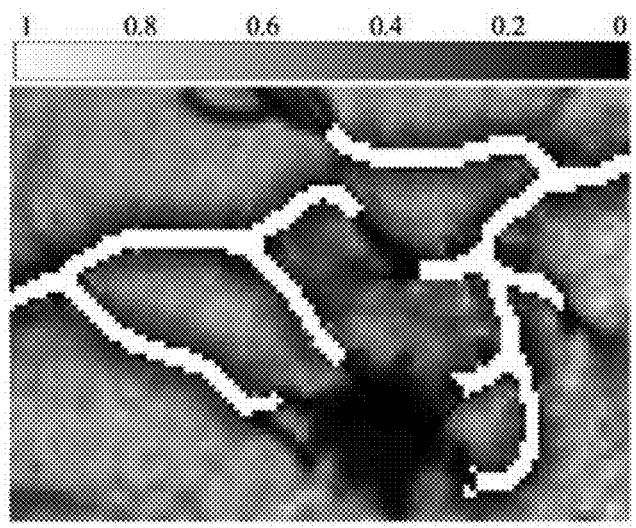

With respect to image enhancement, before vessel segmentation, a local-statistics-based intensity transfer function may be applied on the subtraction of the pre-contrast from the post-contrast, high spatial resolution images for histogram normalization and enhancement. For each slice, an S-shaped transfer function given by Equation 1 may be applied so that foreground enhancement as well as background suppression could be achieved simultaneously, $$I_{enh} = \begin{cases} I_c - \sqrt{I_c^2 - I_{orig}^2}, & 0 < X \leq X_c \\ I_c + \sqrt{(I_{max} - I_c)^2 - (I_{max} - I_{orig})^2}, & X_c < X \leq X_{max} \end{cases} \quad (1)$$

where $I_{org}$, $I_{max}$, and $I_{enh}$ are the original subtraction image, maximal intensity in the original image, the enhanced image, respectively, and $I_c$ is the inflection point of the S-shaped transfer function, set to be the 95$^{th}$ percentile of the intensity histogram (see FIGS. 4A and 4B, for example).

With respect to multiscale Hessian matrix based vessel segmentation and post-processing, segmentation of the vasculature from the surrounding tissue may be performed on the enhanced, high-resolution, subtraction images. A multiscale Hessian-based filter may first be applied to generate a map of "vesselness," which represents the probability for each voxel to contain a vessel. For an image, I, the Hessian matrix describes the second-order derivatives of intensity around each point in I (Equation 2), $$H = \begin{pmatrix} \frac{\partial^2 I}{\partial x^2} & \frac{\partial^2 I}{\partial_x \partial_y} & \frac{\partial^2 I}{\partial_x \partial_y} \\ \frac{\partial^2 I}{\partial_y \partial_x} & \frac{\partial^2 I}{\partial_y^2} & \frac{\partial^2 I}{\partial_y \partial_z} \\ \frac{\partial^2 I}{\partial_z \partial_x} & \frac{\partial^2 I}{\partial_z \partial_y} & \frac{\partial^2 I}{\partial_z^2} \end{pmatrix} \quad (2)$$

where x, y, and z are the canonical Cartesian axes. If we set the eigenvalues of the Hessian matrix to be sorted as $|\lambda_1| \leq |\lambda_2| \leq |A_3|$, the Hessian-based vascular filter is given by Equation 3, $$f(\sigma) = \begin{cases} 0, & \text{if } \lambda_2 > 0 \text{ or } \lambda_3 > 0 \\ \left(1 - e^{-\frac{R_A^2}{2\alpha^2}} \cdot e^{-\frac{R_B^2}{2\beta^2}} \cdot \left(1 - e^{-\frac{S^2}{2\gamma^2}}\right)\right), & \text{otherwise} \end{cases} \quad (3)$$

where $$R_A = \frac{|\lambda_2|}{|\lambda_3|}$$

differentiates vessels from sheet-like structures, $$R_B = \frac{|\lambda_1|}{|\lambda_2 \lambda_3|}$$

differentiates vessels from spherical structures (see, e.g., FIG. 4C for the relationship between local structure and eigenvalues of Hessian matrix), $$S = \sqrt{\lambda_1^2 + \lambda_2^2 + \lambda_3^2}$$

suppresses noise structures, and $\sigma = r\sqrt{2}$ specifies the diameter of the vessels to be detected, where r is the vessel radius. The scale parameters, $\alpha$, $\beta$, and $\gamma$ are used to balance tube-sheet differentiates, tube-sphere differentiation, and noise structures suppression, respectively. The larger the value of the parameter, the smaller effect the corresponding criterion will provide. With no prior information about surrounding background structure, differentiation for sheet-like and blob-like structures may be considered of similar importance so that $\alpha \approx \beta$. Additionally, to avoid blurring the image the strength of noise structure suppression may be set to be weaker than that of structure differentiation; i.e., $\alpha$, $\beta << \gamma$. In this example processing, $\alpha$, $\beta$, $\gamma$, were empirically set to 0.25, 0.25 and 10, respectively. Considering the range of radii observed for the breast vasculature, the filter may be calculated with $\alpha$ ranging from, for example, 0.20 to 1.00 with a step of, for example, 0.20. The maximum filter output across all scales may be ultimately assigned as the vesselness for each voxel. This example strategy may capture both large and small vessels (see FIG. 4E for an illustration of an example "vesselness" map).

After generating the vesselness map, a threshold may be set to segment the vasculature from the background. To automatically determine this threshold, the filter in Equation 3 may be applied on a region of a fixed size (e.g., 50×100 mm$^2$ in trans-verse plane) covering the internal thoracic vessels, and the 98.5% percentile of the "vesselness" histogram of this region served as the threshold to extract vessel-like structures. To fill holes and small gaps in the resulting binary map, directional dilation may be performed on the non-vascular voxels near the detected vessel segments. The resulting segmented vessels may then be skeletonized (i.e., thinning to their centerlines) and converted to a graph, where edges of the graph are individual vessel segments, and nodes are branching points or isolated endpoints. Ultimately, a 3D reconstruction of breast vasculature may be generated (see, e.g., FIG. 4F for an illustration of vessel segmentation and graph analysis).

With respect to vessel tracking and detection, based on the 3D reconstruction of vasculature, the "tumor-associated vessels" (e.g., those vessels physically connected to the tumor) can be identified. During this process, situations may be encountered in which (1) the vessels directly "touch" the tumor in the sense that a voxel within a segmented vessel is physically adjacent to a voxel associated with the segmented tumor, and/or (2) vessels separating into multiple small branches near the tumor, but these connections are not detectable by the segmentation scheme outlined in the previous section. Although the first condition may require no further analysis, for the latter condition, the goal may be to estimate the existence of a tumor-vessel connection.

Figure 4G:
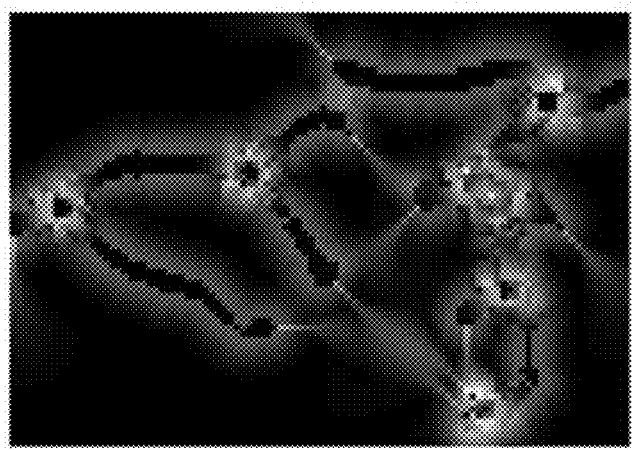

A missing connection between a vessel and the tumor itself may be due to various causes. First, for example, the vessel segments may simply be too small to form visible, tube-like structures given the spatial resolution, causing them to be undetectable with the Hessian-based filter. However, although below the resolution of the acquisition, these smaller vessels still may yield some degree of local enhancement in various embodiments. Therefore, the original subtraction image could provide information for connection estimation (see, e.g., FIG. 2D for illustration). Second, the small branches can form locally tube-like structure, which means the corresponding regions have a higher vesselness value than surrounding tissue. However, because of the partial volume effect, the vesselness value is not sufficient to avoid being ignored by the thresholding step in various implementations. Therefore, the whole vesselness map could contain additional information for identifying these small vessels (see, e.g., FIG. 4E for illustration). Moreover, the connections could simply be absent because of limited signal-to-noise, so that intensity-related features cannot recover the missing information. For this situation, we adapted the tensor voting method to estimate the direction of most likely extension of the end of the vessel segments (see the Supporting Information and Supporting Information Figure S3 for details on tensor voting method). This method generated a saliency map where high values represent high probability for continuity of segments (see, e.g., FIG. 4G for illustration). This implementation defined a cost map formed as a linear combination of these 3 measures (i.e., the subtraction, vesselness, and tensor voting maps) as defined by Equation 4. The combination may then converted to a cost-map ranging from 0 to 1 with the exponential function in Equation 5, $$\text{cost map} = e^{-\alpha I}, \quad (4)$$

$$I = \phi_S \cdot (\text{subtraction}) + \phi_V \cdot (\text{vesselness}) + \phi_T \cdot (\text{tensor voting map}) \quad (5)$$

where the $\phi_i$ correspond to the weight of the $i^{th}$ measure, $\alpha > 0$, and $\phi_s + \phi_v + \phi_t = 1$. For simplification, we set $\alpha = 10$, $\phi_s + \phi_v + \phi_t = 33.3\%$. Therefore, in the cost map, the lower the value of 1 voxel, the higher probability for unsegmented small vascular branches to exist at the specific voxel's location (see FIG. 2H for an illustration of cost map).

For each individual vessel segment that terminated within 10 mm of the tumor edge, Equation 4 may be used to compute the lowest-cost path from the termination of this vessel segment to all other vessels as well as the edge of lesion via the Dijkstra's algorithm. If the lowest cost lead to a lesion, the vessel would be identified as a "tumor-associated vessel." This strategy eventually allows for the detection of vessel segments that have a high probability of contacting the lesion, as well as the path that is the most likely physical connection between the vessel and tumor (see FIG. 2I for illustration).

After applying the tracking algorithm, all vessels were labeled based on their relationship with the lesion as either (1) directly touching the tumor (labeled as "1"), (2) spreading toward the tumor as determined by the algorithm just described (labeled as "2"), and (3) no connection to the lesion (labeled as "0"). The vessels associated with each lesion were then automatically counted by going through all individual vessels and recording the number of vessels with non-zero labels.

With respect to pharmacokinetic modeling, with the computed pre-contrast $T_1$ map, the dynamic signal intensity time course can be calibrated to the time course of concentration of contrast agent, thereby enabling pharmacokinetic analysis. As the ultrafast DCE-MRI protocol recorded data for ~1 min after the injection of contrast agent, only the initial uptake and plateauing of the curve may be captured, thereby precluding an accurate estimate for the extravascular extracellular volume fraction (i.e., $v_e$). Therefore, for pharmacokinetic analysis, we chose a simplified version of the standard Tofts-Kety modell that assumes that the exchange of contrast agent between the 2 components is unidirectional (i.e., only from the plasma to the interstitial space) with the rate $K_{trans}$:

$$C_t(T) = K^{trans} \int_0^T C_p(t) dt + v_p C_p(T) \quad (6)$$

where $C_t(t)$ and $C_p(T)$ are the time courses of the concentration of contrast agent in the tissue and the plasma, the so-called arterial input function (AIF), respectively.

Typically, the AIF may be obtained from large arteries visible in the imaging FOV. If this $C_p(t)$ is placed directly in Equation 6, errors in the estimated parameters could occur because of delay or dispersion of $C_p(t)$ by the time it arrives at the voxel of interest. This can be exacerbated in ultrafast DCE data. Therefore, a delay term can be may be incorporated in $C_p(t)$. First, for each patient, the individual $C_p(t)$ may be estimated from the signal intensity time course of the internal thoracic arteries (shown in FIG. 5A) that were semi-automatically identified using a previously established method. The individual AIFs may then be aligned and averaged to form a population AIF, $C_{p,pop}(t)$. When applying to each voxel in a particular patient, the population AIF may be shifted by an amount equal to the difference between the arrival time at the voxel and the enhancement time of the population AIF, delay$_{pop}$; such a procedure allows for temporally aligning the $C_p(t)$ and $C_t(t)$ curves (see FIG. 5C). That is, for each voxel, the $C_p(t)$ term in Equation 6 may be replaced with that given in Equation 7:

$$C_p(t) = \begin{cases} 0, & 0 < t \le \text{delay}_{pop} \\ C_{p,pop}(t - \text{delay}_{pop}), & t > \text{delay}_{pop} \end{cases} \quad (7)$$

With respect to vascular measure, after the vascular tree for the whole breast is determined, the number of vessels associated with each lesion (termed count) may be determined. Additionally, the ratio of the actual length to the linear distance between endpoints of a vascular segment for each vessel (referred to as the "distance metric" (DM), which measures the tortuosity, may be computed. Thus, in such implementations, for each lesion, 2 morphological and 3 functional metrics may be quantified: count, DM, $K^{trans}$, $v_p$, and the delay (which refers to the delay of bolus arrival time at each voxel location compared to the initial enhancement time of the individual AIF as measured at the internal thoracic arteries of the patient).

The vasculature may be color-coded according to the bolus arrival-time estimate to establish the temporal and spatial relationship between input and output vessels. With the tumor-associated vessels and the bolus arrival-time estimates, the lesion input and output functions (LIF and LOF, respectively) may be generated. For each lesion, "vascular voxels" may be defined to be the voxels within identified tumor-associated vessels that are significantly enhanced. Vascular voxels with the lowest 5% arrival-time may then be defined as "lesion input regions," and voxels with the highest 5% arrival-time may be defined as "lesion output regions." Finally, the estimate of LIF or LOF for each lesion may be obtained by averaging the signal intensity time-courses of "lesion input regions" or "lesion output regions."

With respect to statistical analyses, the nonparametric Wilcoxon rank sum test may be used to assess differences in both the morphological and functional measures between malignant and benign lesions. Univariable and multivariable logistic regression modeling may also be used to assess their ability to differentiate malignant from benign lesions. Model performance may be evaluated by receiver operating characteristic (ROC) curve analysis with leave-one-out cross-validation. Areas under the ROC curves (AUCs), as well as sensitivity and specificity at the optimal cutoff point as determined by the maximum Youden's index, may be calculated for comparison. Additionally, Spearman's correlations may be calculated to determine the statistical relationship between the measures. Statistical significance was defined as P<0.05.

Figure 5D:
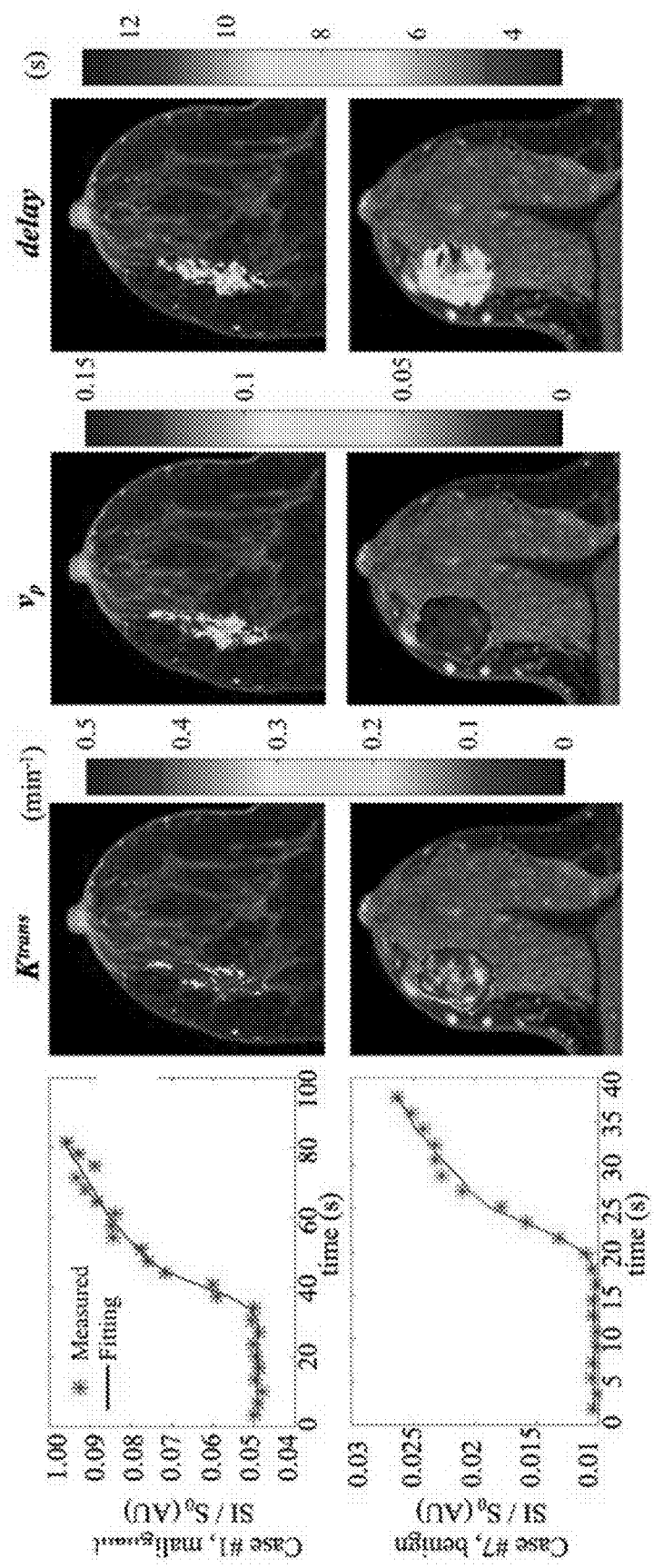

In summary, 15 patients presenting with a total of 24 lesions were included in the analysis of the demonstrative implementation; 13/24 (54%) were malignant and 11/24 (46%) were benign (Table 1). No significant difference in lesion size was found between malignant and benign lesions (P=0.202). All the patients were reported to be suspicious or highly suggestive of malignancy based on clinical assessment (BI-RADS=4 or 5), although 5/15 patients had only benign lesion(s). FIG. 5D depicts the results of pharmacokinetic modeling for representative malignant (top) and benign lesions (bottom). The first column of panel (FIG. 5D) shows the Equation 7 fitting in 1 example voxel from each patient, where the red stars are measured using the ultrafast DCE-MRI acquisition (SI/S0 refers to signal intensity normalized by S0, the relaxed signal for a 90° pulse when TR>>T1), and the blue curves are the model fits. The other columns present the $K^{trans}$, $v_p$, and bolus arrival time maps, respectively, of the central slice of the lesion, overlapped on the subtraction of the same slice. In particular, the patient shown in first row presented $K^{trans}$=0.12±0.0039 min−1 (mean±95% confidence interval [CI]), vp=0.050±0.0011 (mean±95% CI), delay=10.0±0.02 s (mean±95% CI); the patient shown in second row presented $K^{trans}$=0.18±0.0078 min−1 (mean±95% CI), $v_p$=0.015±0.00035 (mean±95% CI), delay=10.1±0.02 s (mean±95% CI).

Figure 6B:
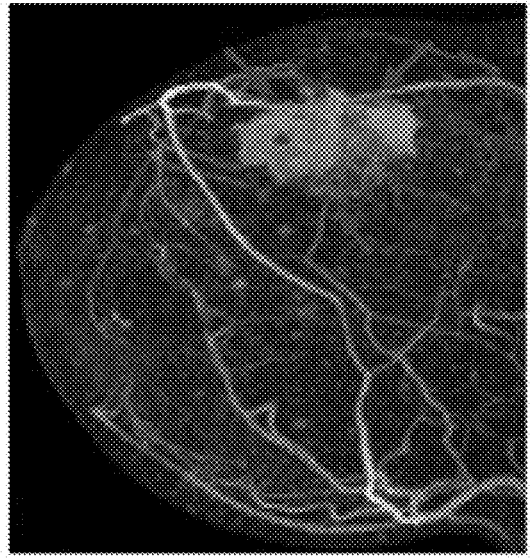
FIGS. 6A-6H depict segmentation and tumor-associated vessel identification results for two representative patient cases, with FIGS. 5A, 5C, 5E, and 5G corresponding to a benign phyllodes tumor, and FIGS. 5B, 5D, 5F, and 5H corresponding to invasive ductal carcinoma (IDC), according to potential embodiments.
Figure 6D:
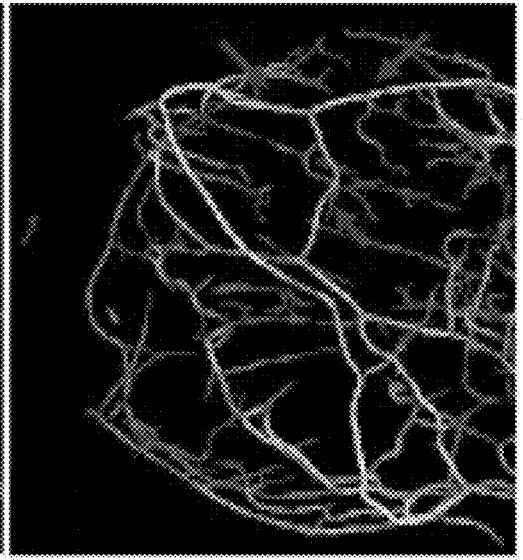
Figure 6A:
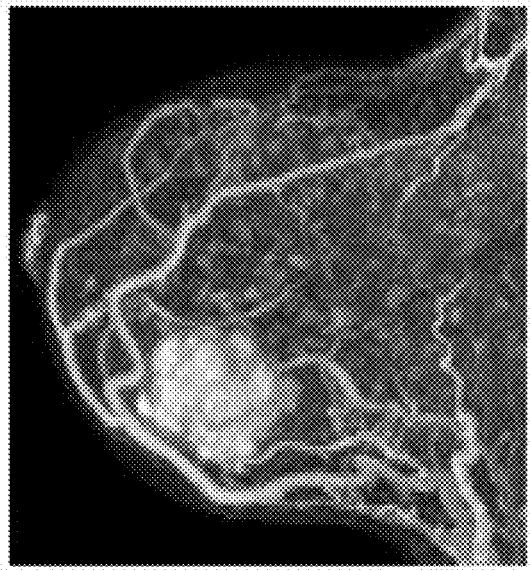
Figure 6C:
Figures 6E, 6F:
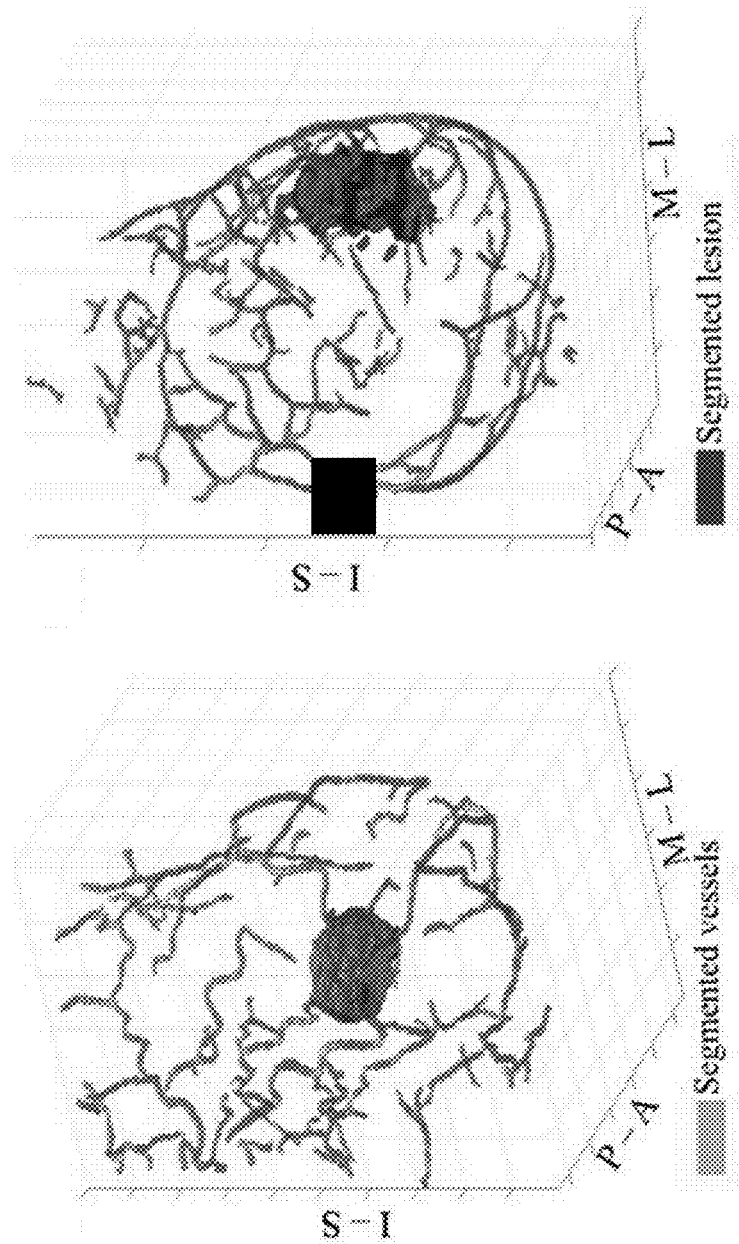
Figures 6G, 6H:
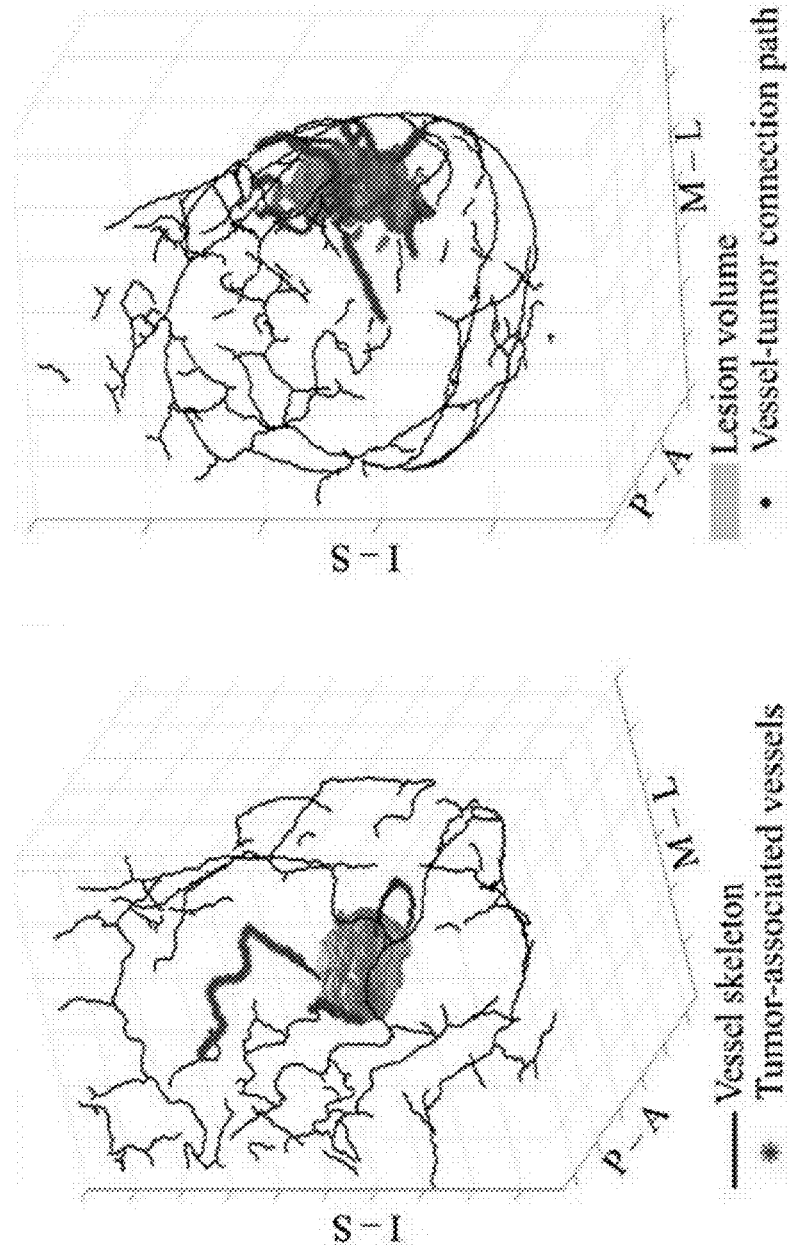

With respect to breast vasculature segmentation and tumor-associated vessel identification, within the lesions that did have tumor-associated vessels, 13 are malignant and 9 are benign; there are also 2 lesions in which no tumor-associated vessels were identified, and both are benign. FIGS. 6A-6H present the intermediate data types that were generated when building the vessel skeleton and selecting the tumor-associated vessels. In particular, the figure displays the vessel and lesion segmentations for 2 representative patients, as well as detection of the tumor-vessel connections. FIGS. 6A, 6C, 6E, and 6G present a benign tumor, while FIGS. 6B, 6D, 6F, and 6H are malignant. FIGS. 6A and 6B present the maximum intensity projections (MIPs) of high spatial resolution subtraction images for 2 cases. FIGS. 6C and 6D show the MIPs of the segmented breast vasculature, where the grey scale refers to the vesselness value and ranges from 0 to 0.4. FIGS. 6E and 6F display the 3D reconstruction of both segmented vessels (green tubes) and lesions (red volumes) with orientation labeled on axes. FIGS. 6G and 6H present the 3D reconstruction of the skeleton of segmented vascular tree (black curves) and lesion (grey volume), where the identified tumor-associated vessels are covered by red stars and the most possible vessel-tumor connection paths are shown as blue dots. The counts of tumor-associated vessels for the 2 cases were 5 and 16 (from left to right), respectively. Of note, when considering the MIP of FIG. 6B, there appears to be 3 large vessel segments touching the lesion. However, after vessel segmentation in 3D, it is clear that these vessels are connected to each other and not the tumor itself (FIG. 6D), thereby helping demonstrate the value of studying vascular structures in 3D.

Figures 7A, 7B, 7C:
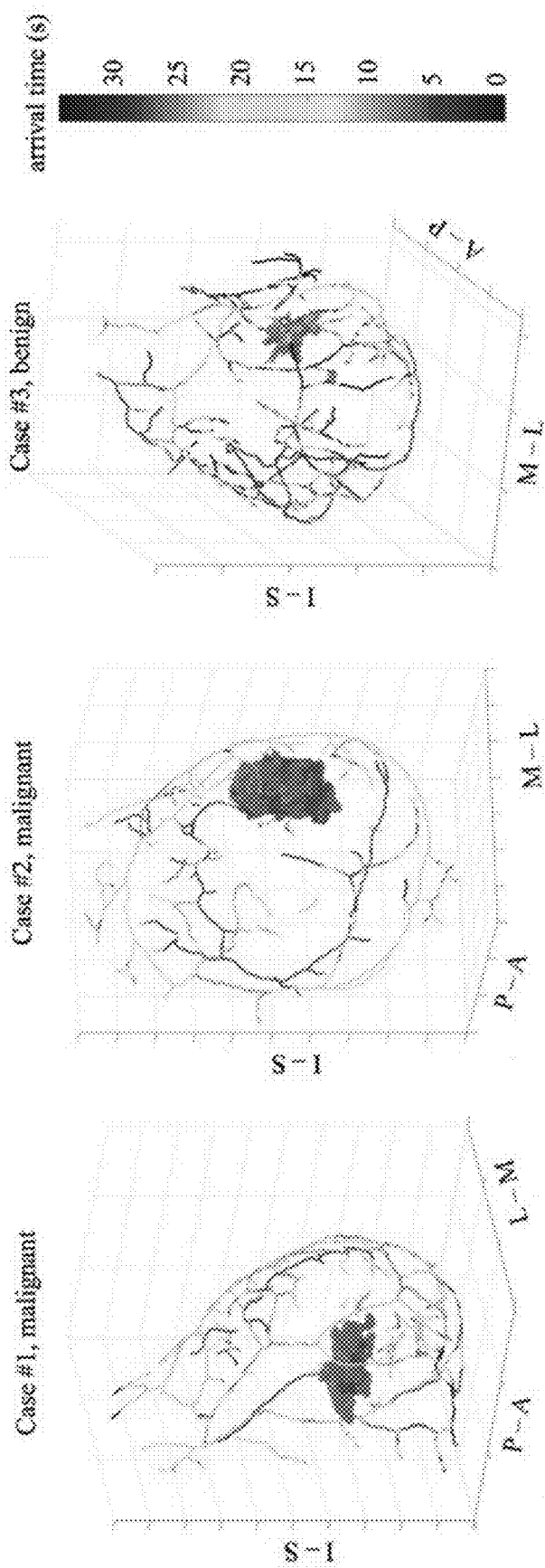
FIGS. 7A-7C depict color-coded breast vasculature indicating the arrival time for three representative malignant (FIGS. 7A and 7B) and benign (FIG. 7C) lesions, with arrival time=0 referring to the initial time of enhancement at the internal thoracic arteries for each patient, according to potential embodiments.
Figure 8A:
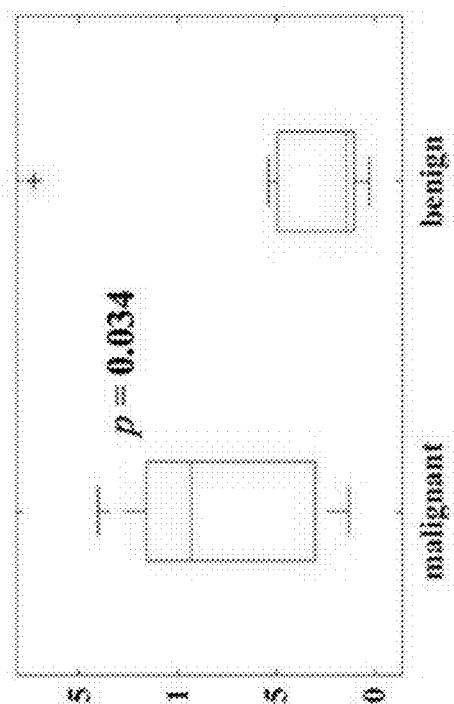
FIGS. 8A-8E depict Wilcoxon rank sum test of the quantitative measures of count of tumor-associated vessels (FIG. 7A), median of distance metric (DM) of tumor-associated vessels (FIG. 7B), median of $K^{trans}$ (FIG. 7C), median of $v_p$ (FIG. 7D), and the median of arrival-time (FIG. 7E), respectively, between malignant and benign tumors, according to potential embodiments.
Figure 8B:
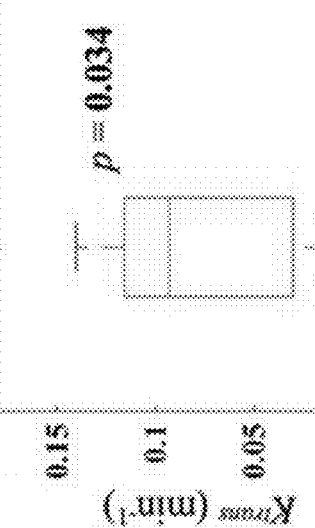
Figure 8C:
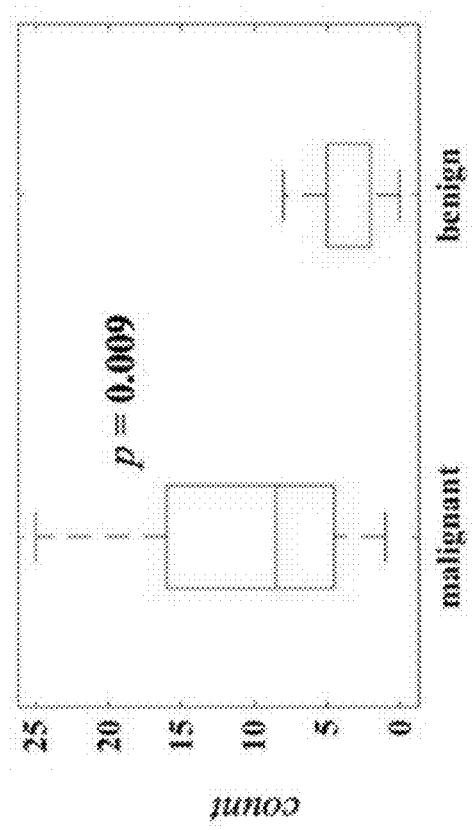
Figure 8D:
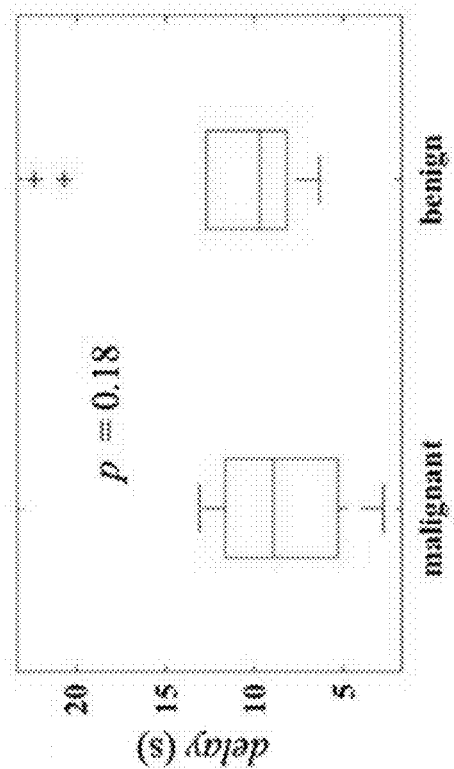
Figure 8E:
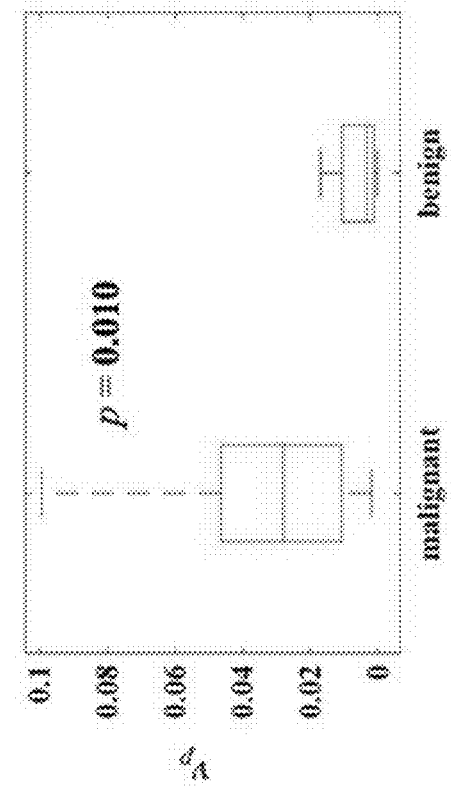

With respect to bolus arrival time visualization in breast vasculature, using the estimated arrival time maps (estimated using Equation 6), the temporal order for the bolus of contrast agent travelling through the vasculature can be visualized by color-coding. FIGS. 7A-7C show the visualization in 3 representative cases, where the arrival time value may be normalized to the initial time of enhancement of the internal thoracic artery for each patient (the location of the internal thoracic artery is indicated in FIG. 5A). In particular, the arrival times at vessel regions for the 3 patients are 11.0±0.1 s, 9.2±0.1 s, 7.3±0.1 s (mean±95% CI), respectively. The color-coded 3D reconstruction of vasculature helps to distinguish the arteries and veins. As shown in FIGS. 7A, 7B, and 7C, hot color represents an early bolus arrival time, which means the corresponded vessels are likely to be arteries; cold color represents a late arrival time, suggesting the corresponded vessels to be veins.

With respect to lesion input and output functions assessment, of the 13 malignant lesions, valid lesion input and output functions could be identified in 11 cases. Among the 11 benign lesions, 4 had valid lesion input and output functions. Potential reasons for not obtaining a valid LIF or LOF include (1) there were no tumor-associated vessels identified, or (2) the voxels within the identified tumor-associated vessels were not significantly enhanced to provide an input or output function. The latter situation could be because of the limits of SNR or the partial volume effect. In comparing the averages of the lesion input and output functions for malignant and benign lesions, although the statistical significance is limited, the LIFs and LOFs tend to show differences (P=0.16) between benign and malignant lesions.

With respect to assessments of morphological and functional measures, as summarized in Table 3, count, $K^{trans}$, and $v_p$ had significant differences between malignant and benign lesions based on the Wilcoxon test (P=0.009, 0.034, and 0.010, respectively). DM and delay showed no significant differences between malignant and benign lesions (P=0.12 and 0.18). The diagnostic performances were compared for count, DM, $K^{trans}$, $v_p$, and delay, using ROC analysis of univariable logistic regression modeling and returned AUCs=0.76, 0.33, 0.63, 0.70, and 0.57, respectively. In Spearman's correlation between the measures, $K^{trans}$ and $v_p$ showed significant correlation (P<0.0001).

TABLE 3

Measurements of benign and malignant breast lesions (N = 24)

| | Median (range) | | | |
|---|---|---|---|---|
| Metrics | Benign (N = 11) | Malignant (N = 13) | P-value (Wilcoxon) | AUC (LOOCV) |
| Morphological vascular metrics | | | | |
| Count | 3 (0-8) | 8 (1-25) | 0.009 | 0.76 |
| DM | 1.3 (1.2-1.6) | 1.2 (1.1-1.5) | 0.12 | 0.33 |
| Functional metrics | | | | |
| $K^{trans}$ | 0.013 (0.0026-0.17) | 0.073 (0.013-0.14) | 0.034 | 0.63 |
| $v_p$ | 0.0022 (0.00025-0.017) | 0.021 (0.0020-0.099) | 0.010 | 0.70 |
| Delay (s) | 10.5 (6.4-22.4) | 8.9 (2.8-13.1) | 0.18 | 0.57 |

Abbreviations: AUC, area under curve; DM, distance metric; LOOCV, leave-one-out cross validation With respect to diagnostic performance of multivariate linear regression models, to determine if the ability to separate malignant from benign disease could be improved by combining the morphological and functional measures, several univariate and multivariate regression models were compared (see Table 4). First, only morphological metric(s) were used to generate models; in particular, models using (1) count and DM, (2) count only, and (3) DM only were generated. The regression model that incorporated only count yielded the best performance with an AUC=0.76. Second, only functional metric(s) were used to generate models; in particular, (1) $K^{trans}$, $v_p$, and delay, (2) $K^{trans}$ and $v_p$, (3) $K^{trans}$ and delay, (4) $v_p$ and delay, (5) $K^{trans}$, (6) $v_p$, and (7) delay. The regression model which included $v_p$ and delay yielded the best performance with an AUC=0.79. Finally, both morphological and functional measures were used to generate models, which included all possible combinations of the five measures. The regression model that included count and delay yielded the best performance of AUC=0.91. In certain embodiments, a model including all parameters (i.e., count, DM, $K^{trans}$, $v_p$, delay) may not perform as well due to overfitting.

TABLE 4

Diagnostic performance of multivariate logistic regression models

| | LOOCV Optimal cut-off | | |
|---|---|---|---|
| Models | Sensitivity | Specificity | AUC |
| With morphological metric(s) | | | |
| Complete (count, DM) | 0.69 | 0.91 | 0.56 |
| Best performance (count) | 0.77 | 0.91 | 0.76 |
| With functional metric(s) | | | |
| Complete/best performance ($K^{trans}$, $v_p$, delay) | 0.54 | 1.00 | 0.78 |
| Best performance ($v_p$, delay) | 0.69 | 0.91 | 0.79 |
| With both morphological and functional metric(s) | | | |
| Complete (count, DM, $K^{trans}$, $v_p$, delay) | 0.69 | 1.00 | 0.69 |
| Best performance (count, delay) | 0.77 | 1.00 | 0.91 |

Abbreviations: AUC, area under curve; DM, distance metric; LOOCV, leave-one-out cross validation In various embodiments, the above image processing approach can automatically detect tumor-associated vessels and identify the vascular inputs and outputs of lesions. This methodology allows for extraction of both morphological and functional information about lesion blood supply condition by combining ultrafast DCE-MRI scans with standard high spatial resolution DCE scans. Such an example methodology enables generation of (1) morphological vascular metrics representing the number and tortuosity of vessels associated with individual breast lesions (count and DM), and (2) functional metrics representing lesion vascular input and output kinetics (LIF and LOF), and pharmacokinetic parameters, $K^{trans}$, $v_p$, and delay, representing characteristics of microvasculature within the lesion. The metrics count, DM, $K^{trans}$, $v_p$, and delay were assessed for the accuracy of malignant discrimination, individually and in linear combinations. The statistical assessments indicated that count, $K^{trans}$, and $v_p$ showed significant differences between malignant and benign lesions, and $K^{trans}$ and $v_p$ were significantly correlated. The best multivariate models for differentiation included unique parameters from the framework, count and delay. Integrating quantitative analysis of both morphological and functional measures thus can improve the diagnostic, therapeutic planning, and treatment evaluation abilities of MRIs. Moreover, vascular inputs and outputs tend to show differences between malignant and benign lesions, and as such, there may be characteristic microcirculation patterns of malignancy that are observable on MRIs.

In various embodiments, an automated tumor-associated vessel detection and quantification methods may be combined with functional analyses, taking advantage of ultrafast sampling. The result that only $K^{trans}$ and $v_p$ were significantly correlated among all assessed measures, indicated that delay, count, and DM may contain information that is not characterized by $K^{trans}$ and $v_p$. Thus, adding these measures benefits diagnosis, assessment of aggressiveness of known cancers to aid in treatment planning, and other clinical applications. Coupling morphological and functional information related to tumor vasculature enhances diagnostic accuracy beyond what can be achieved by either approach individually. Because the patients included in the data set of the demonstrative implementation were all BI-RADS scores of 4 or 5, the quantitative analysis of extracting and integrating measures that are related to tumor vasculature may be used in diagnosis and treatment of difficult cases.

Vessel detection combined with quantitative analysis of ultrafast DCE-MRI data thus yields a quantitative characterization of both morphological and functional features of tumor-associated vasculature in potential embodiments.

Figure 9:
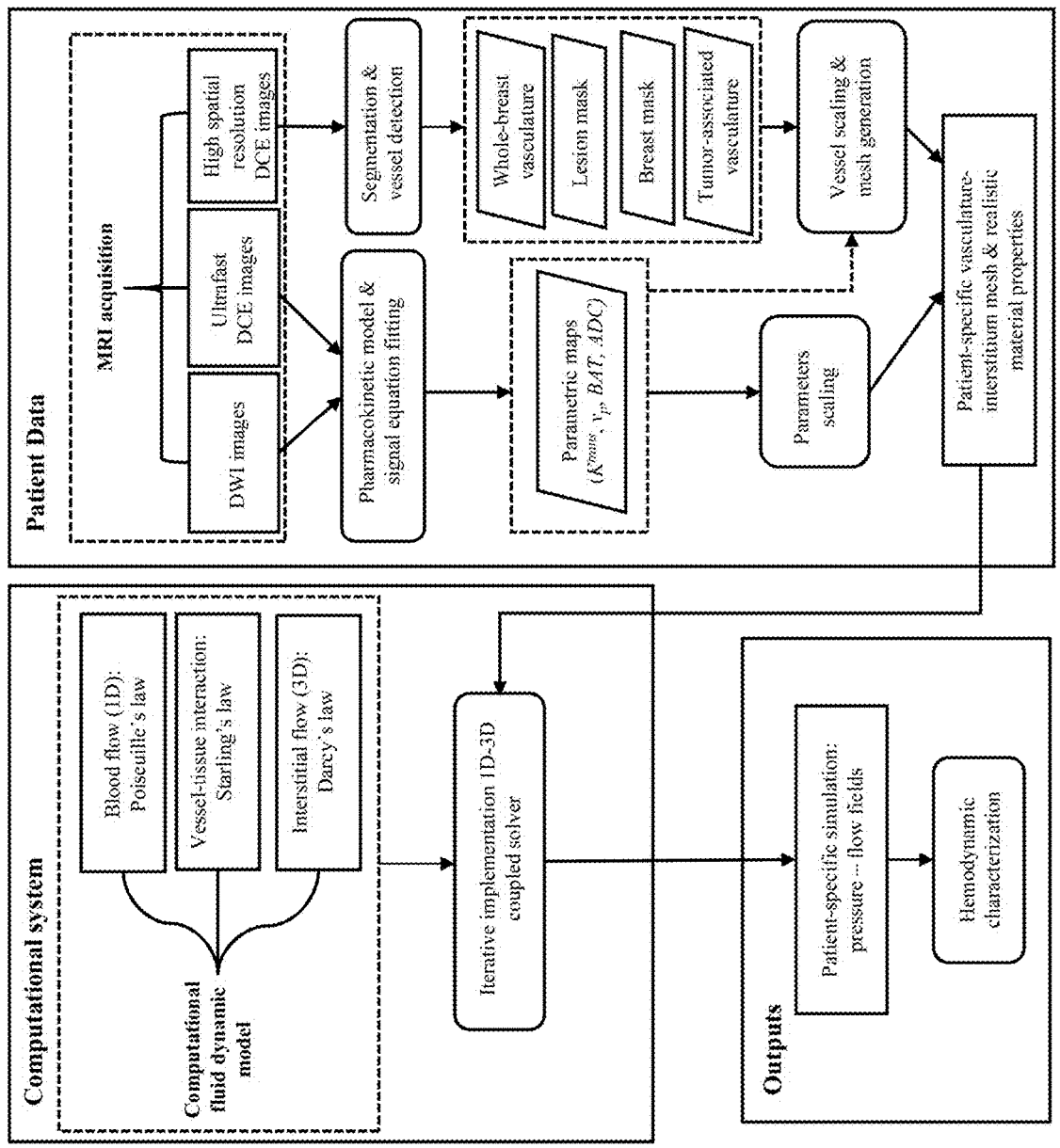
FIG. 9 depicts an example computational fluid dynamics model and a numerical implementation thereof, according to potential embodiments.

Alternatively or additionally, computational fluid dynamics may be applied to various metrics as part of image-guided computational systems, in various potential embodiments. Referring to FIG. 9, MRI data are passed through an image processing framework to generate patient-specific meshes and material properties, which are sequentially imported into the computational model. The model may be constrained by patient-specific data to yield simulated solutions of tumor-related flow and pressure, which can then inform hemodynamic characteristics. The fluid system may be modeled by a set of equations describing blood flow, interstitial transport, and their interaction throughout the ROI (e.g., the entire breast). The domain may be divided into the vascular and interstitial space via segmentation of the high-spatial resolution MRI data. These regions may then be assigned corresponding material properties via analyses of the DCE-MRI and diffusion weighted MRI (DW-MRI) data. The simulation domain may include of two parts, the vessel network $\Omega_v$, and interstitial tissue, $\Omega_t$. Example implementations may involve computing the blood flow within the vessel network along its centerlines, $\Lambda$, so that the vascular flow can be framed as a pseudo-1D problem, coupled to the 3D surrounding tissue.

In various implementations, blood flow through the vessel network may be modeled in part through application of Poiseuille's law:

$$Q_v(l) = -\frac{\pi R^4(l)}{8\mu} \cdot \frac{dp_v(l)}{dl}, \ l \in \Lambda \qquad (8)$$

where l is the length along the vessel, $Q_v$ is the flux of the blood, $p_v$ is the vascular pressure, R is the radius of vessel, and $\mu$ is the dynamic viscosity of blood (see Table 5 for a complete list of parameter symbols and definitions). Interstitial flow may be modeled in part through application of Darcy's law:

$$u_t(x) = -\kappa(x) \cdot \nabla p_t(x), \ x \in \Omega_t \qquad (9)$$

where x is the coordinate in the 3D tissue domain, $u_t$ and $p_t$ are the interstitial flow velocity and pressure, respectively, and $\kappa$ is the hydraulic conductivity of the interstitium.

Finally, flux across the vascular walls may be modeled in part on application of Starling's law:

$$q_e(l) = L_p(l) \cdot [p_v(l) - p_{t,ev}(l)], \ l \in \Lambda \qquad (10)$$

where $q_e$ is the rate of extravasation over a unit surface area, $L_p$ is the vascular permeability, $p_{t,ev}$ is the pressure at the exterior surface of the vessel averaged along the perimeter at the position l.

TABLE 5

Symbols for computational fluid dynamics model

| Symbol | Parameter (Units) | Assignment |
|---|---|---|
| $\Omega_t$ | Interstitial tissue domain (–) | 3 D mesh generated from images |
| $\Omega_v$ | Vascular region (–) | 3 D mesh generated from images |
| $\Lambda$ | Vascular network (–) | Pseudo-1 D skeleton generated from images |
| $Q_v$ | Blood flow rate (cm$^3$ s$^{-1}$) | Calculated based on Eq. (8) |
| $p_v$ | Blood pressure (g cm$^{-1}$ s$^{-2}$) | Calculated based on Eq. (13) |
| L | Length along vessels (cm) | Independent variable in FDM |
| R | Vascular radius (cm) | Scaled using $v_p$ |
| $\mu$ | Blood dynamic viscosity (g cm$^{-1}$ s$^{-1}$) | Assigned as constant 0.04, based on literature |
| $U_t$ | Interstitial flow velocity (cm s$^{-1}$) | Calculated based on Eq. (9) |
| $P_t$ | Interstitial pressure (g cm$^{-1}$ s$^{-2}$) | Calculated based on Eq. (14) |
| X | Coordinate in interstitial tissue (cm × cm × cm) | Independent variable in FEM |
| $\kappa$ | Tissue hydraulic conductivity (g$^{-1}$ cm$^3$ s) | Calibrated using ADC |
| $Q_e$ | Net efflux across vessel wall per unit surface area (cm s$^{-1}$) | Calculated based on Eq. (10) |
| $p_{t,ev}$ | Pressure at the exterior surface of vessels (g cm$^{-1}$ s$^{-2}$) | Calculated from $p_t$ during iteration |
| $L_p$ | Vascular permeability (g$^{-1}$ cm$^2$ s) | Calibrated using $K^{trans}$ |

Conditions of continuity (flux and pressure) at the junction points of the vascular network and within the tissue region may be modeled using Equations (11)-(15):

$$P_v|_{m,j} = P_v|_{dk_k,j}, \ j \in \{\text{junction points}\} \qquad (11)$$

$$Q_v|_{m,j} = \sum_{k=1}^{N_d} Q_v|_{d_k,j}, \ j \in \{\text{junction points}\} \qquad (12)$$

$$\frac{dQ_v(l)}{dl} + 2\pi R(l) \cdot q_e(l) = 0, \ l \in \Lambda \qquad (13)$$

$$\nabla \cdot u_t(x) = 0, \ x \in \Omega_t \qquad (14)$$

$$n_t(x) \cdot u_t(x) = -q_e(l(x)), \ x \in \partial\Omega_t \cap \partial\Omega_t \qquad (15)$$

where $l_{m,j}$ and $l_{dk,j}$ represent quantities at the $j^{th}$ junction point of the vessel network along the mother and $k^{th}$ daughter vessel, respectively, with Nd being the total number of daughter vessels at junction points of the vessel network, $n_t$ is the normal vector at the vascular exterior surface pointing from the tissue into the vessel, and l(x) is the position along the vessel network corresponding to the point x at the vascular exterior surface.

Using Equations (8)-(10) to eliminate the $Q_v$, $u_t$ and $q_e$ in Equations (11)-(15), one arrives at the following system:

$$\frac{d^2 p_v}{dl^2} + \frac{4}{R} \cdot \frac{dR}{dl} \cdot \frac{dp_v}{dl} - \frac{16\mu L_p}{R^3}(P_v - P_{t,ev}) = 0, l \in \Lambda \quad (16)$$

with for each j∈{junction points}, $$P_v|_{m,j} = P_v|_{dk_k,j}, \quad (17)$$

$$R^4|_{m,j} \frac{dp_v}{dl}|_{m,j} = \sum_{k=1}^{N_d} R^4|_{d_k,j} \frac{dp_v}{dl}|_{d_k,j}, \quad (18)$$

and $$-\nabla \cdot (\kappa \nabla p_t) = 0, x \in \Omega_t \quad (19)$$

with $$n_t \cdot \nabla p_t = \frac{L_p(p_v - p_{t,ev})}{\kappa}, x \in \partial\Omega_t \cap \partial\Omega_v \quad (20)$$

where Equations (16), (17), and (18) characterize the vasculature, and Equations (19) and (20) characterize the interstitial space.

In a demonstrative implementation, two patients are included, one patient presenting with an invasive ductal carcinoma, while the second presenting with a benign radial scar. MRI data were acquired on an Achieva 3T-TX (Philips, Netherlands) with a 16-channel bilateral breast coil. DCE-MRI may be performed with a heavily $T_1$-weighted, 3D spoiled gradient recalled echo protocol, consisting of one fat-suppressed, pre-contrast high-spatial resolution acquisition, four pre-contrast ultrafast acquisitions, and 19 post-contrast ultrafast acquisitions after the injection of 0.1 mM/kg MultiHance (Bracco, Milan), followed by four high-spatial resolution acquisitions. Pulse sequence parameters for the ultrafast scans were TR/TE/FA=3.2 ms/1.6 ms/10° with a SENSE factor of 4 in the medial-lateral direction and 2 in the cranial-caudal direction, and a partial Fourier factor of 0.7 (in both $k_y$ and $k_z$). The acquisition matrix and field-of-view were selected to yield a temporal resolution of 3.5 s and a spatial resolution of 1.5×1.5×4 mm³. Pulse sequence parameters for the high-spatial resolution scans were TR/TE/FA=5.0 ms/2.5 ms/10° with SENSE of 2.5 in medial-lateral and partial Fourier of 0.85 in $k_y$. The acquisition matrix and field of view were selected to yield a temporal resolution of approximately 55 s, and a spatial resolution of 0.8×0.8×1.6 mm³. DW-MRI data were acquired using a fat-suppressed, single-shot spin echo sequence with TR/TE=13 s/67 ms, and b-values of 0, 50, 800 s/mm2. The acquisition matrix and field-of-view were selected to yield a spatial resolution of 2×2×2.5 mm³.

Prior to the analyses described below, a non-rigid, demons registration may be applied on the DCE-MRI data to minimize any patient motion that may occur during the acquisition. Briefly, the goal is to determine a spatial transformation that best aligns consecutive 3D image frames acquired during the dynamic scanning. To do so, each dynamic frame may be aligned to the frame immediately previous to minimize the temporal gap between the reference and target images and, thus, associated changes in image features. If the image acquired at time t is I(t), the deformation field, u, to transform I(t+1) to I(t) may then be computed via:

$$u = \frac{(I(t+1) - I(t)) \cdot \nabla I(t)}{|\nabla I(t)|^2 + (I(t+1) - I(t))^2}. \quad (21)$$

A Gaussian filter with a standard deviation of 1.3 may be applied to u, yielding a smoothed deformation field which is then applied to the image to be registered, I(t+1). The resulting deformed image may be subsequently used to calculate the deformation field for the next set of time points. The calculation may be performed iteratively with a Gaussian pyramid strategy with three resolution levels. This example strategy maximizes local registration accuracy, as well as global shape preservation. The deformation of I(t+1) may be executed with 500, 400 and 200 iterations at the lowest, medium, and highest resolution, respectively.

With regard to processing of quantitative MRI data generally, and segmentation and vessel detection in particular, the registered, high spatial resolution DCE-MRI data may be used for morphological analysis using a framework previously developed (see, e.g., FIG. 3 through FIG. 8E). In various embodiments, lesions may be segmented from the surrounding breast tissue using a fuzzy c-means clustering method. In certain implementations, the same method may also be adapted for segmentation of fibroglandular and adipose tissues. Before vessel segmentation, histogram normalization and enhancement may be performed by applying a local-statistics-based, intensity transfer function to the subtraction of the pre-contrast from the post-contrast, high-spatial resolution images. The 3D vasculature may then be segmented from the surrounding tissue by applying a Hessian filter to the enhanced images, from which a probability for each voxel to belong to a vessel may be constructed. A lowest-cost tracking algorithm may be used to automatically detect vessel segments that have a high probability of contacting the lesion, as well as the path yielding the most likely physical connection between the vessel and tumor.

With regard to pharmacokinetic modeling in processing of quantitative MRI data, in various embodiments, the ultra-fast DCE-MRI data may be analyzed by a Patlak-based model modified with a delayed bolus-arrival time (BAT):

$$C_t(t) = K^{trans} \int_0^t C_p(\tau) d\tau + v_p C_p(t), \quad (22)$$

$$C_p(t) = \begin{cases} 0, & 0 < t < BAT \\ C_{p,pop}(t - BAT), & t > BAT \end{cases} \quad (23)$$

where $C_t(t)$ and $C_p(t)$ are the time courses of the concentration of contrast agent in the tissue and the local plasma, respectively, and $C_{p,pop}(t)$ is the population arterial input function measured from the internal thoracic arteries. Thus, the BAT, $K^{trans}$ (volume transfer coefficient, representing local vascular perfusion and permeability), and $v_p$ (plasma volume fraction) can be estimated for each voxel.

DW-MRI data may be analyzed by standard methods to yield parametric maps of the apparent diffusion coefficient (ADC). As the DW-MRI data may be acquired with suppression of the fat signal (as is commonly done for DW-MRI of the breast), directly mapping the ADC values of that tissue component is challenging. Thus, for adipose tissue, a literature value (e.g., ADC=1.91×10−5 mm²/s in the implementation) may be assigned to all voxels labeled as adipose tissue after segmentation. In addition, a small number of unphysical ADC values (i.e., ADC values below 0.0 or above $3.0\times10^{-3}$ mm$^2$/s) may also exist in fibroglandular tissue due to signal noise. Thus, any voxels within the fibroglandular or tumor tissues displaying unphysical values may be replaced by the average of their valid nearest-neighbors (i.e., 26 voxels in 3D in the implementation). Finally, Gaussian smoothing with a standard deviation of, for example, 1.0 may be applied at the edges of tissue regions to reduce unphysical discontinuities.

With regard to vessel scaling and mesh generation in processing of quantitative MRI data, numerical meshes of the whole breast including the lesion and vasculature may be generated from segmented masks obtained from the patient and MRI data acquisition discussed above. Due to the relatively small radius of breast vessels compared to the imaging resolution, the directly segmented vessel mask suffers from significant partial volume effects and cannot accurately represent the size of vessels. Thus, an adaptive vessel scaling algorithm has been designed by integrating information from the segmented vessel mask and the $v_p$ map.

Figure 10A:
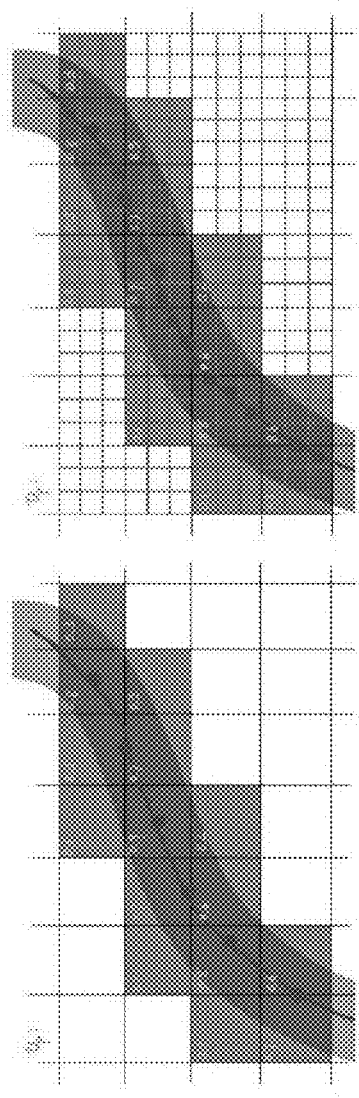
FIGS. 10A-10F illustrate adaptive vessel scaling using $v_p$ map, according to potential embodiments.
Figure 10B:
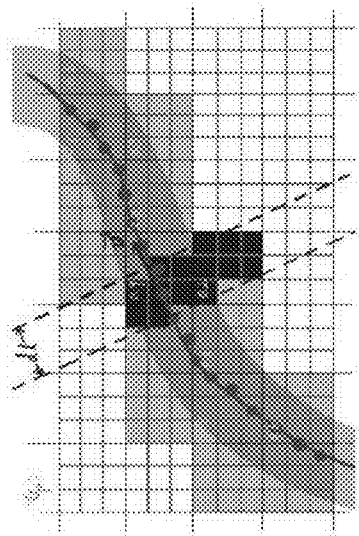
Figure 10C:
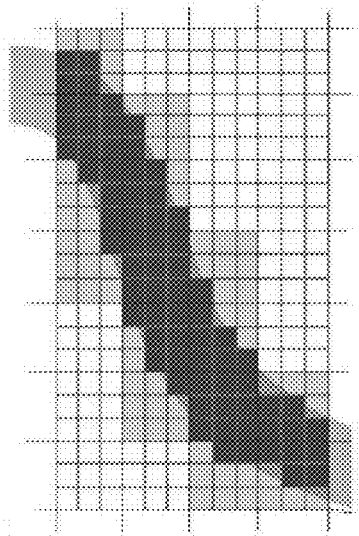

In example embodiments, first, the segmented vascular mask may be skeletonized to its centerline (FIG. 10A). This implementation may identify the branching points, isolated ends, and vessel segments of the vascular network, and calculate orientations of each vessel. A gap filling process may be applied with a similar strategy as the tumor-associated vessel tracking, so that the whole vascular network becomes a single connected graph. Further, a moving average of length seven may be applied to smooth the vessel centerlines. Second, the mask and $v_p$ map may be up-sampled to an isotropic resolution of 200 microns (FIG. 10B). Third, at each specific location along the vessel centerline, a neighborhood in the up-sampled grid may be identified using the vascular orientation and a step width dl of half of the up-sampled voxel size. This neighborhood represents the region in the original vessel mask covering the section of vessel at this location (FIG. 10C). This section may be considered to be a cylinder with height dl and an unknown radius, R, while its volume should be approximately equal to the $v_p$ value for this neighborhood multiplied by the voxel volume in the refined grid:

$$\pi R^2 \cdot dl = \sum_{i \in \{identified\ neighborhood\}} v_p(i) \cdot V_{vox}(i) \qquad (24)$$

where $v_p(i)$ is the measured plasma volume fraction for the $i^{th}$ voxel in this identified neighborhood, and $V_{vox}(i)$ is the volume of the corresponding voxel, which is a constant 0.008 mm$^3$.

Figure 10D:
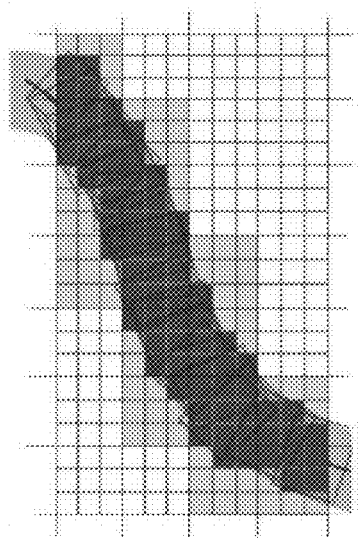
Figure 10E:
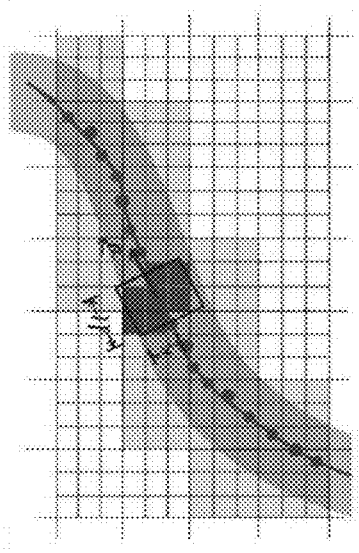
Figure 10F:
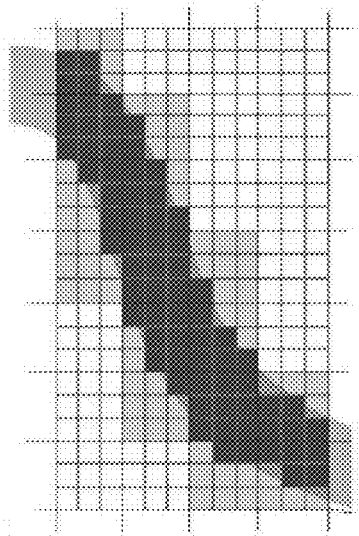

In various embodiments, Equation (24) enables the determination of the local vascular radius. The voxels within the range of the cylinder with height dl and calculated radius R may be considered the vascular region (FIG. 10D). The algorithm just described may be applied stepwise to the entire vascular network to properly scale the vessel mask throughout the domain (FIGS. 10E and 10F). Finally, the Matlab toolkit, iso2mesh, may be used to convert the binary mask to surface and volumetric numerical meshes of the vasculature. The same toolkit may also be used for generating meshes of the lesion and whole breast regions from their respective masks. The extravascular tissue mesh may then be generated by applying a Boolean difference operation (e.g., 'surfboolean' function in iso2mesh) between the breast contour and the vascular surfaces.

With respect to parameter scaling in processing of quantitative MRI data, in various embodiments, parametric maps of ADC and $K_{trans}$ inform spatial-resolved (and patient-specific) values of tissue hydraulic conductivity, $\kappa$, and vascular permeability, $L_p$, respectively. Certain implementations may assume a simple linear scaling where the median of the scaled MRI parameter matches the median of the corresponding material property value from the literature.

With respect to boundary conditions and direction of blood flow in processing of quantitative MRI data, in various embodiments, assigning appropriate boundary conditions may be needed on both the boundaries of the 3D tissue domain, $\partial\Omega_t$, as well as the isolated ends of the pseudo-1D vascular network. Three subdomains of the tissue boundary may be identified: 1) the surface contour of the breast, $\partial\Omega_{t,1}$, 2) the chest wall, $\partial\Omega_{t,2}$, and 3) the exterior surface of the vascular domain, $\partial\Omega_{t,3}=\partial\Omega_t\cup\partial\Omega_v$. In various embodiments, Dirichlet boundary condition for pressure (i.e., constant pressure $p_t=2\times10^4$ g·cm$^{-1}$·s$^{-2}$) may be assigned on $\partial\Omega_{t,1}$ and $\partial\Omega_{t,2}$, and Neumann condition may be assigned on $\partial\Omega_{t,3}$ (i.e., Equation (20)).

The Dirichlet conditions on the pressure field at the terminal ends of the vascular network, as well as the direction of blood flow, may be automatically determined using an optimization procedure (e.g., a modified optimization procedure based on the work of Fry et al. (2012)). Briefly, blood flow may first be modeled with a simplifying assumption (i.e., non-permeable vessels and a uniform vascular radius) and randomly assigned flow directions. Because the boundary condition on the terminal ends may be initially unknown, the simulation may be implemented as an optimization process with flux continuity constraints at the vascular junction points. The optimization goal is to approach the target pressures at each node and the target shear stresses in each vessel segment. Thus, various implementations minimize the object function L in Equation (25):

$$L = \frac{1}{2}k_p\sum_{k\in N}\left(\frac{1}{2}\sum_{j\in S_k}l_j\right)\cdot(p_{v,k}-p_{v,0})^2 + \frac{1}{2}k_\tau\sum_{j\in S}l_j(\tau_j-\tau_0)^2 + \sum_{i\in I}\lambda_i\left(\sum_{k\in N}K_{ik}p_{v,k}\right) \qquad (25)$$

with $$K_{ik} = \delta_{ik}\sum_{j\in S_i}\frac{\pi r_j}{8\mu l_j} - (1-\delta_{ik})\sum_{j\in S_i}\frac{\pi r_j}{8\mu l_j}, \qquad (26)$$

where kp and kτ weight the relative contribution of the pressure and shear stress terms, respectively; $p_{v,k}$ is the pressure at the $k^{th}$ of N total vascular nodes; $\delta_{ik}$ is the Kronecker delta; $l_j$ and $\tau_j$ are the length of and shear stress in the $j^{th}$ vessel segment, respectively, of S total vessels; $S_k$ the set of vessels connected to $k^{th}$ node; and $S_{ik}$ the set of vessels connecting the $i^{th}$ and $k^{th}$ nodes. The third term in Equation (25) arises through the constraint of flux continuity at the set of internal nodes, which are enforced with a standard Lagrange multiplier approach, where $\lambda_i$ represents the Lagrange multiplier for the $i^{th}$ node. The target value of wall shear stress may be set to be, for example, $|\tau_0|=15$ g·cm$^{-1}$·s$^{-2}$, and target pressure $p_{v,0}=4.13\times104$ g·cm$^{-1}$·s$^{-2}$. The viscosity of blood, μ, may be set to be, for example, 0.04 g·cm$^{-1}$·s$^{-1}$.

After each iteration of this simulation, the bolus arrival-time, $BAT^{(estimate)}$) may then be estimated and compared with the measured bolus arrival-time map, $BAT^{(measure)}$). Finally, simulated annealing (e.g., starting from a small $k\tau$ and doubling the ratio $k\tau/k_p$ during each iteration to avoid biases toward the initial randomly assigned directions) may be applied to adjust the assignment of flow directions until the normalized difference between $BAT^{(estimate)}$) and $BAT^{(measure)}$), M, is minimized; i.e., various implementations may involve minimizing:

$$M = \frac{\sqrt{\sum_{j \in s} \int_0^{l_j} \left[BAT_j^{(estimate)}(l) - BAT_j^{(measure)}(l)\right]^2 dl}}{\sqrt{\sum_{j \in s} \int_0^{l_j} \left[BAT_j^{(estimate)}(l) - BAT_j^{(measure)}(l)\right]^2 dl}}. \quad (27)$$

Such optimization procedure may determine the flow direction and pressure at all terminal ends.

To numerically solve the 1D-3D coupled simulation system, (i.e., Equations (16)-(20)), an iterative algorithm which combines the finite difference method (FDM) and the finite element method (FEM) may be implemented using, for example, the Python FEniCS library, as follows (definitions can be found above):

Step 1: Initialize pressure at exterior surface of vessel, $p_{t,ev}^{(0)}$.

Step 2: Solve Equation (16) for $p_v^{(1)}$ with the FDM on the vessels, $$\frac{2}{R(l)\Delta l} \cdot \frac{dR(l)}{dl}\left[p_v^{(1)}(l+1) - p_v^{(1)}(l-1) - \frac{16\mu L_p(l) p_v^{(1)}(l)}{R(l)^3} + \right. \quad (28)$$

$$\left. \frac{1}{\Delta l^2}\left[p_v^{(1)}(l+1) - 2p_v^{(1)}(l) + p_v^{(1)}(l-1)\right] = -\frac{16\mu L_p(l) p_{t,ev}^{(0)}(l)}{R(l)^3},\right.$$

where for each $j \in \{\text{junction points}\}$, $$p_v(end)|_{m,j} = p_v(0)|_{d_k,j} = p_v|_j, \quad (29)$$

$$R^4(end)|_{m,j} \cdot \frac{\Delta p_v(end)|_{m,j}}{\Delta l} = \sum_{k=1}^{N_d} R^4(0)|_{d_k,j} \cdot \frac{\Delta p_v(0)|_{d_k,j}}{\Delta l}. \quad (30)$$

Step 3: With the estimated $p_v^{(1)}$ and Equation (20), solve Equation (19) for $p_t^{(1)}$ using the FEM with tetrahedral elements and a test space of second-order, continuous, piecewise-linear polynomials:

$$\int_{\partial\Omega_t \cap \partial\Omega_v} L_p(l(x))\left[p_v^{(1)}(l(x)) - p_{t,ev}^{(0)}(l(x))\right]v(x)ds = \quad (31)$$

$$\int_{\Omega_t} \kappa(x) \cdot \nabla p_t^{(1)}(x) \cdot \nabla v(x)dx, \forall v \in \{\text{test functions}\}$$

Step 4: Update $p_t ev^{(1)}$ by averaging the estimated $p_t^{(1)}$) along the perimeter of vessel at position l.

Step 5: Repeat Steps 2-4, until $p_v^{(n)}$ and $p_t^{(n)}$ converge according to:

$$\frac{\|p_v^{(n)} - p_v^{(n-1)}\|_{L^2}}{\sqrt{\|p_v^{(n)}\|_{L^2} \cdot \|p_v^{(n-1)}\|_{L^2}}} + \frac{\|p_t^{(n)} - p_t^{(n-1)}\|_{L^2}}{\sqrt{\|p_t^{(n)}\|_{L^2} \cdot \|p_t^{(n-1)}\|_{L^2}}} < \varepsilon = 10^{-5}. \quad (32)$$

Once this system (i.e., Equations (16)-(20)) is solved, it provides a steady-state blood pressure, $p_v$, and interstitial pressure, $p_t$, field throughout the domain. The local blood flow rate, $Q_v$, and interstitial flow velocity, $u_t$, can now be calculated based on Equations (8) and (9), respectively. Blood flow velocity, $u_v$, and wall shear stress, wss, may then be calculated via Equations (33) and (34), $$u_v = \frac{Q_v}{\pi R^2} \quad (33)$$

$$wss = \frac{4\mu Q_v}{\pi R^3}. \quad (34)$$

With respect to hemodynamic characterization, hemodynamic characteristics may be generated for quantitative comparison between the malignant and benign lesions in various embodiments. For each patient, distributions of $p_v$, $u_v$, wss and $q_e$ in the whole breast vasculature, as well as the $p_t$ and $|u_t|$ in the tumor regions, may be compared between diseased and contralateral breasts, as well as between malignant and benign lesions, via two-sample, Kolmogorov-Smirnov (K-S) statistic in various implementations. The K-S distance, $D_{k-s}$, may be calculated as the comparing measurement for each characteristic, i.e., $$D_{k-s} = \max_x |F_1(x) - F_2(x)|, \quad (35)$$

where $F_1(x)$ and $F_2(x)$ are the cumulative probability distributions for the two samples to be compared.

Additionally, in various embodiments, inlet and outlet vessels (i.e., with flow entering and leaving the tumor) may be identified and blood flow rate through the tumor for each lesion determined.

With respect to establishing the patient-specific domain, FIG. 11 shows the direct outputs of image processing for the patient with a malignant lesion (FIGS. 11A-11E) and the patient with a benign lesion (FIGS. 11F-11J). FIGS. 11A and 11F show 3D reconstructions of the vascular skeleton for the whole breast, lesions, and detected tumor-associated vessels. For the malignant lesion, seven tumor-associated vessels were detected, with one inlet and six outlets. The benign lesion has three tumor-associated vessels detected, with one inlet and two outlets. Also shown are the measured BAT (FIGS. 11B and 11G), $v_p$(FIGS. 11C and 11H), $K^{trans}$ (FIGS. 11D and 11I), and ADC (FIGS. 11E and 11J) parametric maps in diseased breasts. The median of parameters for the malignant tumor are BAT=9.98 s, $v_p$=1.45×10$^{-2}$, $K^{trans}$=0.34 min$^{-1}$, and ADC=1.15×10$^{-3}$ mm$^2$ s$^{-1}$; parameters for the benign tumor are BAT=11.10 s, $v_p$=1.00×10$^{-4}$, $K^{trans}$=0.04 min$^{-1}$ and ADC=9.60×10$^{-4}$ mm$^2$ s$^{-1}$. A reporting can be found in Table 6.

TABLE 6

Results of image processing and hemodynamic analysis

| Parameters | Malignant tumor | Benign tumor |
|---|---|---|
| *Image processing* | | |
| BAT (s) | 9.98 (9.21-11.02) | 11.10 (4.84-15.32) |
| $v_p$ | $1.45 \times 10^{-2}$ | $1.00 \times 10^{-4}$ |
|  | $(0.70 \times 10^{-2}\text{-}2.55 \times 10^{-2})$ | $(1.00 \times 10^{-4}\text{-}4.78 \times 10^{-4})$ |
| $K^{trans}$ (min$^{-1}$) | 0.34 (0.25-0.49) | 0.04 (0.03-0.07) |
| ADC (mm$^2$ s$^{-1}$) | $1.15 \times 10^{-3}$ | $9.60 \times 10^{-4}$ |
|  | $(9.64 \times 10^{-4}\text{-}1.35 \times 10^{-3})$ | $(7.04 \times 10^{-4}\text{-}1.21 \times 10^{-3})$ |
| *Hemodynamic* | | |
| $p_t$ (g cm$^{-1}$ s$^{-2}$) | $2.029 \times 10^4$ | $2.015 \times 10^4$ |
|  | $(2.025 \times 10^4\text{-}2.033 \times 10^4)$ | $(2.014 \times 10^4\text{-}2.016 \times 10^4)$ |
| $|u_t|$ (cm s$^{-1}$) | $7.72 \times 10^{-2}$ | $1.11 \times 10^{-2}$ |
|  | $(4.62 \times 10^{-2}\text{-}9.17 \times 10^{-2})$ | $(6.54 \times 10^{-3}\text{-}1.47 \times 10^{-2})$ |
| $p_v$ (g cm$^{-1}$ s$^{-2}$) | $3.64 \times 10^4$ | $3.34 \times 10^4$ |
|  | $(3.42 \times 10^4\text{-}4.18 \times 10^4)$ | $(2.60 \times 10^4\text{-}3.49 \times 10^4)$ |
| $u_v$ (cm$^3$ s$^{-1}$) | 0.84 (0.52-1.48) | 1.11 (0.25-1.13) |
| wss (g cm$^{-1}$ s$^{-2}$) | 6.25 (3.49-14.12) | 13.12 (3.03-13.58) |
| $q_e$ (cm s$^{-1}$) | $5.20 \times 10^{-7}$ | $3.68 \times 10^{-8}$ |
|  | $(1.89 \times 10^{-7}\text{-}5.98 \times 10^{-7})$ | $(1.77 \times 10^{-8}\text{-}5.30 \times 10^{-8})$ |

With respect to mesh generation and material properties assignment, in various implementations, FIG. 12 presents the results of mesh generation and properties assignment for the malignant (FIGS. 12A-12D) and the benign (FIGS. 12E-12H) cases. FIGS. 12A and 12E visualize the numerical meshes of vasculature and the tumor regions. $K^{trans}$ maps may be scaled to $L_p$ and assigned to the vessel mesh (FIGS. 12C and 12G. The literature value of $L_p$ fall between $2.5 \times 10^{-10} \sim 2.1 \times 10^{-9}$ g$^{-1}$ cm$^2$ s with a median of $1.2 \times 10^{-9}$ g$^{-1}$ cm$^2$ s. The median of $K^{trans}$ within the whole breast vasculature for both patients is 0.16 min$^{-1}$. Thus, a scalar coefficient of $k_1=7.6 \times 10^{-9}$ may be applied to scale the $K^{trans}$ values. Similarly, ADC maps may be scaled to κ and assigned to the tissue mesh (FIGS. 12D and 12H. The literature values of κ are between $10^{-12} \sim 10^{-1}$ g$^{-1}$ cm$^3$ s yielding a median value of $1.0 \times 10^{-11}$ g$^{-1}$ cm$^3$ s [27][47]. The median of ADC for the whole breast tissue for both patients is $1.91 \times 10^{-5}$ mm$^2$ s$^{-1}$. A scalar coefficient of $k_2=5.0 \times 10^{-7}$ is applied to the ADC values.

Figure 13A:
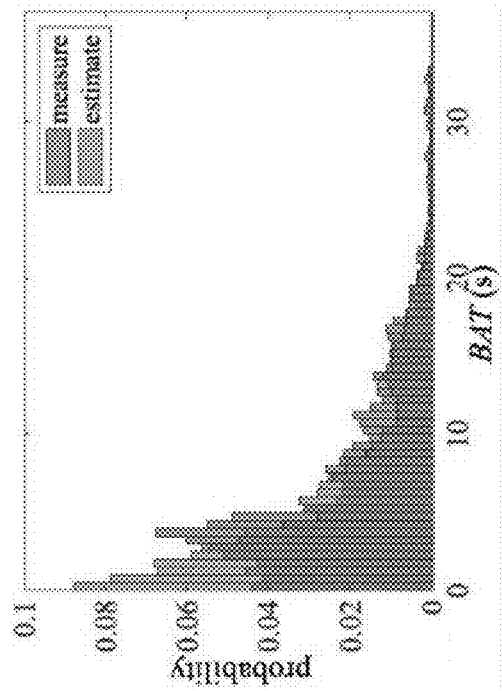
FIGS. 13A-13C depict an example optimization procedure for automatically determining direction of blood flow, according to potential embodiments.
Figure 13B:
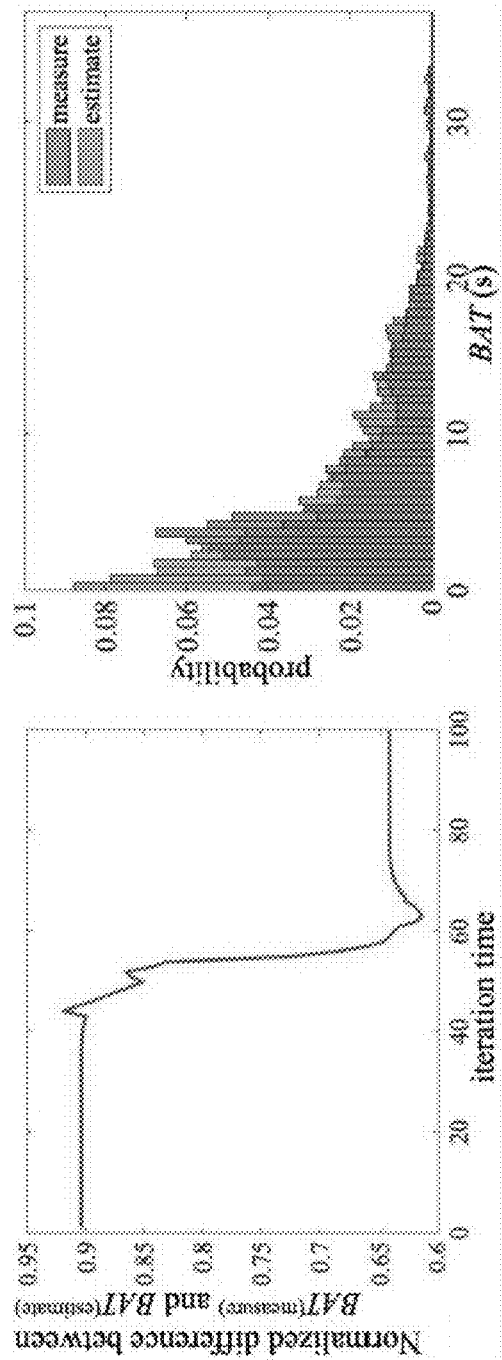
Figure 13C:
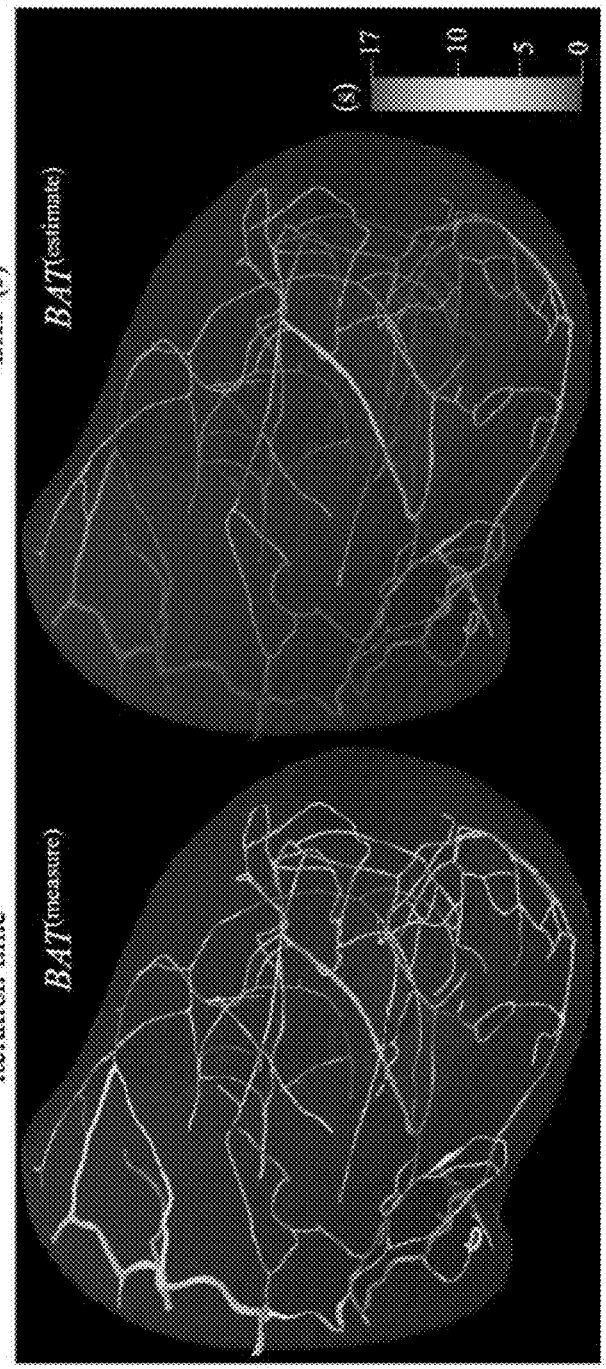
Figures 14A, 14B:
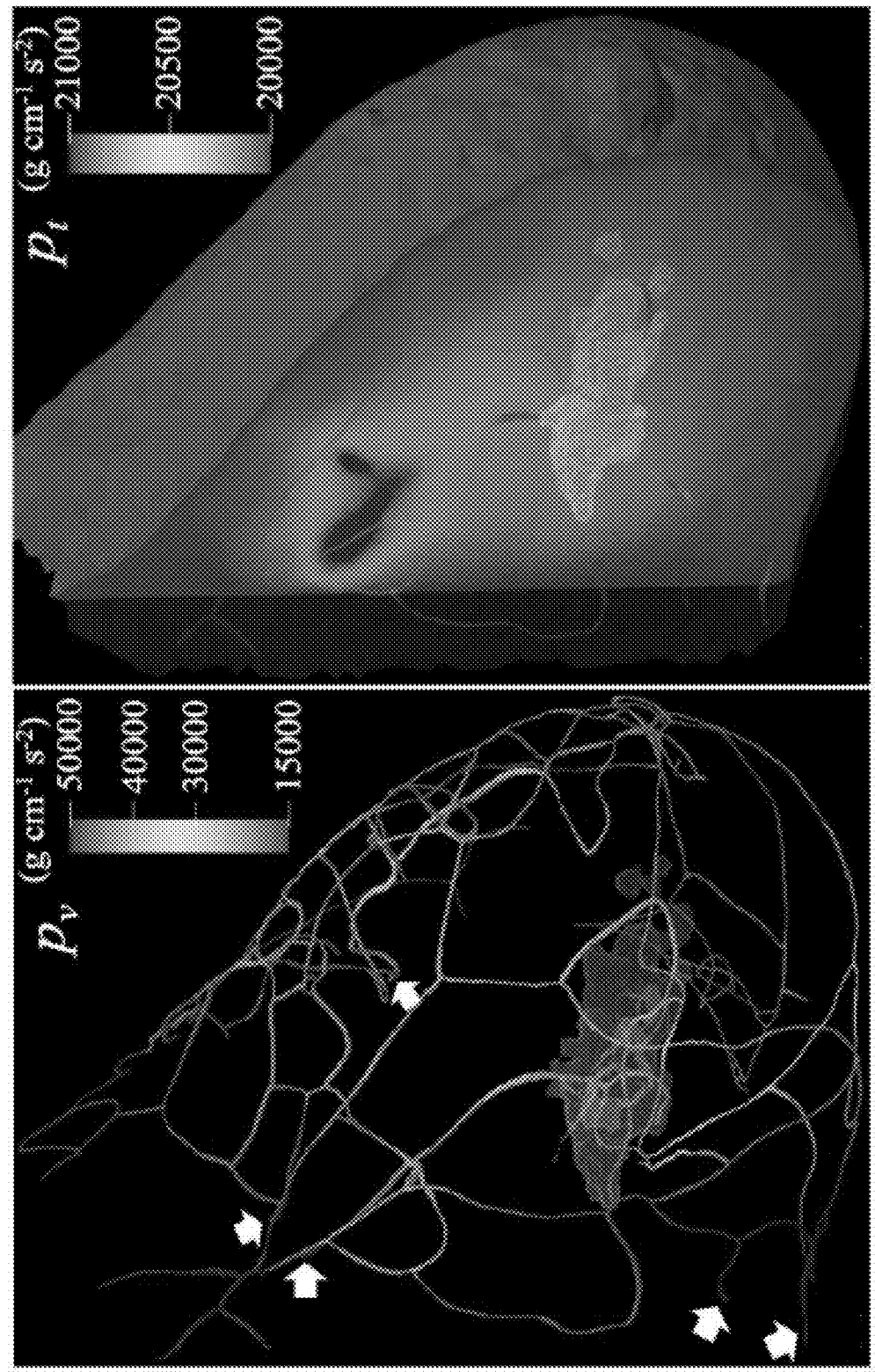
FIGS. 14A-14H depict simulation results in a whole breast and a tumor-associated region for the two patients with malignant (FIGS. 14A-14D) and benign (FIGS. 14E-14H) tumors.
Figure 14C:
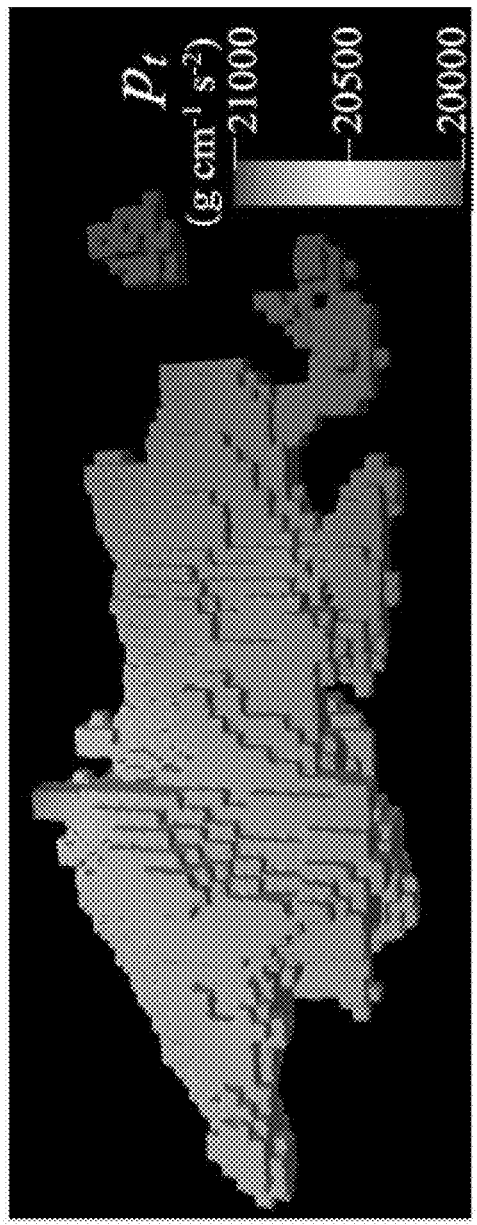
Figure 14D:
Figures 14E, 14F:
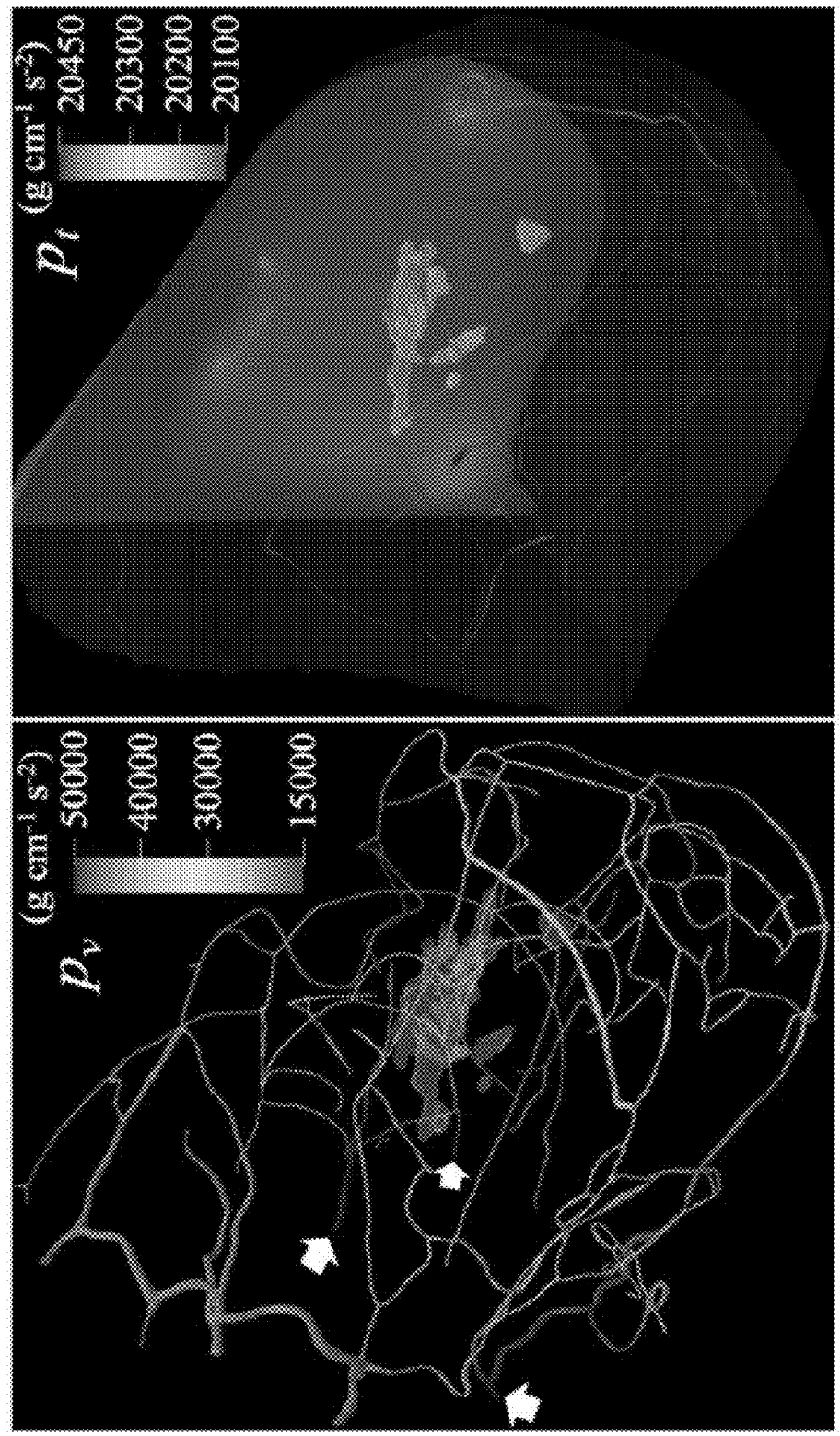
Figures 14G, 14H:
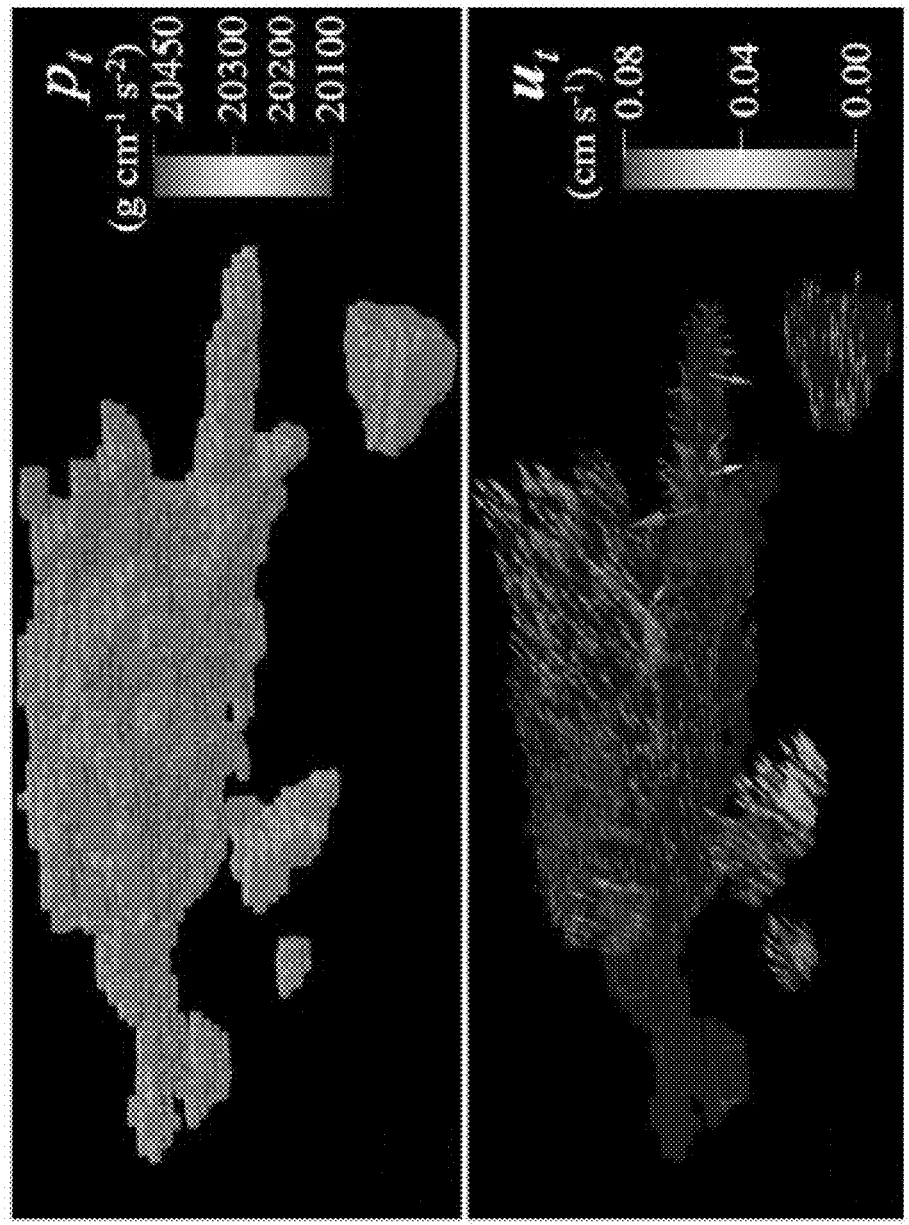

With respect to automatic determination of the direction of blood flow, FIG. 13 illustrates the results of the hierarchical optimization procedure for determining the boundary condition at vascular terminal ends and the blood flow direction in the patient with the benign lesion, in various embodiments. The objective function M reaches a minimal value of 0.61 at the 63$^{rd}$ iteration of the optimization procedure (FIG. 13A). The resulting distribution of estimated BAT shows a DICE similarity of 0.83 with the measured BAT (FIG. 13B). Spatial-resolved BATs are visualized in FIG. 13C.

With respect to whole breast pressure fields of flow simulation outputs, FIG. 14 presents solutions of the image-based flow simulation for the diseased breasts of the two patients, in various embodiments. FIGS. 14A and 14E show the blood pressure along the vasculature network for the malignant and benign diseased breasts, respectively, where major input arteries (indicated by white arrows) from the posterior and lateral sections of the breasts can be identified via the color-coding. FIGS. 14B and 14F show the interstitial pressure fields in the breasts. Due to the significant efflux from vessel to breast tissue, regions close to the exterior surface of the major arterial inputs manifest high interstitial pressure, with the median and range of $2.008 \times 10^4$ ($2.003 \times 10^4$-$2.021 \times 10^4$) g·cm$^{-1}$·s$^{-2}$; while interstitial pressure close to the venous surface is generally low, with the median and range of $1.999 \times 10^4$ ($1.995 \times 10^4$-$2.000 \times 10^4$) g·cm$^{-1}$·s$^{-2}$, where influx from tissue back to vessels presents.

With respect to tumor interstitial pressure and flow velocity fields of flow simulation outputs, enlarged views of the interstitial pressure and flow velocity fields of the tumor are also shown in FIG. 14. FIGS. 14C and 14G present the pressure fields in the malignant and benign tumors, respectively. Comparing FIGS. 14C and 14G, the malignant lesion tends to have higher value and wider distribution of interstitial pressure; the median of $p_t$ for the malignant and benign tumors are $2.029 \times 10^4$ g·cm$^{-1}$·s$^{-2}$ and $2.015 \times 10^4$ g·cm$^{-1}$·s$^{-2}$, respectively. FIGS. 14D and 14H present the velocity vector fields in the malignant and benign tumors, with the arrow sizes scaled by the local vector magnitude. The magnitude of interstitial flow velocity in the benign tumor is smaller than the velocity in the malignant tumor, where the median of $|u_t|$ for the malignant and benign tumors are $7.72 \times 10^{-2}$ cm·s$^{-1}$ and $1.11 \times 10^{-2}$ cm·s$^{-1}$ respectively. In FIG. 14D, obvious inward interstitial flow is indicated by the velocity vectors at the superior regions of the malignant tumor, where a major input artery contacts the lesion. Outward flow vectors are also observed at the inferior and anterior regions of the tumor, while flow is weak in the medial and posterior regions. FIG. 14H shows the interstitial flow in the benign tumor.

Figures 15A, 15B:
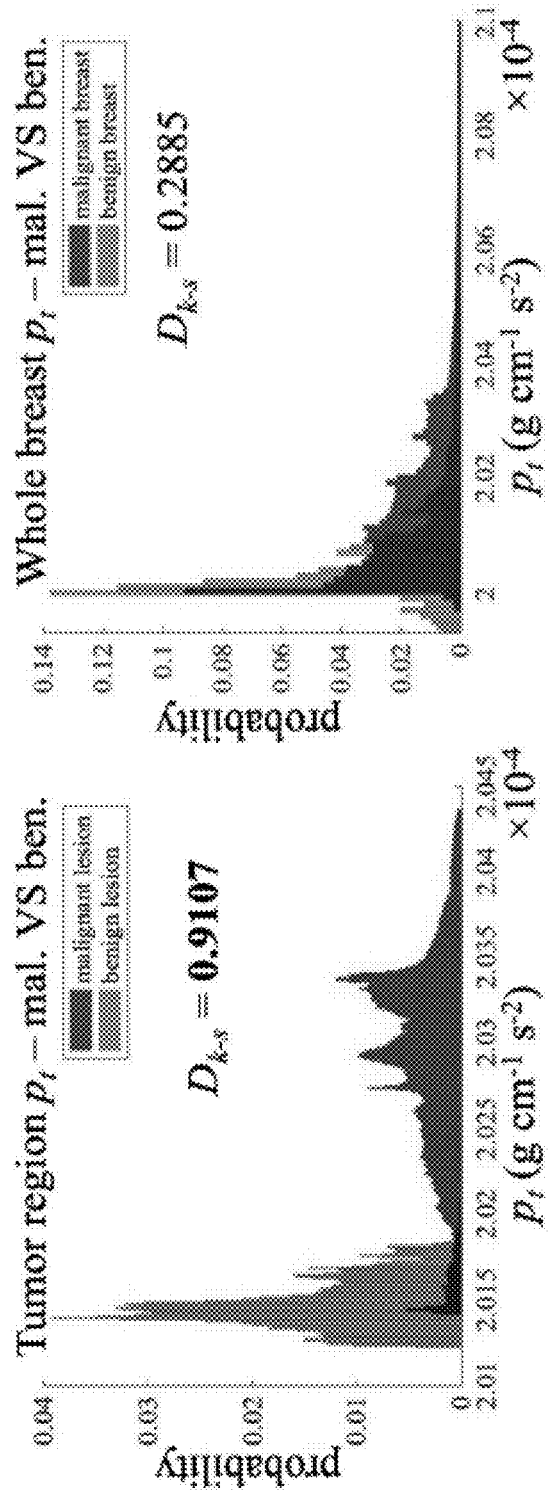
FIGS. 15A-15F depict comparison of hemodynamic characteristics distributions, with FIGS. 15A, 15C, and 15E characterizing tumor region interstitial pressure ($p_t$), interstitial flow velocity magnitude ($|u_t|$), and tumor-associated vascular extraction rate ($q_e$), respectively, and with FIGS. 15B, 15D, and 15E summarizing $p_t$, $|u_4|$, and $q_e$, respectively, in the whole diseased breast, according to potential embodiments. Red histograms represent distributions related to the malignant case, while blue histograms represent distributions relate to the benign case. Distributions of the characteristics present clear differences between the malignant and benign lesions; in particular the malignant case has higher medians and a larger range for these parameters. The differences are more pronounced in lesion-specific comparisons than in the whole breast comparisons.
Figures 15C, 15D:
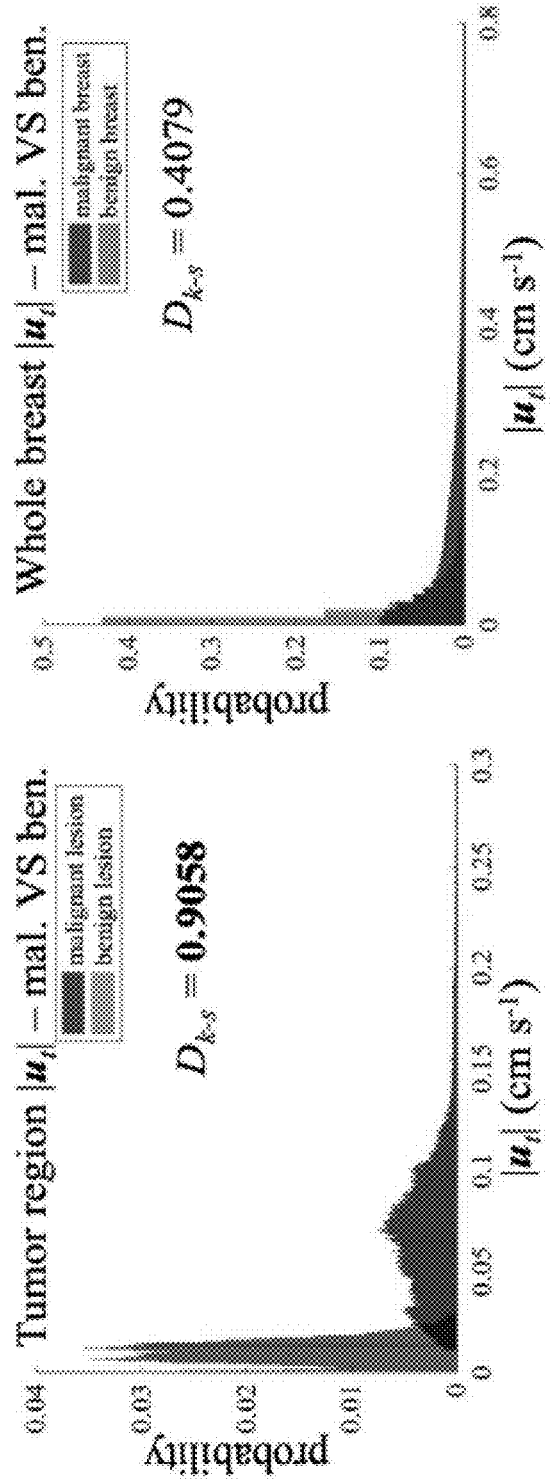
Figures 15E, 15F:
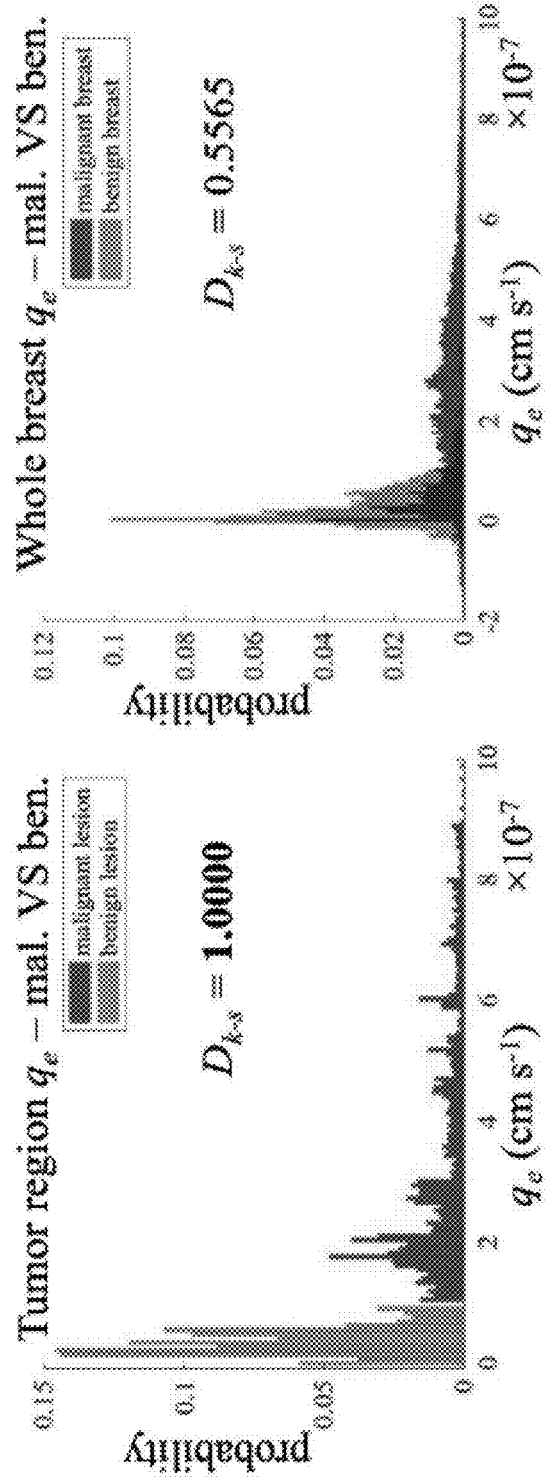

With respect to K-S comparison between whole breasts and lesions in hemodynamic characterization in various embodiments, complete results of K-S comparison of the hemodynamic characteristics of the malignant and benign disease are reported in Table 7, where the measure $D_{k-s}$ is defined as in Equation (35). For interstitial characteristics, FIGS. 15A and 15C show clear differences between malignant and benign tumor regions: $D_{k-s}=0.91$ and $D_{k-s}=0.91$ for $p_t$ and $|u_t|$, respectively. Concerning the characteristics of tumor-associated vessels, the $q_e$ distributions are completely separated ($D_{k-s}=1$) between the malignant and benign lesions (FIG. 15E), where the median of $q_e$ for the malignant and benign tumors are $5.20 \times 10^{-7}$ cm·s$^{-1}$ and $3.68 \times 10^{-8}$ cm·s$^{-1}$, respectively. These difference ($D_{k-s}>0.9$) were not observed when comparing the entire diseased and contralateral breast, or when comparing the entire malignant and benign breasts (Table 7).

TABLE 7

K-S Statistics summary of hemodynamic characteristics

| | K-S statistic ($D_{k-1}$) | | | |
|---|---|---|---|---|
| | Whole breast [a] | | Tumor [b] | |
| Characteristics | malignant vs contraleteral | benign vs contralaterial | malignant vs benign | malignant vs benign |
| *Interstitial* | | | | |
| $p_t$ (g cm$^{-1}$ s$^{-2}$) | 0.35 | 0.16 | 0.29 | 0.91 |
| $|u_t|$ (cm s$^{-1}$) | 0.24 | 0.13 | 0.41 | 0.91 |
| *Vascular* | | | | |
| $p_t$ (g cm$^{-1}$ s$^{-2}$) | 0.71 | 0.17 | 0.22 | 0.46 |
| $u_r$ (cm$^3$ s$^{-1}$) | 0.12 | 0.18 | 0.21 | 0.32 |

TABLE 7-continued

K-S Statistics summary of hemodynamic characteristics

| | K-S statistic ($D_{k-1}$) | | | |
|---|---|---|---|---|
| | Whole breast [a] | | | Tumor [b] |
| Characteristics | malignant vs contraleteral | benign vs contralateral | malignant vs benign | malignant vs benign |
| wss (g cm$^{-1}$ s$^{-2}$) | 0.09 | 0.14 | 0.22 | 0.30 |
| q$_s$ (cm s$^{-1}$) | 0.37 | 0.12 | 0.56 | 1.00 |

[a] mal. vs con.: comparison between the malignant diseased breast and contralateral breast; ben. vs con.: comparison between the benign diseased breast and contralateral breast; mal. vs ben.: comparison between the malignant and benign diseased breasts
[a] mal. vs ben.: comparison between the malignant and benign lesions With respect to vascular inlet/outlet patterns and blood flow rates in hemodynamic characterization, once the blood flow is determined within the vasculature, various implementations differentiate vascular inlets and outlets for each lesion to compute the total blood flow rate through the tumor. As shown in FIGS. 11A and 11F, one inlet vessel (red curve) and five outlet vessels (blue curves) are identified for the malignant lesion (FIG. 11A), while one inlet and two outlet vessels are identified for the benign lesion (FIG. 11F). The calculated total blood flow rate through the malignant tumor was 19.44 ml/dl/min, much higher than the benign tumor (2.12 ml/dl/min) and whole healthy tissue in the contralateral breasts (1.58 ml/dl/min and 0.97 ml/dl/min for the malignant and benign cases, respectively).

Various embodiments employ quantitative magnetic resonance imaging data to constrain a patient-specific, computational fluid dynamics model of blood flow and interstitial transport in breast cancer. In various implementations, a computational model may be established by applying Poiseuille's law for blood flow in the vascular network, Darcy's law for interstitial flow in the surrounding tissue, and/or Starling's law for interaction between the blood plasma and interstitial fluid. Segmentations on high resolution contrast-enhanced images may be used to generate 3D meshes and pseudo-1D vascular networks, which can inform the modeling domains. Furthermore, quantitative MRI parameters (i.e., BAT, $K^{trans}$, $v_p$, and ADC) may be adapted to refine the mesh, inform local material properties, and determine boundary conditions. The modeling system calibrated with patient-specific data may be implemented with a coupled, 1D FDM-3D FEM approach. The simulation directly may provide solutions of blood pressure and interstitial pressure fields, enabling calculation of blood flow velocity, blood flow rate, wall shear stress, extraction rate, and interstitial flow velocity.

Comparing K-S statistics for the computed hemodynamics indicate that the malignant tumor tends to present much higher values and wider standard deviations in the distributions of interstitial pressure, magnitude of interstitial velocity, and vascular extraction rate than those of the benign tumor as well as the healthy tissue. The calculated blood flow rates through the malignant lesion is also much higher than that of the benign lesion and healthy tissue. These results match with previous experimental observations showing malignant tumors present high interstitial fluid pressure, high vascular leakage, significant intratumoral heterogeneity in microenvironment, and high vascular perfusion.

Advantageously, embodiments of the disclosed approach provide the ability to spatially resolve the interstitial flow fields of a tumor. For example, the malignant tumor in demonstrative implementations discussed herein presents significant inward flow at the superior edge due to the localization of a major feeding artery, and outward flow on the inferior and anterior margins of the lesion; while the internal and posterior regions show much lower interstitial flow. Visualization of these phenomena may be used to provide additional, in vivo, information regarding invasion on an individual patient basis.

In various embodiments, a computational model, informed by patient-specific magnetic resonance imaging data, may be used to simulate the blood supply and interstitial fluid environment for breast or other tumors. Due to clear differences in hemodynamic characteristics between malignant and benign lesions, specifically interstitial fluid pressure, interstitial flow velocity, and vascular extraction rate, embodiments of the disclosed approach may provide a fundamentally new way to employ contrast agent pharmacokinetics for the evaluation of cancer.

Additional background and supporting information can be found in the following documents, each of which is herein incorporated by reference:

P. Vaupel, F. Kallinowski, P. Okunieff, Blood flow, oxygen and nutrient supply, and metabolic microenvironment of human tumors: a review. *Cancer Res.* 1989; 49(23):6449-6465.

J. M. Munson, A. C. Shieh. Interstitial fluid flow in cancer: implications for disease progression and treatment. *Cancer Manag Res.* 2014; 6:317.

R. K. Jain, J. D. Martin, T. Stylianopoulos. The role of mechanical forces in tumor growth and therapy. *Annu. Rev. Biomed. Eng.* 2014; 16:321-46.

M. A. Swartz, M. E. Fleury. Interstitial flow and its effects in soft tissues. *Annu Rev Biomed Eng.* 2007; 9:229-56.

R. Glicksman, N. Chaudary, M. Pintilie, E. Leung, B. Clarke, K. Sy, R. P. Hill, K. Han, A. Fyles, M. Milosevic. The predictive value of nadir neutrophil count during treatment of cervical cancer: Interactions with tumor hypoxia and interstitial fluid pressure (IFP). *Clin Transl Radiat. Oncol.* 2017; 6:15-20.

L. T. Baxter, R. K. Jain. Transport of fluid and macromolecules in tumors. I. Role of interstitial pressure and convection. *Microvas Res.* 1989; 37(1):77-104.

C. H. Heldin, K. Rubin, K. Pietras, A. Östman. High interstitial fluid pressure—an obstacle in cancer therapy. *Nat Rev Cancer.* 2004; 4(10):806.

K. M. Kingsmore, D. K. Logsdon, D. H. Floyd, S. M. Peirce, B. W. Purow, J. M. Munson. Interstitial flow differentially increases patient-derived glioblastoma stem cell invasion via CXCR4, CXCL12, and CD44-mediated mechanisms. *Integr Biol.* 2016; 8(12):1246-60.

J. D. Shields, M. E. Fleury, C. Yong, A. A. Tomei, G. J. Randolph, M. A. Swartz. Autologous chemotaxis as a mechanism of tumor cell homing to lymphatics via interstitial flow and autocrine CCR7 signaling. *Cancer Cell.* 2007; 11(6):526-38.

S. F. Chang, C. A. Chang, D. Y. Lee, P. L. Lee, Y. M. Yeh, C. R. Yeh, C. K. Cheng, S. Chien, J. J. Chiu. Tumor cell cycle arrest induced by shear stress: Roles of integrins and Smad. *Proc Natl Acad Sci.* 2008; 105(10):3927-32.

M. Schäfer, S. Werner. Cancer as an overhealing wound: an old hypothesis revisited. *Nat Rev Mol Cell Biol.* 2008; 9(8):628.

A. C. Shieh, H. A. Rozansky, B. Hinz, M. A. Swartz. Tumor cell invasion is promoted by interstitial flow-induced matrix priming by stromal fibroblasts. *Cancer Res.* 2011: 71(3):790-800.

S. Kim, M. Chung, J. Ahn, S. Lee, N. L. Jeon. Interstitial flow regulates the angiogenic response and phenotype of endothelial cells in a 3D culture model. *Lab Chip.* 2016; 16(21):4189-99.

F. W. Prinzen, J. B. Bassingthwaighte. Blood flow distributions by microsphere deposition methods. *Cardiovasc Res.* 2000; 45(1):13-21.

T. A. Zachos, S. W. Aiken, G. R. DiResta, J. H. Healey. Interstitial fluid pressure and blood flow in canine osteosarcoma and other tumors. *Clin Orthop Relat Res.* 2001; 385:230-6.

M. A. Lodge, H. A. Jacene, R. Pili, R. L. Wahl. Reproducibility of tumor blood flow quantification with 15O-water PET. *J Nucl Med.* 2008; 49(10):1620.

D. D. Adler, P. L. Carson, J. M. Rubin, D. Quinn-Reid. Doppler ultrasound color flow imaging in the study of breast cancer: preliminary findings. *Ultrasound Med Biol.* 1990; 16(6):553-9.

M. Kawashima, Y. Katada, T. Shukuya, M. Kojima, M. Nozaki. MR perfusion imaging using the arterial spin labeling technique for breast cancer. *J Magn Reson Imaging.* 2012; 35(2):436-40.

S. D. Nathanson, L. Nelson. Interstitial fluid pressure in breast cancer, benign breast conditions, and breast parenchyma. *Ann Surg Oncol.* 1994; 1(4):333-8.

K. M. Kingsmore, A. Vaccari, D. Abler, S. X. Cui, F. H. Epstein, R. C. Rockne, S. T. Acton, J. M. Munson. MRI analysis to map interstitial flow in the brain tumor microenvironment. *APL Bioeng.* 2018; 2(3):031905.

L. J. Liu, S. L. Brown, J. R. Ewing, B. D. Ala, K. M. Schneider, M. Schlesinger. Estimation of Tumor Interstitial Fluid Pressure (TIFP) Noninvasively. *PloS One.* 2016; 11(7):e0140892.

A. d'Esposito, P. W. Sweeney, M. Ali, M. Saleh, R. Ramasawmy, T. A. Roberts, G. Agliardi, A. Desjardins, M. F. Lythgoe, R. B. Pedley, R. Shipley. Computational fluid dynamics with imaging of cleared tissue and of in vivo perfusion predicts drug uptake and treatment responses in tumours. *Nat Biomed Eng.* 2018; 2(10):773.

E. Kim, S. Stamatelos, J. Cebulla, Z. M. Bhujwalla, A. S. Popel, A. P. Pathak. Multiscale imaging and computational modeling of blood flow in the tumor vasculature. *Ann Biomed Eng.* 2012; 40(11):2425-2441.

S. K. Stamatelos, E. Kim, A. P. Pathak, A. S. Popel. A bioimage informatics based reconstruction of breast tumor microvasculature with computational blood flow predictions. *Microvasc Res.* 2014; 91:8-21.

M. Sefidgar, M. Soltani, H. Bazmara, M. Mousavi, M. Bazargan, A. Elkamel. Interstitial flow in cancerous tissue: effect of considering remodeled capillary network. *J Tissue Sci Eng.* 2014; 54:2.

M. Soltani, P. Chen. Numerical modeling of interstitial fluid flow coupled with blood flow through a remodeled solid tumor microvascular network. *PloS One* 2013; 8(6): e67025.

C. Pozrikidis. Numerical simulation of blood and interstitial flow through a solid tumor. J Math Biol. 2010; 60(1):75-94.

M. Welter, H. Rieger. Interstitial fluid flow and drug delivery in vascularized tumors: a computational model. *PloS One.* 2013; 8(8):e70395.

Q. Sun, G. X. Wu. Coupled finite difference and boundary element methods for fluid flow through a vessel with multibranches in tumours. *Int J Numer Method Biomed Eng.* 2013; 29(3):309-331.

C. D'Angelo, Q. Alfio. On the coupling of 1d and 3d diffusion-reaction equations: application to tissue perfusion problems. *Math Mode is Methods Appl Sci.* 2008; 18(8):1481-1504.

J. P. Thirion, Image matching as a diffusion process: an analogy with Maxwell's demons. *Med Image Anal.* 1998; 2(3):243-60.

MATLAB and Image Processing Toolbox: User's Guide (R2016a), The MathWorks, Inc., Natick, Massachusetts, United States.

P. Thevenaz, U. E. Ruttimann, M. Unser. A pyramid approach to subpixel registration based on intensity. *IEEE Trans Image Process.* 1998; 7(1):27-41.

C. Wu, F. Pineda, D. A. Hormuth, G. S. Karczmar, T. E. Yankeelov. Quantitative analysis of vascular properties derived from ultrafast DCE-MRI to discriminate malignant and benign breast tumors. *Magn Reason Med.* 2019; 81(3):2147-2160.

W. Chen, M. L. Giger, U. Bick. A Fuzzy C-Means (FCM)-Based Approach for Computerized Segmentation of Breast Lesions in Dynamic Contrast-Enhanced MR Images. *Acad Radiol.* 2006; 13(1):63-72.

Z. Yu, C. Bajaj. "A fast and adaptive method for image contrast enhancement," in *Intl Conf on Image Processing.* 2004; 2:1001-1004

A. Vignati, V. Giannini, A. Bert, P. Borrelli, M. D. Luca, L. Martincich, F. Sardanelli, D. Regge. A Fully Automatic Multiscale 3-Dimensional Hessian-Based Algorithm for Vessel Detection in Breast DCE-MRI. *Invest Radiol.* 2012; 47(12):705-710.

T. E. Yankeelov, J. C. Gore, Dynamic contrast enhanced magnetic resonance imaging in oncology: theory, data acquisition, analysis, and examples. *Curr Med Imaging Rev.* 2007; 3(2):91-107.

R. Woodhams, S. Ramadan, P. Stanwell, S. Sakamoto, H. Hata, M. Ozaki, S. Kan, Y. Inoue. Diffusion-weighted imaging of the breast: principles and clinical applications. *Radiographics.* 2011; 31(4):1059-84.

G. Steidle, F Eibofner, F Schick. Quantitative diffusion imaging of adipose tissue in the human lower leg at 1.5 T. *Magn Reson Med.* 2011; 65(4):1118-24.

Q. Fang, D. A. Boas. "Tetrahedral mesh generation from volumetric binary and grayscale images," in *IEEE Int Symp Biomed Imaging,* 2009; 1142-1145.

B. C. Fry, J. Lee, N. P. Smith, T. W. Secomb. Estimation of blood flow rates in large microvascular networks. *Microcirculation.* 2012; 19(6):530-8.

A. R. Pries, T. W. Secomb, P. Gaehtgens. Biophysical aspects of blood flow in the microvasculature. *Cardiovasc Res.* 1996; 32:654-667.

T. J. Pedley. The fluid mechanics of large blood vessels (Cambridge Monographs on Mechanics). Cambridge, Cambridge University Press. 1980.

A. Logg, K. A. Mardal, G. Wells. Automated Solution of Differential Equations by the Finite Element Method: the FEniCS book. Springer, 2012.

J. W. Baish, P. A. Netti, R. K. Jain. Transmural coupling of fluid flow in microcirculatory network and interstitium in tumors. *Microvasc Rese.* 1997:53(2):128-141.

E. A. Swabb, J. Wei, P. M. Gullino. Diffusion and Convection in Normal and Neoplastic Tissues", *Cancer Res.* 1974; 34(10):2814-2822.

H. Maeda, J. Wu, T. Sawa, Y. Matsumura, K. Hori. Tumor vascular permeability and the EPR effect in macromolecular therapeutics: a review. *J Control Release.* 2000; 65(1-2):271-84.

K. Polyak. Heterogeneity in breast cancer. *J Clin Invest.* 2011; 121(10):3786-3788.

R. Beaney, T. Jones, A. Lammertsma, C. Mckenzie, K. Halnan. Positron emission tomography for in-vivo measurement of regional blood flow, oxygen utilisation, and blood volume in patients with breast carcinoma. Lancet. 1984; 323(8369):131-134.

C. B. Wilson, A. A. Lammertsma, C. G. McKenzie, K. Sikora, T. Jones. Measurements of blood flow and exchanging water space in breast tumors using positron emission tomography: a rapid and noninvasive dynamic method. *Cancer Res.* 1992; 52(6):1592-1597.

R. T. Woodall, S. L. Barnes, D. A. Hormuth, A. G. Sorace, C. C. Quarles, T. E. Yankeelov. The effects of intravoxel contrast agent diffusion on the analysis of DCE-MRI data in realistic tissue domains. *Magn Reson Med.* 2018; 80(1):330-340.

T. O. Easley, F. Pineda, B. Kim, R. Foygel-Barber, C. Wu, T. E. Yankeelov, X. Fan, D. Sheth, D. Schacht, H. Abe, G. S. Karczmar. "A new approach to quantitative measurement of breast tumor blood flow capillary permeability," in *Proc Intl Soc Magn Reson Med* 27. 2019; Abstract #2262.

D. S. Tuch, V. J. Wedeen, A. M. Dale, J. S. George, J. W. Belliveau. Conductivity tensor mapping of the human brain using diffusion tensor MRI. *Proc Natl Acad Sci.* 2001; 98(20):11697-11701.

E. Carson, C. Cobelli. Modeling Methodology for Physiology and Medicine. Newnes, 2001, Chapter17, pp. 373-401.

Yankeelov T E, Gore J. Dynamic contrast enhanced magnetic resonance imaging in oncology: theory, data acquisition, analysis, and examples. Curr Med Imaging Rev. 2007; 3:91-107.

Mann R M, Balleyguier C, Baltzer P A, et al. Breast MRI: EUSOBI recommendations for women's information. Eur Radiol. 2015; 25:3669-3678.

Partridge S C, Stone K M, Strigel R M, Demartini W B, Peacock S, Lehman C D. Breast DCE-MRI: influence of post-contrast timing on automated lesion kinetics assessments and discrimination of benign and malignant lesions. Acad Radiol. 2014; 21:1195-1203.

Houssami N, Hayes D F. Review of preoperative magnetic resonance imaging (MRI) in breast cancer: should MRI be performed on all women with newly diagnosed, early stage breast cancer? C A Cancer J Clin. 2009; 59:290-302.

Hylton N M, Blume J D, Bernreuter W K, et al. Locally advanced breast cancer: MR imaging for prediction of response to neoadjuvant chemotherapy—results from ACRIN 6657/I-SPY TRIAL. Radiology. 2012; 263:663-672.

Drisis S, Metens T, Ignatiadis M, Stathopoulos K, Chao S L, Lemort M. Quantitative DCE-MRI for prediction of pathological complete response following neoadjuvant treatment for locally advanced breast cancer: the impact of breast cancer subtypes on the diagnostic accuracy. Eur Radiol. 2015; 26:1474-1484.

Virostko J, Hainline A, Kang H, et al. Dynamic contrast-enhanced magnetic resonance imaging and diffusion-weighted magnetic resonance imaging for predicting the response of locally advanced breast cancer to neoadjuvant therapy: a meta-analysis. J Med Imaging. 2017; 5:1.

Peters N H G M, Rinkes I H M B, Zuithoff N P A, Mali W P T M, Moons K G M, Peeters P H M. Meta-analysis of MR imaging in the diagnosis of breast lesions. Radiology. 2008; 246:116-124. Huang W, Fisher P R, Dulaimy K, Tudorica L A, O'Hea B, Button T M. Detection of breast malignancy: diagnostic MR protocol for improved specificity. Radiology. 2004; 232:585-591.

Mahfouz A E, Sherif H, Saad A, et al. Gadolinium-enhanced MR angiography of the breast: is breast cancer associated with ipsilateral higher vascularity? Eur Radiol. 2001; 11:965-969.

Wright H, Listinsky J, Quinn C, Rim A, Crowe J, Kim J. Increased ipsilateral whole breast vascularity as measured by contrast-enhanced magnetic resonance imaging in patients with breast cancer. Am J Surg. 2005; 190:576-579.

Sardanelli F, Iozzelli A, Fausto A, Carriero A, Kirchin M A. Gadobenate dimeglumine-enhanced MR imaging breast vascular maps: association between invasive cancer and ipsilateral increased vascularity. Radiology. 2005; 235:791-797.

Sardanelli F, Fausto A, Menicagli L, Esseridou A. Breast vascular mapping obtained with contrast-enhanced MR imaging: implications for cancer diagnosis, treatment, and risk stratification. Eur Radiol. 2007; 17(S6):48-51.

Schmitz A C, Peters NHGM, Veldhuis W B, et al. Contrast-enhanced 3.0-T breast MRI for characterization of breast lesions: increased specificity by using vascular maps. Eur Radiol. 2007; 18:355-364.

Verardi N, Leo G D, Carbonaro L A, Fedeli M P, Sardanelli F. Contrast-enhanced MR imaging of the breast: association between asymmetric increased breast vascularity and ipsilateral cancer in a consecutive series of 197 patients. Radiol Med. 2012; 118:239-250.

Sardanelli F. Vessel analysis on contrast-enhanced MRI of the breast: global or local vascularity? AJR Am J Roentgenol. 2010; 195:1246-1249.

Malich A, Fischer D R, Wurdinger S, et al. Potential MRI interpretation model: differentiation of benign from malignant breast masses. AJR Am J Roentgenol. 2005; 185:964-970.

Kul S, Cansu A, Alhan E, Dine H, Reis A, an Çan G. Contrast-enhanced MR angiography of the breast: evaluation of ipsilateral increased vascularity and adjacent vessel sign in the characterization of breast lesions. AJR Am J Roentgenol. 2010; 195:1250-1254.

Dietzel M, Baltzer P A, Vag T, et al. The adjacent vessel sign on breast MRI: new data and a subgroup analysis for 1,084 histologically verified cases. Korean J Radiol. 2010; 11:178.

Deschamps F, Solomon S B, Thornton R H, et al. Computed analysis of three-dimensional cone-beam computed tomography angiography for determination of tumor-feeding vessels during chemoembolization of liver tumor: a pilot study. Cardiovasc Intervent Radiol. 2010; 33:1235-1242.

Pinker K, Grabner G, Bogner W, et al. A combined high temporal and high spatial resolution 3 Tesla MR imaging protocol for the assessment of breast lesions: initial results. Invest Radiol. 2009; 44:553-558.

Planey C R, Welch E B, Xu L, et al. Temporal sampling requirements for reference region modeling of DCE-MRI data in human breast cancer. J Magn Reson Imaging. 2009; 30:121-134.

Jansen S A, Fan X, Medved M, et al. Characterizing early contrast uptake of ductal carcinoma in situ with high temporal resolution dynamic contrast-enhanced MRI of the breast: a pilot study. Phys Med Biol. 2010; 55:N473-N485.

Pineda F D, Medved M, Wang S, et al. Ultrafast bilateral DCE-MRI of the breast with conventional fourier sampling. Acad Radiol. 2016; 23:1137-1144.

Onishi N, Kataoka M, Kanao S, et al. Ultrafast dynamic contrast-enhanced MRI of the breast using compressed sensing: breast cancer diagnosis based on separate visualization of breast arteries and veins. J Magn Reson Imaging. 2017; 47:97-104.

Abe H, Mori N, Tsuchiya K, et al. Kinetic analysis of benign and malignant breast lesions with ultrafast dynamic contrast-enhanced MRI: comparison with standard kinetic assessment. AJR Am J Roentgenol. 2016; 207:1159-1166.

Georgiou L, Sharma N, Broadbent D A, et al. Estimating breast tumor blood flow during neoadjuvant chemotherapy using interleaved high temporal and high spatial resolution MRI. Magn Reson Med. 2017; 79:317-326.

Kuhl C K, Schrading S, Strobel K, Schild H H, Hilgers R D, Bieling H B. Abbreviated breast magnetic resonance imaging (MRI): first postcontrast subtracted images and maximum-intensity projection—a novel approach to breast cancer screening with MRI. J Clin Oncol. 2014; 32:2304-2310.

Mann R M, Mus R D, van Zelst J, Geppert C, Karssemeijer N, Platel B. A novel approach to contrast-enhanced breast magnetic resonance imaging for screening: high-resolution ultrafast dynamic imaging. Invest Radiol. 2014; 49:579-585.

Mus R D, Borelli C, Bult P, et al. Time to enhancement derived from ultrafast breast MRI as a novel parameter to discriminate benign from malignant breast lesions. Eur Radiol. 2017; 89:90-96.

Thirion J P. Image matching as a diffusion process: an analogy with Maxwells demons. Med Image Anal. 1998; 2:243-260.

Chen W, Giger M L, Bick U. A fuzzy C-means (FCM)-based approach for computerized segmentation of breast lesions in dynamic contrast-enhanced MR images. Acad Radiol. 2006; 13:63-72.

Yu Z, Bajaj C. A fast and adaptive method for image contrast enhancement. In Proceedings of the 2004 International Conference on Image Processing, Singapore, 2004:1001-1004.

Frangi A F, Niessen W J, Vincken K L, Viergever M A. Multiscale vessel enhancement filtering. In: Wells W M, Colchester A, Delp S, editors. Medical image computing and computer-assisted intervention—MICCAI'98. MICCAI 1998. Lecture Notes in Computer Science, vol 1496. Berlin, Heidelberg: Springer; 1998 p 130-137.

Vignati A, Giannini V, Bert A, et al. A fully automatic multiscale 3-dimensional Hessian-based algorithm for vessel detection in breast DCE-MRI. Invest Radiol. 2012; 47:705-710.

Vignati A, Giannini V, Carbonaro L, et al. A new algorithm for automatic vascular mapping of DCE-MRI of the breast: clinical application of a potential new biomarker. Comput Methods Programs Biomed. 2014; 117:482-488.

Wang L, Schnurr A K, Zidowitz S. Segmentation of hepatic artery in multi-phase liver C T using directional dilation and connectivity analysis. In Proceedings of the SPIE Medical Imaging Conference, San Diego, C A, 2016: 97851P.

Vignati A, Giannini V, Luca M D, et al. Performance of a fully automatic lesion detection system for breast DCE-MRI. J Magn Reson Imaging. 2011; 34:1341-1351.

Risser L, Plouraboue F, Descombes X. Gap filling of 3-D micro-vascular networks by tensor voting. IEEE Trans Med Imaging. 2008; 27:674-687.

Dijkstra E W. A note on two problems in connexion with graphs. Numer Math. 1959; 1:269-271.

Li X, Welch E B, Arlinghaus L R, et al. A novel AIF tracking method and comparison of DCE-MRI parameters using individual and population-based AIFs in human breast cancer. Phys Med Biol. 2011; 56:5753-5769.

Bullitt E, Gerig G, Pizer S, Lin W, Aylward S. Measuring tortuosity of the intracerebral vasculature from MRA images. IEEE Trans Med Imaging. 2003; 22:1163-1171.

Petrillo A, Fusco R, Filice S, et al. Breast contrast enhanced MR imaging: semi-automatic detection of vascular map and predominant feeding vessel. PloS One. 2016; 11:e0161691.

Vreemann S, Gubern-Mdrida A, Borelli C, Bult P, Karssemeijer N, Mann R M. The correlation of background parenchymal enhancement in the contralateral breast with patient and tumor characteristics of MRI-screen detected breast cancers. PloS One. 2018; 13:e0191399.

Campbell I C, Coudrillier B, Mensah J, Abel R L, Ethier C R. Automated segmentation of the lamina cribrosa using Frangis filter: a novel approach for rapid identification of tissue volume fraction and beam orientation in a trabeculated structure in the eye. J Royal Soc Interface. 2015; 12:20141009.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the terms "exemplary," "example," "potential," and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below") are merely used to describe the orientation of various elements in the Figures. It should be noted that the orientation of various elements may differ according to other exemplary embodiments, and that such variations are intended to be encompassed by the present disclosure.

The embodiments described herein have been described with reference to drawings. The drawings illustrate certain details of specific embodiments that implement the systems, methods and programs described herein. However, describing the embodiments with drawings should not be construed as imposing on the disclosure any limitations that may be present in the drawings.

It is important to note that the construction and arrangement of the devices, assemblies, and steps as shown in the various exemplary embodiments is illustrative only. Additionally, any element disclosed in one embodiment may be incorporated or utilized with any other embodiment disclosed herein. Although only one example of an element from one embodiment that can be incorporated or utilized in another embodiment has been described above, it should be appreciated that other elements of the various embodiments may be incorporated or utilized with any of the other embodiments disclosed herein.

The foregoing description of embodiments has been presented for purposes of illustration and description. It is not intended to be exhaustive or to limit the disclosure to the precise form disclosed, and modifications and variations are possible in light of the above teachings or may be acquired from this disclosure. The embodiments were chosen and described in order to explain the principals of the disclosure and its practical application to enable one skilled in the art to utilize the various embodiments and with various modifications as are suited to the particular use contemplated. Other substitutions, modifications, changes and omissions may be made in the design, operating conditions and arrangement of the embodiments without departing from the scope of the present disclosure as expressed in the appended claims.

What is claimed is:

1. A computer-implemented method of non-invasively characterizing a tumor in a region of interest (ROI) based on tumor hemodynamics determined using magnetic resonance imaging (MRI) data, the method comprising:
    acquiring, by a computing system, MRI data of a ROI comprising:
        a first MRI dataset corresponding to high spatial resolution dynamic contrast enhanced MRI (DCE-MRI) scans of the ROI;
        a second MRI dataset corresponding to high temporal resolution DCE-MRI scans of the ROI; and
        a third MRI dataset corresponding to diffusion-weighted MRI (DW-MRI) scans of the ROI;
    determining, by the computing system, vasculature metrics using the first MRI dataset, the second MRI dataset, and the third MRI dataset;
    determining, by the computing system, at least one of tumor-associated blood flow velocity or tumor interstitial pressure by using the vasculature metrics as inputs to a computational fluid dynamics model; and
    generating, by the computing system, at least one tumor characteristic based on determining the at least one of tumor-associated blood flow velocity and tumor interstitial pressure.

2. The method of claim 1, wherein the vasculature metrics include one or more values corresponding to tumor-associated vessel morphology and blood flow.

3. The method of claim 1, wherein determining vasculature metrics comprises detecting, by the computing system, tumor-associated vessels using the first MRI dataset.

4. The method of claim 1, wherein determining vasculature metrics comprises segmenting, by the computing device, the tumor from surrounding tissue.

5. The method of claim 4, wherein segmenting the tumor comprises applying, by the computing system, fuzzy clustering to the first MRI dataset.

6. The method of claim 4, wherein segmenting the vasculature comprises applying, by the computing system, a multi-scale filter to generate a probability histogram representing probabilities of voxels comprising blood vessels.

7. The method of claim 6, wherein the multi-scale filter comprises a Hessian-based filter, and wherein the method further comprises setting, by the computing system, a threshold by applying the Hessian-based filter to a region of fixed size covering internal thoracic vessels and using a percentile of the probability histogram as the threshold.

8. The method of claim 6, further comprising applying, by the computing system, a lowest-cost tracking function to detect at least one of (i) vessel segments likely to be in contact with the tumor, or (ii) paths connecting segmented vessels with the tumor.

9. The method of claim 1, wherein determining vasculature metrics comprises generating, by the computing system, at least one of (i) one or more parametric maps for one or more image processing parameters through analysis of the second and third MRI datasets, or (ii) numerical meshes for the ROI from segmented masks obtained from the acquired MRI data.

10. The method of claim 1, wherein determining vasculature metrics comprises applying, by the computing device, an adaptive vessel scaling function to integrate information from a segmented vascular mask and a plasma volume fraction ($v_p$) map, wherein applying the adaptive vessel scaling function comprises, by the computing system:
    skeletonizing the segmented vascular mask to a centerline of the segmented vascular mask;
    up-sampling the segmented vascular mask and the vp map to an isotropic resolution; and
    at a location along the centerline, identifying a neighborhood in an up-sampled grid using vascular orientation and a step width of half of an up-sampled voxel size, wherein the neighborhood represents a region of the segmented vascular mask covering a section of vessel at the location.

11. The method of claim 1, wherein determining vasculature metrics comprises generating, by the computing system, a contrast-agent pharmacokinetics model with respect to the tumor using the second and third MRI datasets, wherein generating the contrast-agent pharmacokinetics model comprises applying, by the computing system, a graphical analysis that uses linear regression to identify and analyze pharmacokinetics of the contrast agent.

12. The method of claim 1, wherein determining vasculature metrics comprises generating, by the computing system, a parametric map of apparent diffusion coefficient contrast-agent pharmacokinetics with respect to the tumor using the second and third MRI datasets.

13. The method of claim 1, wherein determining the at least one of tumor-associated blood flow velocity and tumor interstitial pressure comprises applying, by the computing system, a fluid dynamics function to quantify at least one of: (i) volumetric blood flow rate, or (ii) interstitial blood flow, or (iii) flux across vascular walls.

14. The method of claim 1, wherein;
   ii the first MRI dataset corresponds to fat-suppressed DCE-MRI scans with spatial resolutions less than two cubic millimeters, wherein the DCE-MRI scans of the first MRI dataset have temporal resolutions greater than 30 seconds; and
   (ii) the second MRI dataset comprises ultrafast DCE-MRI data corresponding to ultrafast DCE-MRI scans with temporal resolutions less than five seconds, wherein the ultrafast DCE-MRI scans have spatial resolutions greater than five cubic millimeters ($mm^3$).

15. The method of claim 1, further comprising outputting, via the computing system, the tumor characteristic, wherein the tumor characteristic comprises a characterization of tumor malignancy, aggressiveness or expected responsiveness of the tumor to a therapy.

16. A computer-implemented method of non-invasively characterizing a tumor by mapping pressure and flow fields in a region of interest (ROI) using quantitative magnetic resonance imaging (MRI) data, the method comprising:
   acquiring, by a computing system, MRI data comprising dynamic contrast enhanced MRI (DCE-MRI) scans of the ROI and diffusion-weighted MRI (DW-MRI) scans of the ROI;
   dividing, by the computing system, the ROI into a vascular space and an interstitial space by segmenting the MRI data, the vascular space comprising a blood vessel network, and the interstitial space comprising interstitial tissue;
   assigning, by the computing system, corresponding material properties to the vascular space and the interstitial space via analysis of MRI data corresponding to both the DCE-MRI and DW-MRI scans;
   applying, by the computing system, a computational fluid dynamics model to determine hemodynamics related metrics of a tumor in the ROI; and
   generating, by the computing system, an indication of malignancy of the tumor based on the hemodynamics related metrics of the tumor.

17. The method of claim 16, wherein applying the computational fluid dynamics model comprises determining, by the computing system, at least one of (i) interstitial fluid pressure, (ii) interstitial flow velocity, or (iii) blood flow within the blood vessel network along centerlines of the blood vessel network.

18. A computer-implemented method of non-invasively characterizing a tumor in a region of interest (ROI), the method comprising:
   acquiring, by a computing system, a first magnetic resonance imaging (MRI) dataset corresponding to high spatial resolution scans of the ROI, and a second MRI dataset corresponding to high temporal resolution scans of the ROI, the scans of the first and second MRI datasets at least partially overlapping in time;
   determining, by the computing system, at least one morphological vascular metric using the first MRI dataset;
   determining, by the computing system, at least one functional vascular metric using the second MRI dataset; and
   generating, by the computing system, at least one tumor characteristic based on both of the at least one morphological metric and the at least one functional metric.

19. The method of claim 18, wherein:
   i) the at least one morphological vascular metric comprises at least one of a vessel count or vessel tortuosity,
   (ii) the at least one functional vascular metric comprises one or more of bolus arrival time, volume transfer coefficient ($K^{trans}$), or plasma volume fraction ($v_p$), and
   (iii) the characterization of the tumor is based on a combination of the morphological vascular metric of vessel count and the functional vascular metric of bolus arrival time.

20. The method of claim 18, wherein determining the at least one morphological vascular metric comprises segmenting, by the computing system, the tumor from surrounding tissue, wherein segmenting the tumor from surrounding tissue comprises applying, by the computing system, fuzzy clustering to data in the first MRI dataset.

* * * * *